(12) United States Patent
Bristol et al.

(10) Patent No.: US 12,178,917 B2
(45) Date of Patent: *Dec. 31, 2024

(54) BETA-LACTAMASE FORMULATIONS AND USES THEREOF

(71) Applicant: Theriva Biologics, Inc., Rockville, MD (US)

(72) Inventors: Andrew Bristol, Rockville, MD (US); Michael Kaleko, Rockville, MD (US); Sheila Connelly, Rockville, MD (US)

(73) Assignee: Theriva Biologics, Inc., Rockville, MD (US)

( * ) Notice: Subject to any disclaimer, the term of this patent is extended or adjusted under 35 U.S.C. 154(b) by 885 days.

This patent is subject to a terminal disclaimer.

(21) Appl. No.: 17/034,534

(22) Filed: Sep. 28, 2020

(65) Prior Publication Data

US 2021/0007994 A1 Jan. 14, 2021

Related U.S. Application Data

(63) Continuation of application No. 16/111,477, filed on Aug. 24, 2018, now Pat. No. 10,828,260, which is a continuation of application No. 14/878,155, filed on Oct. 8, 2015, now Pat. No. 10,105,322.

(60) Provisional application No. 62/205,443, filed on Aug. 14, 2015, provisional application No. 62/126,556, filed on Feb. 28, 2015, provisional application No. 62/061,507, filed on Oct. 8, 2014.

(51) Int. Cl.
| | |
|---|---|
| *A61K 9/28* | (2006.01) |
| *A61K 9/20* | (2006.01) |
| *A61K 9/48* | (2006.01) |
| *A61K 9/50* | (2006.01) |
| *A61K 38/50* | (2006.01) |
| *A61K 45/06* | (2006.01) |

(52) U.S. Cl.
CPC .......... *A61K 9/2873* (2013.01); *A61K 9/2013* (2013.01); *A61K 9/2018* (2013.01); *A61K 9/2027* (2013.01); *A61K 9/2054* (2013.01); *A61K 9/4808* (2013.01); *A61K 9/4858* (2013.01); *A61K 9/4866* (2013.01); *A61K 9/5078* (2013.01); *A61K 38/50* (2013.01); *A61K 45/06* (2013.01); *C12Y 305/02006* (2013.01)

(58) Field of Classification Search
CPC .. A61K 9/2873; A61K 9/2013; A61K 9/2018; A61K 9/2027; A61K 9/2054; A61K 9/4808; A61K 9/4858; A61K 9/4866; A61K 9/5078; A61K 38/50; A61K 45/06; C12Y 305/02006; A61P 1/00; A61P 1/14
See application file for complete search history.

(56) References Cited

U.S. PATENT DOCUMENTS

| | | | |
|---|---|---|---|
| 2,890,986 A | | 6/1959 | Kraut et al. |
| 2,941,995 A | | 6/1960 | Doyle et al. |
| 2,982,696 A | | 5/1961 | Puetzer et al. |
| 3,070,511 A | | 12/1962 | Weitnauer |
| 3,150,059 A | | 9/1964 | Kleinschmidt et al. |
| 3,239,394 A | | 3/1966 | Walton |
| 3,488,729 A | | 1/1970 | Chauvette et al. |
| 3,499,909 A | | 3/1970 | Weissenburger et al. |
| 5,817,338 A | * | 10/1998 | Bergstrand ................. A61P 1/00 424/490 |
| 6,328,994 B1 | * | 12/2001 | Shimizu ................. A61K 9/5042 424/490 |
| 7,319,030 B2 | | 1/2008 | Koski et al. |
| 7,989,192 B2 | | 8/2011 | Kaariainen et al. |
| 8,894,994 B2 | | 11/2014 | Koski et al. |
| 9,034,602 B2 | | 5/2015 | Koski et al. |
| 9,290,754 B2 | * | 3/2016 | Kaleko .................. A61K 38/50 |
| 9,301,995 B2 | * | 4/2016 | Koski .................... A61K 45/06 |
| 9,376,673 B1 | * | 6/2016 | Kaleko .................... C12N 9/86 |
| 9,404,103 B1 | * | 8/2016 | Kaleko .................. A61K 38/50 |
| 9,464,280 B1 | * | 10/2016 | Kaleko .................. A61K 45/06 |
| 9,695,409 B2 | * | 7/2017 | Kaleko .................. A61K 31/546 |
| 9,744,221 B2 | * | 8/2017 | Kaleko .................. A61K 38/50 |
| 9,783,797 B1 | * | 10/2017 | Kaleko .................. A61K 45/06 |
| 10,011,824 B2 | * | 7/2018 | Kaleko .................. A61K 45/06 |
| 10,041,056 B2 | * | 8/2018 | Koski .................... A61P 1/08 |
| 10,046,035 B2 | * | 8/2018 | Kaleko ............. A61K 31/7056 |
| 10,087,433 B1 | * | 10/2018 | Kaleko .................... A61P 43/00 |
| 10,253,306 B2 | * | 4/2019 | Koski ..................... C12N 9/86 |
| 10,336,995 B2 | * | 7/2019 | Kaleko ................. A61K 9/0053 |

(Continued)

FOREIGN PATENT DOCUMENTS

| | | |
|---|---|---|
| EP | 0384559 A1 | 8/1990 |
| EP | 0420600 A2 | 4/1991 |

(Continued)

OTHER PUBLICATIONS

Rowe, RC et al. "Sugar Spheres." in: Handbook of Pharmaceutical Excipients (Chicago, Pharmaceutical Press, 2009), pp. 712-714. (Year: 2009).*

(Continued)

*Primary Examiner* — David W Berke-Schlessel
*Assistant Examiner* — Susan E. Fernandez
(74) *Attorney, Agent, or Firm* — Morgan, Lewis & Bockius LLP

(57) ABSTRACT

The present invention provides, in part, formulations comprising a beta-lactamase. Particularly, modified-release formulations comprising a beta-lactamase are provided which release a substantial amount of the beta-lactamase in the intestines. Therapeutic uses of the beta-lactamase formulations are also provided.

16 Claims, 27 Drawing Sheets

Specification includes a Sequence Listing.

(56) References Cited

U.S. PATENT DOCUMENTS

| | | | | |
|---|---|---|---|---|
| 10,584,326 | B2* | 3/2020 | Kaleko | A61K 45/06 |
| 10,767,171 | B2* | 9/2020 | Kaleko | A61P 39/02 |
| 11,236,319 | B2* | 2/2022 | Kaleko | C12Y 305/02006 |
| 11,253,577 | B2* | 2/2022 | Sliman | A61K 38/50 |
| 11,608,494 | B2* | 3/2023 | Kaleko | A61K 45/06 |
| 2004/0248279 | A1 | 12/2004 | Sawada et al. | |
| 2005/0158843 | A1 | 7/2005 | Koski et al. | |
| 2005/0249716 | A1 | 11/2005 | Bourgeois et al. | |
| 2006/0110451 | A1* | 5/2006 | Lin | A61P 25/00 |
| | | | | 424/464 |
| 2009/0181004 | A1 | 7/2009 | Kaariainen et al. | |
| 2009/0311234 | A1 | 12/2009 | Koski et al. | |
| 2013/0216622 | A1 | 8/2013 | Koski et al. | |
| 2014/0128431 | A1 | 5/2014 | Anand et al. | |

FOREIGN PATENT DOCUMENTS

| | | | |
|---|---|---|---|
| EP | 0420600 | A3 | 11/1992 |
| EP | 1564286 | A1 | 8/2005 |
| FI | 59265 | B | 3/1981 |
| FI | 880017 | A | 7/1988 |
| GB | 1241844 | A | 8/1971 |
| GB | 1463513 | A | 2/1977 |
| GB | 2199582 | A | 7/1988 |
| WO | WO 88/07865 | A1 | 10/1988 |
| WO | WO 93/13795 | A1 | 7/1993 |
| WO | WO 97/03185 | A1 | 1/1997 |
| WO | WO-0167879 | A1 * | 9/2001 ........... A23C 9/1216 |
| WO | WO 03/040352 | A1 | 5/2003 |
| WO | WO 2004/016248 | A2 | 2/2004 |
| WO | WO 2005/078075 | A2 | 8/2005 |
| WO | WO 2006/122835 | A1 | 11/2006 |
| WO | WO 2007/147945 | A1 | 12/2007 |
| WO | WO 2008/065247 | A1 | 6/2008 |
| WO | WO-2011140106 | A1 * | 11/2011 ........... A61K 38/465 |
| WO | 2011148041 | A1 | 12/2011 |
| WO | 2015161243 | | 10/2015 |

OTHER PUBLICATIONS

Result 2 of SEQ ID No. 1 search performed on A_GeneSeq database. Performed on Sep. 7, 2023. (Year: 2023).*
Result 16 of SEQ ID No. 3 search performed on A_GeneSeq database. Performed on Sep. 7, 2023. (Year: 2023).*
Schroeder, MS. Clostridium difficile-associated diarrhea. American Family Physician. 2005. 71(5): 921-928. (Year: 2005).*
Bristol, A et al. Formulation development of SYN-004 (ribaxamase) oral solid dosage form, a beta-lactamase to prevent intravenous antibiotic-associated dysbiosis of the colon. International Journal of Pharmaceutics. 2017. 534: 25-34. (Year: 2017).*
Gaujoux et al., "A flexible R package for nonnegative matrix factorization," BMC Bioinformatics, 11(1), 367 (2010).
Hasan et al., "Microbial Community Profiling of Human Saliva Using Shotgun Metagenomic Sequencing," PloS ONE 9(5): e97699. doi:10.1371/journal.pone.0097699 (2014).
Lax et al., "Longitudinal analysis of microbial interaction between humans and the indoor environment," Science 345, 1048 (2014); DOI:1126/science.1254529 (2014).
Pimentel et al., "Methanogens in human health and disease," Am. J. Gastroenter. Supp. 1(1), 28-33 (2012).
Tibhirani et al., "Diagnosis of multiple cancer types by shrunken centroids of gene expression," PNAS 99(10), 6567-6572 (2002).
Van Velzen et al., "Comparative and experimental pathology of fibrosing colonopathy," Postgrad Med J., vol. 72 Suppl 2:S39-48 (1996).
Fey et al., "Ceftriaxone-resistant *Salmonella* infection acquired by a child from cattle," New England J. Med., 342, 1242-49 (2000).
Fonze et al., Crystal Structures of the Bacillus licheniformis BS3 Class A β-Lactamase and of the Acyl-Enzyme Adduct Formed with Cefoxitin, Biochemistry, 41, 1877-85 (2002).

Jones et al., "Cefoperazone: A Review of Its Antimicrobial Spectrum, β-Lactamase Stability, Enzyme Inhibition, and Other in Vitro Characteristics," Rev. Infectious Disease 5 S108-S126 (1983).
Beta-Lactamase [*Bacillus* sp. CPSM8], Database GeneBank: ETB69002. 1, Dec. 9, 2013, [retrieved on Dec. 17, 2015]. Retrieved from the Internet: URL: https://ncbi.nlm.nih.gov/.
International Search Report and Written Opinion from the PCT Application No. PCT/US2015/054606, 9 pages, dated Jan. 14, 2016.
Altschul et al., "Gapped BLAST and PSI-BLAST: A New Generation of Protein Database Search Programs," Nucleic Acids Research, 1997, vol. 25, No. 17, pp. 3389-3402.
Ambler, "the structure of β-lactamases," Phil. Trans. R. Soc. Lond. B 289: 321-331 (1980).
Ambler et al., "A Standard Numbering Scheme for the Class A Beta-Lactamases," Biochem. J., 1991, 276, pp. 269-272.
Bonnet, "Growing Group of Extended-Spectrum β-Lactamases: the CTX-M Enzymes," Antimicrob. Agents Chemother. 48(1):1-14 (2004).
Bonomo et al., "β-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin®), Experimental and Clinical Study," International Journal of Clinical Pharmacology, Therapy and Toxicology, 1989, vol. 27, No. 3, pp. 135-144.
Broun et al., "Catalytic plasticity of fatty acid modification enzymes underlying chemical diversity of plant lipids," Science 1998, vol. 282: 1315-1317.
Bush, "Metallo-β-Lactamases: A Class Apart," Clinical Infectious Diseases, 1998; 27(Suppl 1):S48-53.
Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.
Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42(6):1323-1328 (1998).
Carfi et al., "1.85 Å Resolution Structure of the Zinc II β-Lactamase from Bacillus cereus," Acta Cryst. (1998) D54: 313-323.
Carfi et al., "X-ray Structure of the Zn11 β-Lactamase from Bacteroides fragilis in an Orthorhombic Crystal Form," Acta. Cryst. (1998) D54: 47-57.
Carfi et al., "The 3-D structure of a zinc metallo-β-lactamase from Bacillus cereus reveals a new type of protein fold," The EMBO Journal, 1995, vol. 14 No. 20: 4914-4921.
Chambliss, "The forgotten dosage form: enteric coated tablets," (1983) Pharm Technol 7, 124-140.
Chen et al.,"β-Lactamase Genes of the Penicillin-Susceptible Bacillus anthracis Sterne Strain," J. Bacteriol. 185(3):823-830 (2003).
Chica et al., "Semi-rational approaches to engineering enzyme activity: combining the benefits of directed evolution and rational design," Curr. Opin. Biotechnol., 2005, vol. 16: 378-384.
Cole, "Hydrolysis of Penicillins and Related Compounds by the Cell-Bound Penicillin Acylase of *Escherichia coli*," (1969) Biochem. J. 115, 733-739.
Colombo et al., "The ybxI Gene of Bacillus Subtilis 168 Encodes a Class D β-Lactamase of Low Activity," Antimicrobial Agents and Chemotherapy, Feb. 2004, vol. 48, No. 2, pp. 484-490.
Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.
Crawford, et al., "Over-expression, purification, and characterization of metallo-β-lactamase ImiS from Aeromonas veronii bv. sobria," Protein Expression and Purification 36 (2004) 272-279.
Davies and Abraham, "Separation, Purification and Properties of β-Lactamase I and β-Lactamase II from Bacillus cereus 569/H/9," (1974) Biochem. J. 143:115-127.
Delmas et al., "Structural Insights into Substrate Recognition and Product Expulsion in CTX-M Enzymes," J. Mol. Biol. 400:108-120 (2010).

(56) References Cited

OTHER PUBLICATIONS

Devos et al., "Practical limits of function prediction," Proteins: Structure, Function, and Genetics. 2000, vol. 41: 98-107.
Donskey, "Antibiotic Regimens and Intestinal Colonization with Antibiotic-Resistant Gram-Negative Bacilli," Clinical Infectious Diseases, 2006, 43 Suppl 2, pp. S62-S69.
Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).
Finnish Patent Search Report from Finnish Patent Office for FI 20065431, Oct. 24, 2007.
Galleni et al., "Standard Numbering Scheme for Class B β-Lactamases," Antimicrobial Agents and Chemotherapy, Mar. 2001, vol. 45, No. 3, pp. 660-663.
Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.
Garau et al., "A Metallo-β-lactamase Enzyme in Action: Crystal Structures of the Monozinc Carbapenemase CphA and its Complex with Biapenem," J. Mol. Biol. (2005) 345, 785-795.
Gazouli et al., "Effect of substitution of Asn for Arg-276 in the cefotaxime-hydrolyzing class A β-lactamase CTX-M-4," FEMS Microbiol. Lett. 168:289-293 (1998).
Gebhard et al., "Mapping the Distribution of Conformational Information Throughout a Protein Sequence," J. Mol. Biol., 2006, 358, pp. 280-288.
Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).
Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.
Harmoinen et al., "Enzymic Degradation of a β-Lactam Antibiotic, Ampicillin, in the Gut: A Novel Treatment Modality," Journal of Antimicrobial Chemotherapy, 2003,51, pp. 361-365.
Hata et al., "Substrate Deacylation Mechanisms of Serine-β-lactamases," Biol. Pharm. Bull. 29:2151-2159 (2006).
Herzberg, "Refined Crystal Structure of β-Lactamase from *Staphylococcus aureus* PC1 at 2.0 Å Resolution," J. Mol. Biol. 217:701-719 (1991).
Higgins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.
Hirschi A et al. "Campylobacter pylori, Gastritis and Ulcus pepticum," Wien. Klin. Wsch. 14:493-497 (1987).
Horton et al., "Engineering hybrid genes without the use of restriction enzymes: gene splicing by overlap extension," 1989, Gene 77:61-68 (1989).
Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.
Hyman, "Anaphylactic Shock After Therapy With Penicillinase," (1959) JAMA 169, 593-594.
Illing et al., "Use of integrational plasmid excision to identify cellular localization of gene expression during sporulation in Bacillus subtilis," J. Bacteriol. 172(12):6937-6941 (1990).
International Search Report, PCT appl. No. PCT/FI93/00016 (May 7, 1993).
International Search Report, PCT appl. No. PCT/FI02/00861 (Feb. 11, 2003).
International Search Report, PCT appl. No. PCT/FI2007/050372 (Oct. 24, 2007).
International Search Report mailed Mar. 3, 2008 for International Application No. PCT/FI2007/050627.
International Search Report, PCT appl. No. PCT/FI2011/050450 (Sep. 12, 2011).
Iserhard et al., "Epidemiology and Treatment of Gastric Campylobacter pylori Infection: more Questions than Answers," (1990) Hepato-Gastroenterol 37, 38-44.
Izui et al., "Large Exopenicillinase, Initial Extracellular Form Detected in Cultures of Bacillus licheniformis," Biochemistry, 1980, 19, pp. 1882-1886.
Kato et al., "Nucleotide Sequence of the β-Lactamase Gene of Alkalophilic *Bacillus* sp. Strain 170," J. Gen. Microbiol. 131:3317-3324 (1985).
Katz, "Probiotics for the Prevention of Antibiotic-associated Diarrhea and *Clostridium difficile* Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Bioi., 1991, 220, pp. 435-455.
Korhonen et al., "Milk Immunoglobulins and Complement Factors," British Journal of Nutrition, 2000, 84 Suppl 1, pp. S75-S80.
Kropp et al., "Metabolism of Thienamycin and Related Carbapenem Antibiotics by the Renal Dipeptidase, Dehydropeptidase-I," (1982) Antimicrob Agents Chemother 22, 62-70.
Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman.and Gilman's, the Pharmacological Basis of Therapeutics, 8th Edition. New York: Pergamon Press, 1065-1097.
Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Ragged N-termini and other Variants of Class A β-Lactamases Analysed by Chromatofocusing," Biochem. J., 1991, 273, pp. 503-510.
Matagne et al., "Catalytic properties of class A β-lactamases: efficiency and diversity," Biochem. J. 330:581-598 (1998).
Mentula et al., "Inhibition of ampicillin-induced emergence of resistance in intestinal coliforms by targeted recombinant β-lactamase," International Journal of Antimicrobial Agents, (2004)24:555-561.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.
Perez-Llarena et al., "Structure-function studies of arginine at position 276 in CTX-M β-lactamases," J. Antimicrob. Chemother. 61(4):792-797 (2008).

(56) References Cited

OTHER PUBLICATIONS

Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Pluckthun and Knowles, "The consequence of of stepwise deletions from the signal-processing site of β-lactamase," J. Biol.Chem., 1987, vol. 262 (9): 3951-3957.
Rauws et al., "Campylobacter pyloridis-Associated Chronic Active Antral Gastritis," (1988) Gastroenterol 94, 33-40.
Rauws and Tytgat, "Cure of duodenal ulcer associated with eradication of Helicobacter pylori," (1990) Lancet 335, 1233-1235.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, pp. 8.1-8.126. 2001.
Sande et al., "Chapter 44. Antimicrobial Agents," (1990) In: Goodman and Gilman's, the Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a *Staphylococcus aureus* β-lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., "The Effect of Cefixime on Bacterial Flora in the Intestinal Tracts of Healthy Male Volunteers," (1985) Chemotherapy (Tokyo) 33, Suppl. 6, 169-180.
Search Report from National Board of Patents and Registration of Finland—Corresponding Finnish Application No. 20065757 (May 28, 2007).
Search Report from National Board of Patents and Registration of Finland—Corresponding Finnish Application No. 20105572 (2010).
Sen et al., "Developments in directed evolution for improving enzyme functions," Appl. Biochem. Biotechnol., Aug. 18, 2007, vol. 143: 212-223.
Shimooka et al., "Absorption, Distribution, and Excretion of Sulbactam and Ampilcillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.
Sjolund et al., "Long-Term Persistence of Resistant *Enterococcus* Species after Antibiotics to Eradicate Helicobacter pylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Sullivan et al., "Effect of Antimicrobial Agents on the Ecological Balance of Human Microflora," Lancet Infect. Dis., 2001, vol. 1, pp. 101-114.
Supplementary EP Search Report relating to Corresponding EP 07765926.6, Mar. 4, 2010.
Tarkkanen et al., "P1A Recombinant β-Lactamase Prevents Emergence of Antimicrobial Resistance in Gut Microflora of Healthy Subjects during Intravenous Administration of Ampicillin," Antimicrob. Agents Chemother. 53:2455-2462 (2009).
Therapeutic Drugs (1991), Dollery C, ed. Edinburgh: Churchill Livingstone, "Ceftriaxone (sodium)," c 127-c133.
Tranier et al., "The High Resolution Crystal Structure for Class A β-Lactamase PER-1 Reveals the Bases for Its Increase in Breadth of Activity," J. Biol. Chem. 275:28075-28082 (2000).
Walsh et al., "Metallo-β-Lactamases: the Quiet before the Storm?" Clinical Microbiology Reviews (Apr. 2005) vol. 18 No. 2: 306-325.
Walther-Rasmussen et al., "Terminal truncations in Amp C β-lactamase from a clinical isolate of Pseudomonas aeruginosa," Eur. J. Biochem. (1999) 263: 478-485.
Westphal et al., "Assessment of Biliary Excretion of Piperacilin-Tazobactam in Humans," Antimicrobial Agents and Chemotherapy, Aug. 1997, vol. 41, No. 8, pp. 1636-1640.
Whisstock et al., "Prediction of protein function from protein sequence," Q. Rev. Biophysics., 2003, vol. 36 (3): 307-340.
Wildfeuer et al., "Pharmacokinetics of Sulbactam and Ampicillin Intravenously Applied in Combination to Healthy Volunteers and Patients", Arzneimittei-Forschung, 1988, vol. 38, No. 11, pp. 1640-1643.
Wishart et al., "A single mutation converts a novel phosphotyrosine binding domain into a dual-specificity phosphatase," J. Biol. Chem., 1995, vol. 270(45): 26782-26785.
Witkowski et al., "Conversion of β-ketoacyl synthase to a Malonyl Decarboxylase by replacement of the active cysteine with glutamine," Biochemistry, 1999, vol. 38: 11643-11650.
Knox, "Extended-spectrum and inhibitor-resistant TEM-Type β-lactamases: Mutations, Specificity, and Three-Dimensional Structure," Antimicrob. Agents Chemother., 1995, 39, 2593-2601.

* cited by examiner

Figure 7

| Group | Animals | Antibiotic | SYN-004 | C. difficile (2.6×10⁶ cfu) |
|---|---|---|---|---|
| 1 | Pig 2<br>Pig 9* | None | None | Yes |
| 2 | Pig 7<br>Pig 8** | Clindamycin<br>(50 mg/kg, IP) | None | Yes |
| 3 | Pig 5<br>Pig 6 | Ceftriaxone<br>(50 mg/kg, IP) | None | Yes |
| 4 | Pig 10<br>Pig 11<br>Pig 12 | Ceftriaxone<br>(50 mg/kg, IP) | 75 mg, QID<br>7am, 12 pm,<br>5 pm, 10 pm | Yes |

Top

Turicibacter sp
Bifidobacterium adolescentis
Bifidobacterium bifidum
Eggerthella sp
Lachnospiraceae bacterium
Flavonifractor plautii
Anaerostipes caccae
Clostridium nexile
Anaerostipes sp
Alistipes putredinis
Coprobacillus sp
Clostridium bolteae
Mollicutes bacterium
Escherichia coli
Alistipes sp
Ruminococcus gnavus
Alistipes shahii
Parabacteroides merdae
Bacteroides stercoris
Odoribacter splanchnicus
Bilophila wadsworthia Clostridium citroniae
Bacteroides thetaiotaomicron
Klebsiella pneumoniae
Clostridium symbiosum
Parabacteroides johnsonii
Ruminococcus torques
Bacteroides uniformis
Bacteroides dorei
Klebsiella variicola
Clostridium hathewayi
Bacteroides xylanisolvens
Eggerthella lenta
Clostridiales bacterium
Ruminococcaceae bacterium
Staphylococcus hominis
Actinobacteria Node
Parabacteroides sp
Clostridium ramosum
Gordonibacter pamelaeae
Clostridium clostridioforme
Bacteroides sp Klebsiella_pneumoniae_342
Roseburia sp
Streptococcus sp
Bilophila sp
Eubacterium limosum
Clostridium difficile
Clostridium sp
Enterococcus sp
Erysipelotrichaceae bacterium
Bifidobacterium longum
Parabacteroides distasonis
Streptococcus infantarius
Klebsiella sp
Veillonella sp
Streptococcus thermophilus
clostridiales Node
Streptococcus gallolyticus
Lactobacillus plantarum
Betaproteobacteria Node
Bifidobacterium sp
Lactobacillus fermentum Veillonella atypica
Enterococcus faecalis
Enterococcus gallinarum
Enterococcus saccharolyticus
Enterococcus faecium
Methanobrevibacter smithii Bottom

SEQUENCE LISTING

```
<160> NUMBER OF SEQ ID NOS: 6

<210> SEQ ID NO 1
<211> LENGTH: 264
<212> TYPE: PRT
<213> ORGANISM: Artificial Sequence
<220> FEATURE:
<223> OTHER INFORMATION: Synthetic sequence

<400> SEQUENCE: 1

Thr Glu Met Lys Asp Asp Phe Ala Lys Leu Glu Glu Gln Phe Asp Ala
1               5                   10                  15

Lys Leu Gly Ile Phe Ala Leu Asp Thr Gly Thr Asn Arg Thr Val Ala
            20                  25                  30

Tyr Arg Pro Asp Glu Arg Phe Ala Phe Ala Ser Thr Ile Lys Ala Leu
        35                  40                  45

Thr Val Gly Val Leu Leu Gln Gln Lys Ser Ile Glu Asp Leu Asn Gln
    50                  55                  60

Arg Ile Thr Tyr Thr Arg Asp Asp Leu Val Asn Tyr Asn Pro Ile Thr
65                  70                  75                  80

Glu Lys His Val Asp Thr Gly Met Thr Leu Lys Glu Leu Ala Asp Ala
                85                  90                  95

Ser Leu Arg Tyr Ser Asp Asn Ala Ala Gln Asn Leu Ile Leu Lys Gln
            100                 105                 110

Ile Gly Gly Pro Glu Ser Leu Lys Lys Glu Leu Arg Lys Ile Gly Asp
        115                 120                 125

Glu Val Thr Asn Pro Glu Arg Phe Glu Pro Glu Leu Asn Glu Val Asn
    130                 135                 140

Pro Gly Glu Thr Gln Asp Thr Ser Thr Ala Arg Ala Leu Val Thr Ser
145                 150                 155                 160

Leu Arg Ala Phe Ala Leu Glu Asp Lys Leu Pro Ser Glu Lys Arg Glu
                165                 170                 175
```

Leu Leu Ile Asp Trp Met Lys Arg Asn Thr Thr Gly Asp Ala Leu Ile
            180                 185                 190

Arg Ala Gly Val Pro Asp Gly Trp Glu Val Ala Asp Lys Thr Gly Ala
        195                 200                 205

Ala Ser Tyr Gly Thr Arg Asn Asp Ile Ala Ile Trp Pro Pro Lys
    210                 215                 220

Gly Asp Pro Val Val Leu Ala Val Leu Ser Ser Arg Asp Lys Asp
225                 230                 235                 240

Ala Lys Tyr Asp Asn Lys Leu Ile Ala Glu Ala Thr Lys Val Val Met
            245                 250                 255

Lys Ala Leu Asn Met Asn Gly Lys
            260

<210> SEQ ID NO 2
<211> LENGTH: 795
<212> TYPE: DNA
<213> ORGANISM: Artificial Sequence
<220> FEATURE:
<223> OTHER INFORMATION: Synthetic sequence

<400> SEQUENCE: 2
atgactgaga tgaaagatga ttttgcgaag ctggaagaac agtttgacgc aaaattgggc    60
attttcgcgt tggacacggg tacgaatcgt acggttgcct accgtccgga cgagcgcttc   120
gccttcgcga gcacgatcaa agccctgacc gtcggcgtgc tgctccagca aaagagcatc   180
gaggacctga accagcgcat tacctacacc cgtgatgatc tggtgaacta taatccgatc   240
accgagaaac acgttgatac cggtatgacc ctgaaagaac tggcagatgc aagcctgcgc   300
tacagcgata acgcggctca gaatctgatt ctgaagcaaa tcggtggtcc ggagagcttg   360
aagaaagaac tgcgtaaaat cggcgatgaa gtcactaatc cggagcgttt tgagccggag   420
ctgaacgaag tgaatccggg tgaaacgcaa gacacgagca ccgcgcgtgc gcttgtcacc   480
tccctgcgcg ctttcgcact ggaagataag ctgccgtcgg agaaacgcga gctgctgatc   540
gactggatga gcgcaatac gaccggcgac gcgctgattc gtgcgggcgt tccggacggt   600
tgggaagtgg ctgacaagac cggtgcggcg agctacggca cccgtaacga tatcgcgatc   660
atttggccac ctaaaggtga cccggtcgtg ctggccgtac tgagcagccg tgacaagaaa   720
gacgcaaagt atgataacaa gctgattgca gaggcgacca agttgttat gaaggcactg   780 aacatgaatg gtaag                                                   795

<210> SEQ ID NO 3
<211> LENGTH: 262
<212> TYPE: PRT
<213> ORGANISM: Artificial Sequence
<220> FEATURE:
<223> OTHER INFORMATION: Synthetic sequence

<400> SEQUENCE: 3

Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

```
Ile Thr Thr Arg Asp Asp Leu Val Asn Tyr Asn Pro Ile Thr Glu Lys
 65                  70                  75                  80

His Val Asp Thr Gly Met Thr Leu Lys Glu Leu Ala Asp Ala Ser Leu
                 85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
        115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Val Pro Asp Gly Trp Glu Val Gly Asp Lys Thr Gly Ser Gly Asp
        195                 200                 205

Tyr Gly Thr Arg Asn Asp Ile Ala Ile Ile Trp Pro Pro Lys Gly Asp
    210                 215                 220

Pro Val Leu Ala Val Leu Ser Ser Arg Asp Lys Lys Asp Ala Lys
225                 230                 235                 240

Tyr Asp Asn Lys Leu Ile Ala Glu Ala Thr Lys Val Val Met Lys Ala
                245                 250                 255

Leu Asn Met Asn Gly Lys
            260

<210> SEQ ID NO 4
<211> LENGTH: 299
<212> TYPE: PRT
<213> ORGANISM: Artificial Sequence
<220> FEATURE:
<223> OTHER INFORMATION: Synthetic sequence

<400> SEQUENCE: 4

Met Ile Gln Lys Arg Lys Arg Thr Val Ser Phe Arg Leu Val Leu Met
1                5                  10                  15

Cys Thr Leu Leu Phe Val Ser Leu Pro Ile Thr Lys Thr Ser Ala Gln
                20                  25                  30

Ala Ser Lys Thr Glu Met Lys Asp Asp Phe Ala Lys Leu Glu Glu Gln
            35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
 65                 70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160
```

```
Ile Gly Asp Glu Val Thr Asn Pro Glu Arg Phe Glu Pro Glu Leu Asn
            165                 170                 175

Glu Val Asn Pro Gly Glu Thr Gln Asp Thr Ser Thr Ala Arg Ala Leu
        180                 185                 190

Val Thr Ser Leu Arg Ala Phe Ala Leu Glu Asp Lys Leu Pro Ser Glu
        195                 200                 205

Lys Arg Glu Leu Leu Ile Asp Trp Met Lys Arg Asn Thr Thr Gly Asp
210                 215                 220

Ala Leu Ile Arg Ala Gly Val Pro Asp Gly Trp Glu Val Gly Asp Lys
225                 230                 235                 240

Thr Gly Ser Gly Asp Tyr Gly Thr Arg Asn Asp Ile Ala Ile Ile Trp
            245                 250                 255

Pro Pro Lys Gly Asp Pro Val Val Leu Ala Val Leu Ser Ser Arg Asp
        260                 265                 270

Lys Lys Asp Ala Lys Tyr Asp Asn Lys Leu Ile Ala Glu Ala Thr Lys
        275                 280                 285

Val Val Met Lys Ala Leu Asn Met Asn Gly Lys
        290                 295
```

<210> SEQ ID NO 5
<211> LENGTH: 900
<212> TYPE: DNA
<213> ORGANISM: Artificial Sequence
<220> FEATURE:
<223> OTHER INFORMATION: Synthetic sequence

<400> SEQUENCE: 5

```
atgattcaaa aacgaaagcg acagtttcg ttcagacttg tgcttatgtg cacgctgtta      60
tttgtcagtt tgccgattac aaaaacatca gcgcaagctt ccaagacgga gatgaaagat    120
gattttgcaa aacttgagga acaatttgat gcaaaactcg ggatctttgc attggataca    180
ggtacaaacc ggacggtagc gtatcggccg gatgagcgtt ttgcttttgc ttcgacgatt    240
aaggctttaa ctgtaggcgt gcttttgcaa cagaaatcaa tagaagatct gaaccagaga    300
ataacatata cacgtgatga tcttgtaaac tacaacccga ttacggaaaa gcacgttgat    360
acgggaatga cgctcaaaga gcttgcggat gcttcgcttc gatatagtga caatgcggca    420
cagaatctca ttcttaaaca aattggcgga cctgaaagtt tgaaaaagga actgaggaag    480
attggtgatg aggttacaaa tcccgaacga ttcgaaccag agttaaatga agtgaatccg    540
ggtgaaactc aggataccag tacagcaaga gcacttgtca caagccttcg agcctttgct    600
cttgaagata aacttccaag tgaaaaacgc gagcttttaa tcgattggat gaaacgaaat    660
accactggag acgccttaat ccgtgccggt gtgccggacg gttgggaagt gggtgataaa    720
actggaagcg gagattatgg aacccggaat gacattgcca tcatttggcc gccaaaagga    780
gatcctgtcg ttcttgcagt attatccagc agggataaaa aggacgccaa gtatgataat    840
aaacttattg cagaggcaac aaaggtggta atgaaagcct taaacatgaa cggcaaataa    900
```

<210> SEQ ID NO 6
<211> LENGTH: 216
<212> TYPE: PRT
<213> ORGANISM: Artificial Sequence
<220> FEATURE:
<223> OTHER INFORMATION: Synthetic sequence

<400> SEQUENCE: 6

```
Glu Thr Gly Thr Ile Ser Ile Ser Gln Leu Asn Lys Asn Val Trp Val
1               5                   10                  15
```

```
His Thr Glu Leu Gly Tyr Phe Asn Gly Glu Ala Val Pro Ser Asn Gly
            20                  25                  30

Leu Val Leu Asn Thr Ser Lys Gly Leu Val Leu Val Asp Ser Ser Trp
            35                  40                  45

Asp Asn Lys Leu Thr Lys Glu Leu Ile Glu Met Val Glu Lys Lys Phe
        50                  55                  60

Gln Lys Arg Val Thr Asp Val Ile Ile Thr His Ala His Ala Asp Arg
65                  70                  75                  80

Ile Gly Gly Ile Thr Ala Leu Lys Glu Arg Gly Ile Lys Ala His Ser
                85                  90                  95

Thr Ala Leu Thr Ala Glu Leu Ala Lys Asn Ser Gly Tyr Glu Glu Pro
                100                 105                 110

Leu Gly Asp Leu Gln Thr Ile Thr Ser Leu Lys Phe Gly Asn Thr Lys
            115                 120                 125

Val Glu Thr Phe Tyr Pro Gly Lys Gly His Thr Glu Asp Asn Ile Val
        130                 135                 140

Val Trp Leu Pro Gln Tyr Gln Ile Leu Ala Gly Gly Cys Leu Val Lys
145                 150                 155                 160

Ser Ala Glu Ala Lys Asp Leu Gly Asn Val Ala Asp Ala Tyr Val Asn
                165                 170                 175

Glu Trp Ser Thr Ser Ile Glu Asn Val Leu Lys Arg Tyr Gly Asn Ile
            180                 185                 190

Asn Ser Val Val Pro Gly His Gly Glu Val Gly Asp Lys Gly Leu Leu
        195                 200                 205

Leu His Thr Leu Asp Leu Leu Lys
210                 215
```

BETA-LACTAMASE FORMULATIONS AND USES THEREOF

CROSS-REFERENCE TO RELATED APPLICATIONS

This application is a continuation of U.S. patent application Ser. No. 16/111,477 (now U.S. Pat. No. 10,828,260), which is a continuation application of U.S. patent application Ser. No. 14/878,155 (now U.S. U.S. Pat. No. 10,105,322), filed Oct. 8, 2015, which claims the benefit of U.S. Provisional Patent Application No. 62/061,507, filed Oct. 8, 2014; U.S. Provisional Patent Application No. 62/126,556, filed Feb. 28, 2015; and U.S. Provisional Patent Application No. 62/205,443, filed Aug. 14, 2015, the entire contents of all of which are herein incorporated by reference.

FIELD OF THE INVENTION

The present invention provides, in part, pharmaceutical dosage forms comprising beta-lactamases and uses thereof.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: SYN-007-SequenceListing.txt; date recorded: Oct. 6, 2015; file size: 12 KB).

BACKGROUND

Beta-lactam antibiotics are characterized by a beta-lactam ring in their molecular structure. The integrity of the beta-lectern ring is essential for biological activity, which results in the inactivation of a set of transpeptidases that catalyze the final cross-linking reactions of peptidoglycan synthesis. Members of the beta-lactam antibiotics family include penicillins, cephalosporins, clavams (or oxapenams), cephamycins and carbapenems.

Beta-lactamases are bacterial defensive enzymes that hydrolyze beta-lactam antibiotics. Gram-negative bacteria produce beta-lactamases to achieve resistance to beta-lactam antibiotics. Particularly, beta-lactamases are able to efficiently catalyze the irreversible hydrolysis of the amide bond of the beta-lactam ring resulting in biologically inactive product(s).

Humans may be considered to be a "superorganism" which is a conglomerate of mammalian and microbial cells, with the latter estimated to outnumber the former by ten to one. This microbial component, and its microbial genetic repertoire, the microbiome, is roughly 100-times greater than that of the human host. Strikingly, despite this enormous diversity of foreign organisms, the human immune system generally maintains a state of synergy. This is particularly true of the distal gastrointestinal (GI) tract, which houses up to 1000 distinct bacterial species and an estimated excess of $1 \times 10^{14}$ microorganisms, and appears to be central in defining human host health status. Loss of the careful balance in the microbiome, especially in the GI tract, can lead to various diseases.

Nevertheless, antibiotic medical treatments, which are needed to treat certain aspects of disease, can induce disruption in the microbiome, including in the GI tract, and lead to further disease. For instance, certain parentally administered beta-lactams like ampicillin, ceftriaxone, cefoperazone, and piperacillin are, in part, eliminated via biliary excretion into the proximal part of the small intestine (duodenum). Residual unabsorbed beta-lactams in the GI tract may cause an undesirable effect on the ecological balance of normal intestinal microbiota resulting in, for example, *Clostridium difficile* infection (CDI), antibiotic-associated diarrhea, overgrowth of pathogenic bacteria such as vancomycin resistant enterococci (VRE), extended-spectrum beta-lactamase producing Gram-negative bacilli (ESBL), and fungi, and selection of antibiotic-resistant strains among both normal intestinal microbiota and potential pathogenic bacteria.

One approach for avoiding or rebalancing the ecological balance of normal intestinal microbiota is the therapeutic use of beta-lactamases, for example, by inactivating excreted or unabsorbed antibiotics in the GI tract, thereby maintaining a normal intestinal microbiota and preventing its overgrowth with potentially pathogenic micro-organisms.

Accordingly, there is remains a need for improved beta-lactamase formulations for use in therapeutic intervention.

SUMMARY OF THE INVENTION

Accordingly, the present invention provides modified-release formulations comprising a beta-lactamase (e.g. "P3A", as shown in SEQ ID NO: 1 or 2, or variants thereof) and/or additional therapeutic agents. In various embodiments, the formulations release a substantial amount of the beta-lactamase in the GI tract. In one embodiment, the formulation comprises at least one core particle and a base coat over the core particle, wherein the base coat comprises a beta-lactamase. In another embodiment, the formulation comprises at least one core particle, wherein the beta-lactamase is encapsulated within the core particle. In various embodiments, the formulation comprises a modified-release coating such as a delayed-release coating disposed over the core particle. In some embodiments, the delayed-release coating is substantially stable in gastric fluid. In an embodiment, the delayed-release coating comprises a Eudragit compound. In various embodiments; the formulation may be in the form of a capsule or a tablet. In some embodiments, the capsule or tablet includes a plurality of core particles.

These improved beta-lactamases find uses in a number of therapies, including the prevention or treatment of CDI and/or a *C. difficile*-associated disease or other antibiotic-induced adverse effects in the GI tract. For example, the beta-lactamases find use in allowing a patient to undergo antibiotic therapy while being protected against diseases that could result from excess antibiotics negatively affecting the microbiome. Such use does not interfere with the systemic utility of the antibiotic. Rather, the beta-lactamases remove excess antibiotic that may populate parts of the GI tract and, in doing so, prevent the disruption of the microbiota that is linked to the various disease states described herein.

In some aspects, the present invention provides a method for preventing *C. difficile* infection (CDI) and/or a *C. difficile*-associated disease, comprising administering an effective amount of a modified-release formulation of any one of the above-claims to a patient that is undergoing therapy with a primary antibiotic, such as one or more of a ceftriaxone, cefotaxime, cefazolin, cefoperazone, cefuroxime, and piperacillin, and the primary antibiotic is administered intravenously.

DESCRIPTION OF THE FIGURES

The patent or application file contains at least one drawing executed in color. Copies of this patent or patent application publication with color drawing(s) will be provided by the Office upon request and payment of the necessary fee.

FIG. 7 shows the design of a pig study for evaluating P3A mediated microbiome protection. "*" indicates that Pig 9 was sickly and did not gain weight. "**" indicates that Pig 8 was moribund and euthanized on Day 14, after *C. difficile* administration. CDI was not confirmed. Other than Pigs 8 and 9, no other animals got sick. CDI was not confirmed in any animal, including Pig 8, via *C. difficile* Toxin A or IL8 ELISAs, or via intestinal tract histological analyses.

FIG. 10A shows photographs of the LB+amp plates. FIG. 10B shows the quantification of the bacterial colonies on each plate. Equal quantities of diluted feces collected from animals at necropsy were plated on LB+amp plates and grown under aerobic conditions at 37° C., The colonies were counted while taking into account the dilution factor.

FIG. 11B lists the bacterial strains from right to left of the heatmap. For example, the rightmost bacterial taxa depicted on the heatmap is Bacteroides_318 Node.

FIGS. 13A and 13B provide a comparative metagenomic analyses using centroid classification to compare the average deviation of the frequency of each bacterial strain within each study group from the overall average frequency of all the study groups. FIG. 13B lists the bacterial strains from top to bottom of the graph. For example, the topmost bacterial strain depicted on the graph is Streptococcus_infantarius_subso_infantarius_ATCC_BAA-102.

FIG. 14B lists the bacterial strains from top to bottom of the graph. For example, the topmost bacterial strain depicted on the graph is *Streptococcus infantarius*.

FIGS. 15A and 15B shows species-level centroid classification of sample subsets to compare the average deviation of the frequency of each bacterial species in Group 3 (Ceftriaxone) and Group 4 (Ceftriaxone plus P3A) to Group 1 (Control). The boxes on the top and bottom of portion of the figure highlight the reduction in the abundance of *Turicibacter* spp, a species associated with idiopathic inflammatory bowel disease and acute hemorrhagic diarrhea in dogs (Minamoto et al., 2015, Gut Microbes 6(1), 33-47; Rossi et al., 2014, PLoS ONE 9(4), e94699), and the overabundance of the methanogenic archaea, *Methanobrevibacter smithii*, a species reported to be linked to constipation, irritable bowel syndrome, and obesity (Pimentel et al., 2002, Am, J. Gastroenter. Supple. 1:28). FIG. 15B lists the bacterial species from top to bottom of the graph. For example, the topmost species depicted on the graph is *Turicibacter sp*.

FIG. 16B lists the bacterial species and strains from top to bottom of the graph. For example, the topmost species or strain depicted on the graph is *Streptococcus infantarius*.

DETAILED DESCRIPTION OF THE INVENTION

Beta-Lactamases

Figure 1A:
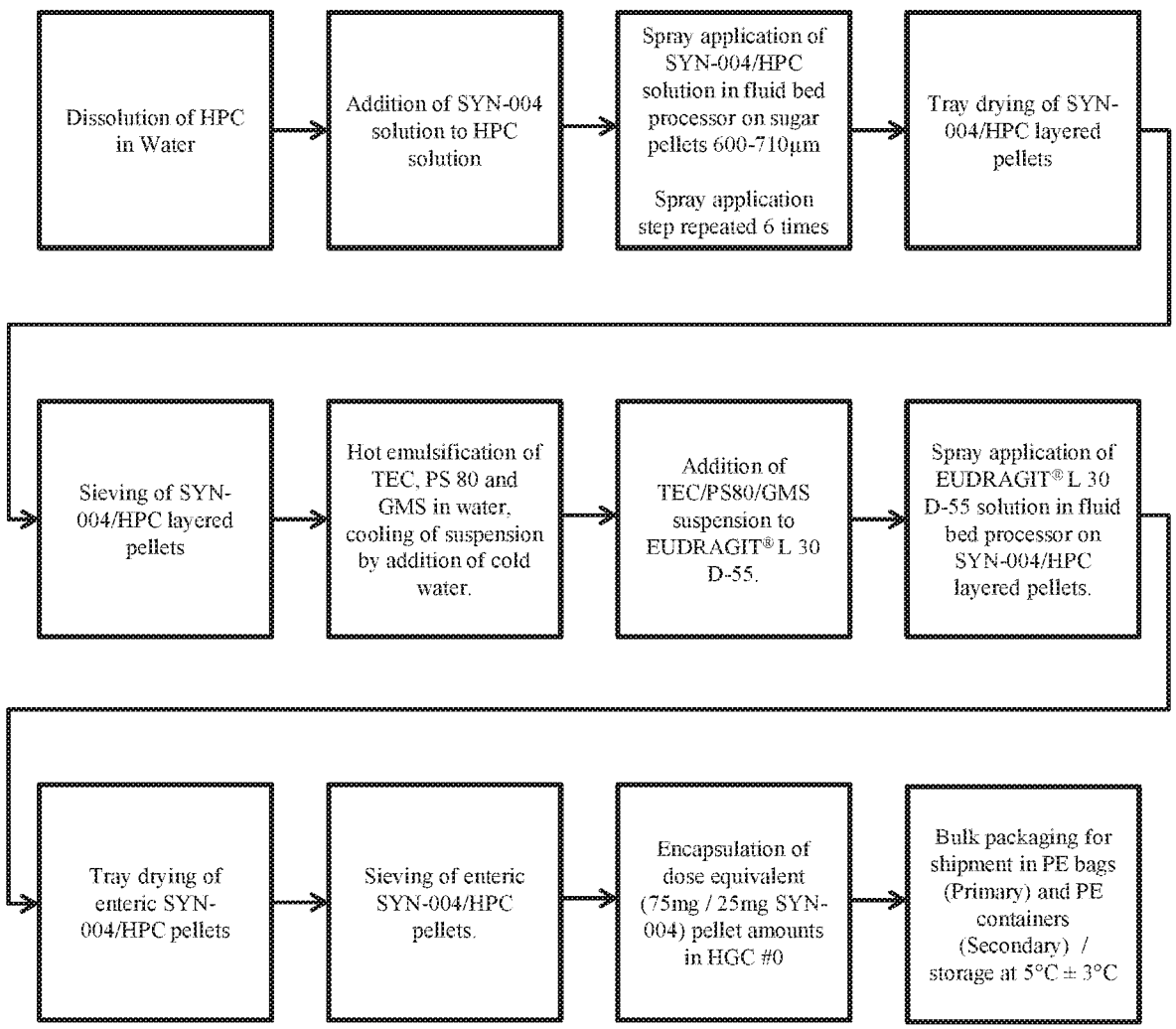
FIG. 1A depicts an embodiment of a manufacturing process for producing P3A delayed-release capsules.

In some aspects, the present invention is directed to compositions and formulations and uses of one or more beta-lactamases. As used herein, a beta-lactamase refers to an enzyme, which hydrolyzes beta-lactams. Hydrolysis of the amide bond of the beta-lactam ring makes the antimicrobial agents biologically inactive. As used herein, class A beta-lactamases (Ambler classification) refer to serine beta-lactamases, in which hydrolysis of beta-lactam is mediated by serine in the active site, usually at amino acid position 70 in the alpha helix$_2$. Class A beta-lactamases include but are not limited to Len-1, SHV-1, TEM-1, PSE-3/PSE-3, ROB-1, *Bacillus cereus* such as 5/B type 1, 569/H type 1 and 569/H type 3, *Bacillus anthrasis* sp, *Bacillus licheniformis* such as PenP, *Bacillus weihenstephanensis, Bacillus clausii, Staphylococcus aureus*, PC1, Sme-1 NmcA, IMI-, PER-, VEB-, GES-, KPC-, CME- and CTX-M types beta-lactamases.

In various aspects, the beta-lactamases has the amino acid sequence of SEQ ID NO: 1 (i.e., "P3A" as described in WO2011/148041, the entire contents of which are hereby incorporated by reference). Mutations may be made to this sequence to generate beta-lactamase derivatives that may be utilized by methods of the invention.

```
                                          SEQ ID NO: 1
TEMKDDFAKLEEQFDAKLGIFALDTGTNRTVAYRPDERFAFASTIKALI

TVGVLLQCKSIEDLNQRITYTRDDLVNYNPITEKHVDTGMTLKELADAS
```

-continued
```
LRYSDNAAQNLILKQIGGPESLKKELRKIGDEVTNPERFEPELNEVNPG

ETQDTSTARALVTSLRAFALEDKLPSEKRELLIDWMKRNTTGDALIRAG

VPDGWEVADKTGAASYGTRNDIAIIWPPKGDPVVLAVLSSRDKKDAKYD

NKLIAEATKVVMKALNMNGK.
```

In some embodiments, the beta-lactamase comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1.

In some embodiments, SEQ ID NO: 1 may have a Met and/or Thr preceding the first residue of the sequence. In various embodiments, the Met may be cleaved. As described herein, mutations may be made to the sequence comprising the Met and/or Thr preceding the first residue to generate beta-lactamase derivatives. In some embodiments, the leading Thr may bring about increased stability of the enzyme relative to another leading amino acid (e.g. Lys). For example, such a residue may confer increased resistance to an amino peptidase.

Also provided herein is the nucleotide sequence of the P3A as SEQ ID NO: 2:

```
                                          SEQ ID NO: 2
atgactgagatgaaagatgattttgcgaagctggaagaacagtttgacg caaaattgggcattttcgcgttggacacgggtacgaatcgtacggttgc ctaccgtccggacgagcgctcgccttcgcgagcacgatcaaagccctga ccgtcggcgtgctgctccagcaaaagagcatcgaggacctgaaccagcg cattacctacaccgtgatgatctggtgaactataatccgatcaccgag aaacacgttgataccggtatgaccctgaaagaactggcagatgcaagcc tgcgctacagcgataacgcggctcagaatctgattctgaagcaaatcgg tggtccggagagcttgaagaaagaactgcgtaaaatcggcgatgaagtc actaatccggagcgttttgagccggagctgaacgaagtgaatccgggtg aaacgcaagacacgagcaccgcgcgtgcgcttgtcacctccctgcgcgc tttcgcactggaagataagctgccgtcggagaaacgcgagctgctgatc gactggatgaagcgcaatacgaccggcgacgcgctgaatcgtgcgggcg ttccggacggttgggaagtggctgacaagaccggtcggcgagctacgg cacccgtaacgatatcgcgatcatttggccacctaaaggtgacccggtc gtgctggccgtactgagcagccgtgacaagaaagacgcaaagtatgata acaagctgattgcagaggcgaccaaagttgttatgaaggcactgaacat gaatggtaag
```

In some embodiments, a polynucleotide of the invention may have at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 2.

In some embodiments, the beta-lactamase, e.g. P3A, has substantial ceftriaxone hydrolyzing activity. In some embodiments, the beta-lactamase, e.g. P3A, hydrolyzes ceftriaxone substantially more efficiently than P1A.

In illustrative embodiments, the beta-lactamases comprise an amino acid sequence having at least 60% sequence identity with SEQ ID NO: 1 and the following of Ambler classification: a hydrophobic residue other than alanine (A) at position 232; a hydrophilic residue other than alanine (A) at position 237; a hydrophobic residue other than alanine (A) at position 238; a hydrophilic residue other than serine (5) at position 240; and a hydrophilic residue other than aspartate (D) at position 276. In some embodiments, the hydrophobic residue other than alanine (A) at position 232 is glycine (G). In some embodiments, the hydrophilic residue other than alanine (A) at position 237 is serine (5). In some embodiments, the hydrophobic residue other than alanine (A) at position 238 is glycine (G). In some embodiments, the hydrophilic residue other than serine (5) at position 240 is aspartate (D). In some embodiments, the other than aspartate (D) at position 276 is asparagine (N). In some embodiments, the beta-lactamase comprises one or more of A232G, A237S, A238G, S240D, and D276N. In some embodiments, the beta-lactamase comprises all of A232G, A237S, A238G, 5240D, and D276N, the sequence of which is SEQ ID NO: 3, i.e. P4A. In some embodiments, the beta-lactamase and/or pharmaceutical composition comprises an amino acid sequence having at least 90%, or 95%, or 97%, or 99%, or 100% sequence identity with SEQ ID NO: 3.

```
                                           SEQ ID NO: 3
EMKDDFAKLEEQFDAKLGIFALDTGTNRTVAYRPDERFAFASTIKALTVG

VLLQQKSIEDLNQRITTRDDLVNYNPITEKHVDTGMTLKELADASLRYSD

NAAQNLILKQIGGPESLKKELRKIGDEVTNPERFEPELNEVNPGETQDTS

TARALVTSLRAFALEDKLPSEKRELLIDWMKRNTTGDALIRAGVPDGWEV

GDKTGSGDYGTRNDIAIIWPPKGDPVVLAVLSSRDKKDAKYDNKLIAEAT

KVVMKALNMNGK
```

In some embodiments, the beta-lactamase polypeptide of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 3.

SEQ ID NO: 4, is derived from SEQ ID NO: 3, and further includes the signal and the addition of the QASKT amino acids (the coding region is underlined):

```
MIQKRKRTVSFRLVLMCTLLFVSLPITKTSAQASKTEMKDDFAKLEEQF

DAKLGIFALDTGTNRTVAYRPDERFAFASTIKALTVGVLLQQKSIEDLN

QRITYTRDDLVNYNPITEKHVDTGMTLKELADASLRYSDNAAQNLILKQ

IGGPESLKKELRKIGDEVTNPERFEPELNEVNPGETQDTSTARALVTSL

RAFALEDKLPSEKRELLIDWMKRNTTGDALIRAGVPDGWEVGDKTGSGD

YGTRNDIAIIWPPKGDPVVLAVLSSRDKKDAKYDNKLIAEATKVVMKAL

NMNGK
```

In some embodiments, the beta-lactamase polypeptide of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 4.

In some embodiments, the beta-lactamase and/or pharmaceutical composition comprises an amino acid sequence having at least 90%, or 95%, or 97%, or 99%, or 100% sequence identity with SEQ ID NO: 4.

An illustrative polynucleotide of the invention is SEQ ID NO: 5, which is the full nucleotide sequence of A232G, A237S, A238G, S2400, and D276N mutant, Hind III site (AAGCTT-in bold) and additional K and T amino acids. In some embodiments, the underlined portion of SEQ ID NO: 5, is omitted. The leader and additional nucleotides (Hind III site and K and T amino acids—for the addition of the amino acid sequence QASKT) are underlined.

```
atgattcaaaaacgaaagcggacagtttcgttcagacttgtgcttatgt gcacgctgttatttgtcagtttgccgattacaaaaacatcagcgcaagc ttccaagacggagatgaaagatgattttgcaaaacttgaggaacaattt gatgcaaaactcgggatctttgcattggatacaggtacaaaccggacgg tagcgtatcggccggatgagcgttttgcttttgcttcgacgattaaggc tttaactgtaggcgtgcttttgcaacagaaatcaatagaagatctgaac cagagaataacatatacacgtgatgatcttgtaaactacaacccgatta cggaaaagcacgttgatacgggaatgacgctcaaagagcttgcggatgc ttcgcttcgatatagtgacaatgcggcacagaatctcattcttaaacaa attggcggacctgaaagtttgaaaaaggaactgaggaagattggtgatg aggttacaaatcccgaacgattcgaaccagagttaaatgaagtgaatcc gggtgaaactcaggataccagtacagcaagagcacttgtcacaagcctt cgagcctttgctcttgaagataaacttccaagtgaaaaacgcgagcttt taatcgattggatgaaacgaaataccactggagacgccttaatccgtgc cggtgtgccggacggttgggaagtgggtgataaaactggaagcggagat tatggaacccggaatgacattgccatcatttggccgccaaaaggagatc ctgtcgttcttgcagtattatcccagcagggataaaaaggacgccaagt
```

-continued

```
atgataataaacttattgcagaggcaacaaaggtggtaatgaaagcctt aaacatgaacggcaaataa
```

In some embodiments, the polynucleotide of the present invention has at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 5 (with or without the underlined portion).

In various aspects, the beta-lactamases polypeptide has the sequence of SEQ ID NO: 6 (i.e., P2A) or is derived by one or more mutations of SEQ ID NO: 6:

```
ETGTISISQLNKNVWVHTELGYFNGEAVPSNGLVLNTSKGLVLVDSSWDN

KLTKELIEMVEKKFQKRVTDVIITHAHADRIGGITALKERGIKAHSTALT

AELAKNSGYEEPLGDLQTITSLKFGNTKVETFYPGKGHTEDNIVVWLPQY

QILAGGCLVKSAEAKDLGNVADAYVNEWSTSIENVLKRYGNINSVVPGHG

EVGDKGLLLHTLDLLK.
```

In some embodiments, the beta-lactamase polypeptide of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 6.

In some embodiments, the beta-lactamase and/or pharmaceutical composition comprises an amino acid sequence having at least 90%, or 95%, or 97%, or 99%, or 100% sequence identity with SEQ ID NO: 6.

Additional sequences of beta-lactamases including MA SEQ ID NO: 1 except position 276 is D and not N), P2A, P3A, and P4A and derivatives thereof are described for example, in WO 2011/148041 and PCT/US2015/026457, the entire contents of which are hereby incorporated by reference.

Further, the beta-lactamase polypeptide may include additional upstream residues from the first residue of SEQ ID NO: 1 (see, e.g., *JBC* 258 (18): 11211, 1983, the contents of which are hereby incorporated by reference-including the exo-large and exo-small versions of penP and penP1). Further, the beta-lactamase polypeptide may also include additional downstream residues from the last residue of SEQ ID NO: 1.

In some embodiments, the beta-lactamase includes one or more (e.g. about 1, or about 2, or about 3, or about 4, or about 5, or about 6, or about 7, or about 8, or about 9, or about 10) mutations relative to SEQ ID NO: 1 or SEQ ID NO: 2. In some embodiments the beta-lactamase includes a variant of P3A, e.g. a sequence with at least 95, 96, 97, 98, 99, 99.5, 99.8, 99.9% identity to SEQ ID NO: 1 or SEQ ID NO: 2. In various embodiments, one or more amino acid of SEQ ID NO: 1 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (5), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine 3-alanine, GABA and 6-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, βi-alanine, fluoro-amino acids, designer amino acids such as 3 methyl amino acids, Cα-methyl amino acids, N α-methyl amino acids, and amino acid analogs in general). In some embodiments, SEQ ID NO: 1 may have a Met and/or Thr preceding the first residue of the sequence. These residues may be similarly mutated as above.

Illustrative mutants include:

| Mutations relative to P1A (based on the Ambler classification) | Name |
|---|---|
| Wild type | RS310 (or P1A) |
| D276N | IS118 (or P3A) |
| I72S | IS222 |
| T160F | IS203 |
| R244T | IS217 |
| R244T D276K | IS215 |
| Q135M | IS197 |
| G156R A238T | IS235 |
| F33Y D276N | IS158 |
| F33Y S240P D276N | IS230 (or IS181) |
| F33Y A238T D276N | IS232 (or IS180) |
| I72S Q135M T160F (Block 1 mutants) | IS227 |
| A232G A237S A238G S240D (Block 2 mutants) | IS191 |
| A232G A237S A238G S240D R244T | IS229 |
| A232G A237S A238G S240D D276R | IS219 |
| A232G A237S A238G S240D D276K | IS221 |
| A232G A237S A238G S240D Q135M | IS224 |
| A238T | IS233 |
| T243I S266N D276N | IS234 (or IS176) |
| A232G A237S A238G S240D D276N | IS288 (or P4A) |

In all of these mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All).

In various embodiments, the beta-lactamase used in the invention is produced in bacterial cells such as an *E. coli* cell (see, e.g., PCT/US15/47187, the entire contents of which are hereby incorporated by reference).

Modified Release Profile

In one aspect, the present invention provides modified release formulations comprising at least one beta-lactamase, wherein the formulation releases a substantial amount of the beta-lactamase into one or more regions of the GI tract. In some embodiments, the beta-lactamase is P3A, or the other beta-lactamase agents described herein, and variants thereof (e.g. as described above). For example, the formulation may release at least about 60% of the beta-lactamase, for example, P3A, after the stomach and into one or more regions of the GI tract.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified-release formulation of the present invention releases at least 60% of the beta-lactamase (e.g. P3A, or the other beta-lactamase agents described herein, and variants thereof) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the intestine.

In various embodiments, the modified-release formulation of the present invention releases at least 60% of the beta-lactamase (e.g. P3A, or the other beta-lactamase agents described herein, and variants thereof) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the small intestine.

In one embodiment, the modified-release formulation of the present invention releases at least 60% of the beta-lactamase (e.g. P3A, or the other beta-lactamase agents described herein, and variants thereof) in the duodenum. For example, the modified-release formulation releases at least 60%, at least 61%, at least 62%, at least 63%, at least 64%, at least 65%, at least 66%, at least 67%, at least 68%, at least 69%, at least 701%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the duodenum.

In one embodiment, the modified-release formulation of the present invention releases at least 60% of the beta-lactamase (e.g. P3A, or the other beta-lactamase agents described herein, and variants thereof) in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the jejunum.

In one embodiment, the modified-release formulation of the present invention releases at least 60% of the beta-lactamase (e.g. P3A, or the other beta-lactamase agents described herein, and variants thereof) in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the ileum and/or the ileocecal junction.

In various embodiments, the modified-release formulation of the present invention releases at least 60% of the beta-lactamase (e.g. P3A, or the other beta-lactamase agents described herein, and variants thereof) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the large intestine.

In one embodiment, the modified-release formulation of the present invention releases at least 60% of the beta-lactamase (e.g. P3A, or the other beta-lactamase agents described herein, and variants thereof) in the cecum: For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the mourn.

In one embodiment, the modified-release formulation of the present invention releases at least 60% of the beta-lactamase (e.g. P3A, or the other beta-lactamase agents described herein, and variants thereof) in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the ascending colon.

In one embodiment, the modified-release formulation of the present invention releases at least 60% of the beta-lactamase (e.g. P3A, or the other beta-lactamase agents described herein, and variants thereof) in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the transverse colon.

In one embodiment, the modified-release formulation of the present invention releases at least 60% of the beta-lactamase (e.g. P3A, or the other beta-lactamase agents described herein, and variants thereof) in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the descending colon.

In one embodiment, the modified-release formulation of the present invention releases at least 60% of the beta-lactamase (e.g. P3A, or the other beta-lactamase agents described herein, and variants thereof) in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least %, at least 89%, at least 90%, at least 91%, at least 92%, at least 93%, at least 94%, at least 95%, at least 96%, at least 97%, at least 98%, at least 99%, or 100% of the beta-lactamase (e.g. P3A, or the other beta-lactamase agents described herein, and variants thereof) in the sigmoid colon.

In various embodiments, the modified-release formulation does not substantially release the beta-lactamase (e.g. P3A, or the other beta-lactamase agents described herein, and variants thereof) in the stomach.

In certain embodiments, the modified-release formulation releases the beta-lactamase (e.g. P3A, or the other beta-lactamase agents described herein, and variants thereof) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g.

one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the beta-lactamase (e.g. P3A, or the other beta-lactamase agents described herein, and variants thereof) and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the beta-lactamase (e.g. P3A, or the other beta-lactamase agents described herein, and variants thereof) and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total beta-lactamase (e.g. P3A, or the other beta-lactamase agents described herein, and variants thereof) and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the beta-lactamase (e.g. P3A, or the other beta-lactamase agents described herein, and variants thereof) and/or additional therapeutic agent in the modified-release formulation in intestinal fluid or simulated intestinal fluid in about 15, or about 30; or about 45, or about 60, or about 90 minutes. In some embodiments, the modified-release formulation is unstable in near neutral to alkaline environments. These modified-release formulations release about 70% or more by weight of the beta-lactamase (e.g. P3A, or the other beta-lactamase agents described herein, and variants thereof) and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of beta-lactamase (e.g. P3A, or the other beta-lactamase agents described herein, and variants thereof) and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In one embodiment, the modified-release formulation may remain essentially intact, or may be essentially insoluble, in gastric fluid. The modified-release formulation may include one or more delayed-release coatings that are pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

Alternatively, the stability of the modified-release formulation can be enzyme-dependent. In such embodiments, the modified-release formulation may include one or more delayed-release coatings that are enzyme-dependent, Delayed-release coating that are enzyme-dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora.

In various embodiments, the modified-release formulations comprising a beta-lactamase (e.g. P3A, or variants thereof) are substantially stable in chyme. For example, there is, in some embodiments, a loss of less about 50% or about 40%, or about 30%, or about 20%, or about 10% of beta-lactamase activity in about 10, or 9, or 8, or 7, or 6, or 5, or 4, or 3, or 2, or 1 hour from administration.

In some embodiments, a dual pulse formulation is provided. In various embodiments, the present invention provides for modified-release formulations that release multiple doses of the beta-lactamase (e.g. P3A, or the other beta-lactamase agents described herein, and variants thereof), at different locations along the intestines, at different times, and/or at different pH. In an illustrative embodiment, the modified-release formulation comprises a first dose of the beta-lactamase and a second dose of the beta-lactamase, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the beta-lactamase (e.g. P3A, or the other beta-lactamase agents described herein, and variants thereof) at different locations along the intestines, at different times, and/or at different pH. Further the dual pulse description herein applies to modified-release formulations that release a beta-lactamase (e.g. P3A, or the other beta-lactamase agents described herein, and variants thereof) and an additional therapeutic agent.

Modified Release Formulation and Dosage Forms

The modified-release formulation of beta-lactamase (e.g. P3A, or the other beta-lactamase agents described herein, and variants thereof) may further comprise a pharmaceutically acceptable carrier or excipient. As one skilled in the art will recognize, the formulations can be in any suitable form appropriate for the desired use and route of administration.

In some embodiments, the administration of the modified-release formulation including beta-lactamase (and/or additional therapeutic agents) is any one of oral, intravenous, and parenteral. In some embodiments, the administration of the modified-release formulation including beta-lactamase (and/or additional agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, particularly to the ears, nose, eyes, or skin.

Any modified-release formulation including beta-lactamase (and/or additional therapeutic agents) as described herein can be administered orally. Such inventive formulations can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. In some embodiments, administration is not at the site of infection to avoid, for example, hydrolysis of an antibiotic at the site of infection. Various delivery systems are known, e.g., encapsulation in liposomes, microparticles, microcapsules, capsules, etc., and can be used for administration. In specific embodiments, it may be desirable to administer locally to the area in need of treatment.

Suitable dosage forms for oral use include, for example, solid dosage forms such as tablets, dispersible powders, granules, and capsules. In one embodiment, the modified-release formulation is in the form of a capsule. In another embodiment, the modified-release formulation is in the form of a tablet. In yet another embodiment, the modified-release formulation is in the form of a soft-gel capsule. In a further embodiment, the modified-release formulation is in the form of a gelatin or hydroxypropyl methylcellulose (HPMC) capsule.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinyipyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The modified release formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The modified-release formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The modified-release formulation can also include one or more application solvents. Some of the more common solvents that can be used to apply, for example, a delayed-release coating composition include isopropyl alcohol, acetone, methylene chloride and the like.

The modified-release formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

The solid oral dosage forms can be prepared by, for example granulation (e.g., wet or dry granulation) of the agents of the invention with one or more suitable excipients. Alternatively, the agents of the invention can be layered onto an inert core (e.g., a nonpareil/sugar sphere such as a sucrose sphere or silica sphere) using conventional methods such as fluidized bed or pan coating, or extruded and spheronized using methods known in the art, into active compound-containing pellets. In embodiment, the beta-lactamase (e.g.

P3A, or the other beta-lactamase agents described herein, and variants thereof) is spray-coated onto a sucrose sphere. Such pellets can then be incorporated into tablets or capsules using conventional methods.

Suspensions, in addition to the active agents, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Besides inert diluents, the oral compositions can also include adjuvants such as sweetening, flavoring, and perfuming agents.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The formulations comprising the beta-lactamase (and/or additional therapeutic agents) may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc. followed by tableting using conventional methods known in the art).

In various embodiments, the modified-release formulation of the present invention may utilize one or more modified-release coatings such as delayed-release coatings to provide for effective, delayed yet substantial delivery of the beta-lactamase (e.g. P3A, or the other beta-lactamase agents described herein, and variants thereof) to the GI tract together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 300, L 30 D-55, L 100-55, L 100, L 12,5, L 12,5 P, RL 30 D, RL P0, RL 100, RL 12,5, RS 30 D, RS P0, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL P0, RL 100, RL 12,5, RS 30 D, RS P0, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 30 D-55.

In certain embodiments, one or more coating system additives are used with the enteric agent. For example, one or more PlasACRYL™ additives may be used as an antitacking agent coating additive. Exemplary PlasACRYL™ additives include, but are not limited to PlasACRYL™ HTP20 and PlasACRYL™ T20. In an embodiment, PlasACRYL™ HTP20 is formulated with EUDRAGIT® L 30 D-55 coatings. In another embodiment, PlasACRYL™ T20 is formulated with EUDRAGIT® FS 30 D coatings.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like: In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

In various embodiments, the invention provides a formulation comprising: a core particle having a base coat comprising one or more beta-lactamases (e.g. P3A, or the other beta-lactamase agents described herein, and variants thereof), and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more beta-lactamases may further comprise one or more additional therapeutic agents. Optionally a plurality of base coats may be applied to the core each of which may contain a beta-lactamase and/or an additional therapeutic agent. In an embodiment, the core particle includes sucrose. The formulation can be prepared by methods known in the art.

For example, a beta-lactamases (e.g., P3A, or the other beta-lactamase agents described herein, and variants thereof) can be sprayed onto an inert core (e.g., a sucrose core or sucrose sphere) and spray-dried with an enteric layer (e.g., Eudragit L30 D-55) to form beta-lactamase (e.g., P3A, or the other beta-lactamase agents described herein, and variants thereof)-containing pellets.

Optionally, the core particle may comprise one or more beta-lactamases (e.g., P3A, or the other beta-lactamase agents described herein, and variants thereof) and/or one or more additional therapeutic agents. In one embodiment, one or more doses of the beta-lactamase may be encapsulated in a core particle, for example, in the form of a microsphere. For example, the beta-lactamase may be combined with a polymer (e.g., latex), and then formed into a particulate, micro-encapsulated enzyme preparation, without using a sucrose core. The microspheres thus formed may be optionally covered with a delayed-release coating.

A variety of approaches for generating particulates (such as microspheres, aggregates, other) are known which are amenable to the inclusion of enzymes. They typically involve at least two phases, one containing the enzyme, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres. Alternatively, the beta-lactamase (e.g., P3A, or the other beta-lactamase agents described herein, and variants thereof) and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment.

In some embodiments, before applying the delayed-release coating to the coated core particle the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the formulation may comprise a plurality of modified-release particles or pellets or microspheres. In one embodiment, the formulation is in the form of capsules comprising multiple pellets. In one embodiment, the formulation is in the form of capsules comprising multiple microspheres.

In some embodiments, the modified-release formulation is a capsule filled with a plurality of beta-lactamase-containing pellets (e.g., P3A (or the other beta-lactamase agents described herein, and variants thereof)-containing pellets) from which the beta-lactamase is released. In an embodiment, the capsule is a gelatin capsule, such as a hard gelatin capsule. In another embodiment, the capsule is a hydroxypropyl methylcellulose (HPMC) capsule. For example, the formulation may be in the form of capsules comprising multiple pellets. For example, the formulation may be in the form of capsules such as, for example, gelatin or hydroxypropyl methylcellulose (HPMC) capsules comprising multiple enteric-coated pellets containing beta-lactamase (e.g. P3A, or the other beta-lactamase agents described herein, and variants thereof). In such an embodiment, a combination of pellets may be utilized in which each pellet is designed to release at a specific time point or location. In various embodiments, the pellets (e.g., enteric-coated pellets) are designed to pass through the stomach unchanged and then release the beta-lactamase (e.g. P3A, or the other beta-lactamase agents described herein, and variants thereof) into one or more regions of the intestines. In some embodiments, the beta-lactamase-containing pellets may be enteric-coated to release the beta-lactamase (e.g. P3A, or the other beta-lactamase agents described herein, and variants thereof) at different intestinal pH values.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise a beta-lactamase (e.g. P3A, or the other beta-lactamase agents described herein, and variants thereof), a sucrose sphere, which the beta-lactamase, for example, P3A or a variant, is sprayed onto, a binder excipient (e.g., hydroxypropylcellulose (HPC)), an enteric polymer (e.g., EUDRAGIT L 30 D-55), a plasticizer (e.g., triethyl citrate), a glidant (e.g., glyceryl monostearate), an emulsifier, and buffer salts.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise about 10-20% by weight of beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the pellets (or each individual pellet) comprise about 20-30% by weight sucrose sphere, which the beta-lactamase, for example, P3A or a variant, is sprayed onto. For example, the sucrose sphere may be present at about 20%, about 21%, about 22%, about 23%, about 24%, about 25%, about 26%, about 27%, about 28%, about 29%, or about 30% by weight. In various embodiments, the pellets (or each individual pellet) comprise about 30-40% by weight a binder excipient (e.g., hydroxypropylcellulose (HPC)). For example, the binder excipient may be present at about 30%, about 31%, about 32%, about 33%, about 34%, about 35%, about 36%, about 37%, about 38%, about 39%, or about 40% by weight. In some embodiments, the pellets (or each individual pellet) comprise about 15-25% by weight an enteric polymer (e.g. EUDRAGIT L 30 D-55). For example, the enteric polymer may be present at about 15%, about 16%, about 17%, about 18%, about 19%, about 20%, about 21%, about 22%, about 23%, about 24%, or about 25% by weight. In some embodiments, the pellets (or each individual pellet) comprise about 1.5-2.5% by weight of plasticizer (e.g., triethyl citrate). For example, the plasticizer may be present at about 1.5%, about 1.6%, about 1.7%, about 1.8%, about 1.9%, about 2%, about 2.1%, about 2.2%, about 2.3%, about 2.4%, about 2.5% by weight. In some embodiments, the pellets (or each individual pellet) comprise about 0.5-1.5% by weight glidant (e.g., glyceryl monostearate). For example, the glidant may be present at about 0.5%, about 0.6%, about 0.7%, about 0.8%, about 0.9%, about 1%, about 1.1%, about 1.2%, about 1.3%, about 1.4%, or about 1.5% by weight. In some embodiments, the pellets (or each individual pellet) comprise about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the pellets (or each individual pellet) further comprise about 1-2% by weight buffer salts. For example, the buffer salts may be present at about 1.1%, about 1.2%, about 1.3%, about 1.4%, about 1.5%, about 1.6%, about 1.7%, about 1.8%, about 1.9%, or about 2% by weight. The weight as described herein refers to the total weight of all components excluding the weight of the capsule itself.

In some embodiments, the pellets (or each individual pellet) comprise about 16% by weight of the beta-lactamase (e.g. P3A, or the other beta-lactamase agents described herein, and variants thereof); about 23% by weight sucrose sphere; about 35% by weight a binder excipient (e.g., hydroxypropylcellulose (HPC)); about 21% by weight an enteric polymer (e.g., EUDRAGIT L 30 D-55); about 2% by weight of plasticizer (e.g. triethyl citrate); about 1% by weight glidant (e.g., glyceryl monostearate); about 0.5% by weight emulsifier (e.g. polysorbate-80); and about 2% by weight buffer salts. The weight as described herein refers to the total weight of all components excluding the weight of the capsule itself.

For example, the pellets (or each individual pellet) comprise about 15.8% by weight of the beta-lactamase (e.g. P3A, or the other beta-lactamase agents described herein, and variants thereof); about 23.3% by weight sucrose sphere; about 35% by weight a binder excipient (e.g., hydroxypropylcellulose (HPC)); about 20.8% by weight an enteric polymer (e.g., EUDRAGIT L 30 D-55); about 2.1% by weight of plasticizer (e.g., triethyl citrate); about 1.0% by weight glidant (e.g., glyceryl monostearate); about 0.4% by weight emulsifier (e.g. polysorbate-80); and about 1.6% by weight buffer salts. The weight as described herein refers to the total weight of all components excluding the weight of the capsule itself.

In various embodiments, the formulation of the present invention is in the form of a capsule (e.g., a hard gelatin or HPMC capsule) comprising about 75 mg of the beta-lactamase (e.g. P3A, or the other beta-lactamase agents described herein, and variants thereof): The capsule includes a plurality of enteric-coated beta-lactamase-containing pellets. In such embodiments, the formulation comprises about 10-20% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the formulation comprises about 15-25% by weight sucrose sphere. For example, the sucrose sphere may be present about 15%, about 16%, about 17%, about 18%, about 19%, about 20%, about 21%, about 22%, about 23%, about 24%, or about 25% by weight. In various embodiments, the formulation comprises about 25-35% by weight a binder excipient (e.g., hydroxypropylcellulose (HPC)). For example, the binder excipient may be present at about 25%, about 26%, about 27%, about 28%, about 29%, about 30%, about 31%, about 32%, about 33%, about 34%, or about 35% by weight. In some embodiments, the formulation comprises about 10-25% by weight an enteric polymer (e.g., EUDRAGIT L 30 D-55). For example, the enteric polymer may be present at about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the formulation comprises about 1.5-2.5% by weight of plasticizer (e.g., triethyl citrate). For example, the plasticizer may be present at about 1.5%, about 1.6%, about 1.7%, about 1.8%, about 1.9%, about 2%, about 2.1%, about 2.2%, about 2.3%, about 2.4%, about 2.5% by weight. In some embodiments, the formulation comprises about 0.5-1.5% by weight glidant (e.g., glyceryl monostearate). For example, the glidant may be present at about 0.5%, about 0.6%, about 0.7%, about 0.8%, about 0.9%, about 1%, about 1.1%, about 1.2%, about 1.3%, about 1.4%, or about 1.5% by weight. In some embodiments, the formulation comprises about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 1-2% by weight buffer salts. For example, the buffer salts may be present at about 1%, about 1.1%, about 1.2%, about 1.3%, about 1.4%, about 1.5%, about 1.6%, about 1.7%, about 1.8%, about 1.9%, or about 2% by weight. In some embodiments, the formulation comprises about 10-20% by weight gelatin or HPMC capsule. For example, the gelatin or HPMC capsule may be about 10%, about 11%, about 12%, about 13%, about 14%, about 15%, about 16%, about 17%, about 18%, about 19%, or about 20% by weight.

In some embodiments, the formulation of the present invention comprising about 75 mg of the beta-lactamase (e.g. P3A, or the other beta-lactamase agents described herein, and variants thereof). In such embodiments, the formulation comprises about 13% by weight of the beta-lactamase (e.g. P3A, or the other beta-lactamase agents described herein, and variants thereof); about 19% by weight sucrose sphere; about 29% by weight a binder excipient (e.g., hydroxypropylcellulose (HPC)); about 17% by weight an enteric polymer (e.g., EUDRAGIT L 30 D-55); about 2% by weight of plasticizer (e.g., triethyl citrate); about 1% by weight glidant (e.g., glyceryl monostearate); about 0.5% by weight emulsifier (e.g. polysorbate-80); about 1% by weight buffer salts; and about 17% by weight gelatin or HPMC capsule.

For example, the formulation comprises about 13.1% by weight of the beta-lactamase (e.g. P3A, or the other beta-lactamase agents described herein, and variants thereof); about 19.4% by weight sucrose sphere; about 29.1% by weight a binder excipient (e.g., hydroxypropylcellulose (HPC)); about 17.3% by weight an enteric polymer (e.g., EUDRAGIT L 30 D-55); about 1.7% by weight of plasticizer (e.g., triethyl citrate); about 0.9% by weight glidant (e.g., glyceryl monostearate); about 0.4% by weight emulsifier (e.g. polysorbate-80); about 1.3% by weight buffer salts; and about 16.8% by weight gelatin or HPMC capsule.

In various embodiments, the formulation of the present invention is in the form of a capsule (e.g., a hard gelatin or HPMC capsule) comprising about 25 mg of the beta-lactamase (e.g. P3A, or the other beta-lactamase agents described herein, and variants thereof). The capsule includes a plurality of enteric-coated beta-lactamase-containing pellets. In such embodiments, the formulation comprises about 5-15% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about 5%, about 6%, about 7%, about 8%, about 9%, about 10%, about 11%, about 12%, about 13%, about 14%, or about 15% by weight. In some embodiments, the formulation comprises about 10-20% by weight sucrose sphere. For example, the sucrose sphere may be present about 10%, about 11%, about 12%, about 13%, about 14%, about 15%, about 16%, about 17%, about 18%, about 19%, or about 20% by weight. In various embodiments, the formulation comprises about 15-25% by weight a binder excipient (e.g., hydroxypropylcellulose (HPC)). For example, the binder excipient may be present at about 15%, about 16%, about 17%, about 18%, about 19%, about 20%, about 21%, about 22%, about 23%, about 24%, or about 25% by weight. In some embodiments, the formulation comprises about 10-20% by weight an enteric polymer (e.g., EUDRAGIT L 30 D-55). For example, the enteric polymer may be present at about 10%, about 11%, about 12%, about 13%, about 14%, about 15%, about 16%, about 17%, about 18%, about 19%, or about 20% by weight. In some embodiments, the formulation comprises about 1.0-2.0% by weight of plasticizer (e.g., triethyl citrate). For example, the plasticizer may be present at about 1.0%, about 1.1%, about 1.2%, about 1:3%, about 1.4%, about 1.5%, about 1.6%, about 1.7%, about 1.8%, about 1.9%, or about 2.0% by weight. In some embodiments, the formulation comprises about 0.1-1.0% by weight glidant (e.g., glyceryl monostearate). For example, the glidant may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 0.5-1.5% by weight buffer salts. For example, the buffer salts may be present at about 0.5%, about 0.6%, about 0.7%, about 0.8%, about 0.9%, about 1.0%, about 1.1%, about 1.2%, about 1.3%, about 1.4%, or about 1.5% by weight. In some embodiments, the formulation comprises about 30-40% by weight gelatin or HPMC capsule. For example, the gelatin or HPMC capsule may be about 30%, about 31%, about 32%, about 33%, about 34%, about 35%, about 36%, about 37%, about 38%, about 39%, or about 40% by weight.

In some embodiments, the formulation of the present invention comprising about 25 mg of the beta-lactamase (e.g. P3A, or the other beta-lactamase agents described herein, and variants thereof). In such embodiments, the formulation comprises about 10% by weight of the beta-lactamase (e.g. P3A, or the other beta-lactamase agents described herein, and variants thereof); about 15% by weight sucrose sphere; about 22% by weight a binder excipient hydroxypropylcellulose (HPC)); about 13% by weight an enteric polymer (e.g., EUDRAGIT L 30 D-55); about 1% by weight of plasticizer (e.g., triethyl citrate); about 0.5% by weight glidant glyceryl monostearate); about 0.3% by weight emulsifier (e.g. polysorbate-80); about 1% by weight buffer salts; and about 38% by weight gelatin or HPMC capsule.

For example, the formulation comprises about 9.8% by weight of the beta-lactamase (e.g. P3A, or the other beta-lactamase agents described herein, and variants thereof); about 14.5% by weight sucrose sphere; about 21.8% by weight a binder excipient hydroxypropylcellulose (HPC)); about 13% by weight an enteric polymer (e.g., EUDRAGIT L 30 D-55); about 1.3% by weight of plasticizer (e.g., triethyl citrate); about 0.6% by weight glidant (e.g., glyceryl monostearate); about 0.3% by weight emulsifier (e.g. polysorbate-80); about 1.0% by weight buffer salts; and about 37.7% by weight gelatin or HPMC capsule.

The present invention also provides for modified-release formulations that release multiple doses of the beta-lactamases (e.g., P3A, or the other beta-lactamase agents described herein, and variants thereof) and/or additional therapeutic agent along the gastrointestinal tract. In such embodiments, the overall release profile of such a formulation may be adjusted by utilizing, for example, multiple particle types or multiple layers. In one embodiment, the first dose of the beta-lactamase may be formulated for release in, for example, the small intestine (e.g., one or more of duodenum, jejunum, ileum) or the large intestine (e.g., one or more of cecum, ascending, transverse, descending or sigmoid portions of the colon, and rectum), whereas the second dose is formulated for delayed release in, for example, a different region of the small intestine (e.g., one or more of duodenum, jejunum, ileum) or the large intestine (e.g., one or more of cecum, ascending, transverse, descending or sigmoid portions of the colon, and rectum). Alternatively, multiple doses are released at different locations along the intestine. For example, in one embodiment, the first dose of the beta-lactamase may be formulated for release in, for example, the small intestine (e.g., one or more of duodenum, jejunum, ileum), whereas the second dose is formulated for delayed release in, for example, another part of the small intestine (e.g., one or more of duodenum, jejunum, ileum). In another embodiment, the first dose of the beta-lactamase may be formulated for release in, for example, the large intestine (e.g., one or more of cecum, ascending, transverse, descending or sigmoid portions of the colon, and rectum), whereas the second dose is formulated for delayed release in, for example, another part of the large intestine (e.g., one or more of cecum, ascending, transverse, descending or sigmoid portions of the colon, and rectum).

In various embodiments, the agents described herein may be in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the therapeutic agents, or separately by reacting the free base function with a suitable acid or a free acid functionality with an appropriate alkaline moiety. Representative acid addition salts include acetate, adipate, alginate, ascorbate, aspartate, benzenesuifonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In various embodiments, the present formulations provide a number of advantages. For instance, the inventors have successfully formulated a protein (i.e. beta-lactamase), which itself is challenging. This is compounded further by the GI tract environment in which the present formulations release drug in various embodiments. Further, in various embodiments, the present formulations provide for GI tract release that is sufficiently slow to allow good protective coverage in the GI tract from adverse effects of various antibiotics, e.g. in the small intestine (a benefit that is accentuated by an increase in beta-lactamase half-life that is commensurate with a slower release). Furthermore, by coating the drug substance layer of the present pellets with HPC, as opposed to EUDRAGIT, for example, the present formulations minimize the amount of EUGRAGIt in the formulations and therefore mitigate possible dose-limiting toxicity and manufacturing complications.

Administration and Dosage

It will be appreciated that the actual dose of the beta-lactamase (e.g., P3A, or the other beta-lactamase agents described herein, and variants thereof) to be administered according to the present invention will vary according to, for example, the particular dosage form and the mode of administration. Many factors that may modify the action of the beta-lactamase (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the beta-lactamase (e.g., P3A, or the other beta-lactamase agents described herein, and variants thereof) can be administered in unit dosage forms (e.g., tablets or capsules) containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween. In an embodiment, individual dose of the beta-lactamase (e.g., P3A, or the other beta-lactamase agents described herein, and variants thereof) is administered in an unit dosage form containing 25 mg of the beta-lactamase. In another embodiment, individual dose of the beta-lactamase (e.g. P3A, or the other beta-lactamase agents described herein, and variants thereof) is administered in an unit dosage form containing 50 mg of the beta-lactamase. In a further embodiment, individual dose of the beta-lactamase (e.g., P3A, or the other beta-lactamase agents described herein, and variants thereof) is administered in an unit dosage form containing 75 mg of the beta-lactamase.

In one embodiment, the beta-lactamase is administered at an amount of from about 0.01 mg to about 100 mg daily, an amount of from about 0.01 mg to about 1,000 mg daily from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily.

In various embodiments, the beta-lactamase is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the beta-lactamase (e.g., P3A, or the other beta-lactamase agents described herein, and variants thereof) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween. In other embodiments, a suitable dosage of the beta-lactamases in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the beta-lactamase may be administered, for example, about once per day, about every other day, about every third day, about once a week, about once every two weeks, about once every month, about once every two months, about once every three months, about once every six months, or about once every year. In certain embodiments, the beta-lactamase may be administered more than once daily, for example, about two times, about three times, about four times, about five times, about six times, about seven times, about eight times, about nine times, or about ten times daily.

Additional Therapeutic Agents and Combination Therapy or Co-Formulation

Administration of the present formulations may be combined with additional therapeutic agents. Co-administration of the additional therapeutic agent and the present formulations may be simultaneous or sequential. Further the present formulations may comprise an additional therapeutic agent (e.g. via co-formulation).

In some embodiments, the modified-release formulations of the present invention are administered in combination with an additional therapeutic agent. In an embodiment, the additional therapeutic agent and the beta-lactamase (e.g., P3A, or the other beta-lactamase agents described herein, and variants thereof) are combined into a single modified-release formulation. In some embodiments, the methods of treatment and/or prevention comprise administering the modified-release formulations of the present invention to a subject that is undergoing treatment with an additional therapeutic agent.

In one embodiment, the additional agent and the beta-lactamase are administered to a subject simultaneously. The term "simultaneously" as used herein, means that the additional agent and the beta-lactamase are administered with a time separation of no more than about 60 minutes, such as no more than about 30 minutes, no more than about 20 minutes, no more than about 10 minutes, no more than about 5 minutes, or no more than about 1 minute. Administration of the additional agent and the beta-lactamase can be by simultaneous administration of a single formulation (e.g., a formulation comprising the additional agent and the beta-lactamase) or of separate formulations (e.g., a first formulation including the additional agent and a second formulation including the beta-lactamase).

Co-administration does not require the additional therapeutic agents to be administered simultaneously, if the timing of their administration is such that the pharmacological activities of the additional agent and the beta-lactamase overlap in time, thereby exerting a combined therapeutic effect. For example, the additional agent and the beta-lactamase can be administered sequentially. The term "sequentially" as used herein means that the additional agent and the beta-lactamase are administered with a time separation of more than about 60 minutes. For example, the time between the sequential administration of the additional agent and the beta-lactamase can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional agent and the beta-lactamase being administered. Either the additional therapeutic agent or the beta-lactamase (e.g., P3A, or the other beta-lactamase agents described herein, and variants thereof) may be administered first.

Co-administration also does not require the additional therapeutic agents to be administered to the subject by the same route of administration. Rather, each additional therapeutic agent can be administered by any appropriate route, for example, parenterally or non-parenterally.

In some embodiments, the additional therapeutic agent is an additional antibiotic degradation enzyme, such as, for example, a beta-lactamase of class EC 3.5.2.6. In some embodiments, the antibiotic degradation enzyme is selected from a functional Group 1, Group 2, Group 3, or a Group 4 beta-lactamase (see, e.g., Bush et al., *Antimicrob. Agents Chemother,* 39: 1211, the contents of which are hereby incorporated by reference): without wishing to be bound by theory, Group 1 consists of cephalosporinases that are not well inhibited by clavulanic acid; Group 2 consists of penicillinases, cephalosporinases and broad-spectrum beta-lactamases that are generally inhibited by active site-directed beta-lactamase inhibitors; Group 3 consists of metallo-beta-lactamases that hydrolyze penicillins, cephalosporins and carbapenems, and that are poorly inhibited by almost all beta-lactam-containing molecules; and Group 4 consists of penicillinases that are not well inhibited by clavulanic acid) and/or a molecular/Ambler class A, or class B, or class C, or class D beta-lactamase (see, e.g., Ambler 1980, *Philos Trans R Soc Land B Biol Sci.* 289: 321 the contents of which are hereby incorporated by reference), without wishing to be bound by theory: Classes A, C, and D gather evolutionarily distinct groups of serine beta-lactamase enzymes, and class B the zinc-dependent ("EDTA-inhibited") beta-lactamase enzymes (see Ambler R. P. et al., 1991, *Biochem J.* 276: 269-270, the contents of which are hereby incorporated by reference). In some embodiments, the antibiotic degradation enzyme is a serine beta-lactamase or a zinc-dependent (EDTA-inhibited) beta-lactamase. For example, in some embodiments, the beta-lactamase is one or more of P1A, P2A, P3A, or P4A. Further, the beta-lactamase may be an extended-spectrum beta-lactamase (ESBL), optionally selected from a TEM, SHV, CTX-M, OXA, PER, VEB, GES, and IBC beta-lactamase. Further, the beta-lactamase may be an inhibitor-resistant β-lactamase, optionally selected from an AmpC-type β-lactamases, Carbapenemase, IMP-type carbapenemases (metallo-β-lactamases), VIM (Verona integron-encoded metallo-β-lactamase), OXA (oxacillinase) group of β-lactamases, KPC (*K. pneumonia* carbapenemase), CMY (Class C), SME, IMI, NMC and CcrA, and a NDM (New Delhi metallo-β-lactamase, e.g. NDM-1) beta-lactamase.

In some embodiments, the additional therapeutic agent is an adjunctive therapy that is used in, for example, the treatment of CDI as described herein. In some embodiments, the additional agent is metronidazole (e.g. FLAGYL), fidaxomicin (e.g. DIFICID), or vancomycin (e.g. Vancocin), rifaximin, fecal bacteriotherapy, charcoal-based binders (e.g. DAV132), probiotic therapy (see, e.g., Intnat'l J Inf Dis, 16 (11): e786, the contents of which are hereby incorporated by reference, illustrative probiotics include *Saccharomyces boulardii, Lactobacillus rhamnosus* GG; *Lactobacillus plantarum* 299v; *Clostridium butyricm* M588; *Clostridium difficile* VP20621 (non-toxigenic *C. difficile* strain); combination of *Lactobacillus casei, Lactobacillus acidophilus* (Bio-K CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the content of which are hereby incorporated by reference in their entirety; neutralizing binding proteins; for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin. In some embodiments, any of the penicillins and cephalosporins described herein may be the additional agent.

In some embodiments; the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide; motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS), Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fiuclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone; triamcinolone acetonide, cortisone, cortodoxone, fiucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometha-lone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indometacin. Additional anti-inflammatory agents are described, for example, in U.S. Pat. No. 4,537,776, the entire contents of which are incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(B-methyl-N-vanillyl-6E-nonenamide), "synthetic" capsaicin(N-vanillylnonamide), and related compounds.

For all additional agent compositions and methods, targeting to various parts of the GI tract may be employed as described herein.

In some embodiments, the present formulations are administered to a patient to avoid treatment with an additional therapeutic agent. For example, in the context of preventing C. difficile infection (CDI) and/or a C. difficile-associated disease, the present formulations may be provided to a patient to avoid the necessity of receiving, for example, vancomycin.

Methods of Treatment

In various aspects, the present invention provides modified-release formulations including beta-lactamase (and/or additional agent) for use in treating an antibiotic-induced adverse effect in the GI tract and/or prevention or treatment of C. difficile infection (CDI) and/or a C. difficile-associated disease. In other aspects, there are provided uses of the modified-release formulations including beta-lactamase (and/or additional agent) for treating an antibiotic-induced adverse effect in the GI tract and/or preventing or treating a C. difficile infection (CDI) and/or a C. difficile-associated disease.

In various aspects, the present invention provides methods for treating or preventing an antibiotic-induced adverse effect in the GI tract, comprising administering an effective amount of a modified-release formulation including beta-lactamase (e.g., P3A, or the other beta-lactamase agents described herein, and variants thereof) and/or additional therapeutic agent described herein to a patient in need thereof. In one aspect, the present invention provides methods for preventing an antibiotic-induced adverse effect in the GI tract, comprising administering an effective amount of a modified-release formulation including beta-lactamase (e.g., P3A, or the other beta-lactamase agents described herein, and variants thereof) and/or additional therapeutic agent described herein to a patient in need thereof (by way of non-limiting example, a patient that is being administered or will be administered an antibiotic, including those described herein).

In various aspects, the present invention provides methods for protecting a subject's gastrointestinal microbiome, comprising administering an effective amount of a modified-release formulation including beta-lactamase (e.g., P3A, or the other beta-lactamase agents described herein, and variants thereof) and/or additional therapeutic agent described herein. In various embodiments, the subject is undergoing treatment or has recently undergone treatment with an antibiotic. In various embodiments, the antibiotic is one or more of a penicillin, cephalosporin, monobactam, and carbapenem as described herein. In an embodiment, the beta-lactamase is P3A.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a women and/or is elderly (e.g. over about 65 years old) and/or is an elderly woman and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In various embodiments, the beta-lactamase (e.g., P3A, or the other beta-lactamase agents described herein, and variants thereof), optionally formulated in a modified release format as described herein, protects the intestinal microbiome from antibiotics-induced damage. In an illustrative embodiment, the beta-lactamase (e.g., P3A, or the other beta-lactamase agents described herein, and variants thereof), optionally formulated in a modified release format as described herein, protects the intestinal microbiome from cephalosporin-induced damage. For example, in some embodiments, the beta-lactamase (e.g., P3A, or the other beta-lactamase agents described herein, and variants thereof), optionally formulated in a modified release format as described herein, protects the intestinal microbiome from damage induced by cephalosporin, which may be one or more of:

| Generic | Brand Name |
|---|---|
| First Generation | |
| Cefacetrile (cephacetrile) | CELOSPOR, CELTOL, CRISTACEF |
| Cefadroxil (cefadroxyl) | DURICEF, ULTRACEF |
| Cefalexin (cephalexin) | KEFLEX, KEFTAB |
| Cefaloglycin (cephaloglycin) | KEFGLYCIN |
| Cefalonium (cephalonium) | |
| Cefaloridine (cephaloradine) | |
| Cefalotin (cephalothin) | KEFLIN |
| Cefapirin (cephapirin) | CEFADYL |
| Cefatrizine | |
| Cefazaflur | |
| Cefazedone | |
| Cefazolin (cephazolin) | ANCEF, KEFZOL |
| Cefradine (cephradine) | VELOSEF |
| Cefroxadine | |
| Ceftezole | |
| Second Generation | |
| Cefaclor | CECLOR, CECLOR CD, DISTACLOR, KEFLOR, RANICOR |
| Cefamandole | MANDOL |
| Cefmetazole | |
| Cefonicid | MONOCID |
| Cefotetan | CEFOTAN |
| Cefoxitin | MEFOXIN |
| Cefprozil (cefproxil) | CEFZIL |
| Cefuroxime | CEFTIN, KEFUROX, ZINACEF, ZINNAT |
| Cefuzonam | |
| Third Generation | |
| Cefcapene | |
| Cefdaloxime | |
| Cefdinir | OMNICEF, CEFDIEL |
| Cefditoren | SPECTRACEF |
| Cefetamet | |
| Cefixime | SUPRAX |
| Cefmenoxime | CEFMAX |
| Cefodizime | |
| Cefotaxime | CLAFORAN |
| Cefpimizole | |
| Cefpodoxime | VANTIN |
| Cefteram | |
| Ceftibuten | CEDAX |

| Generic | Brand Name |
|---|---|
| Ceftiofur | EXCEDE |
| Ceftiolene | |
| Ceftizoxime | CEFIZOX |
| Ceftriaxone | ROCEPHIN |
| Cefoperazone | CEFOBID |
| Ceftazidime | CEPTAZ, FORTUM, FORTAZ, TAZICEF, TAZIDIME |
| | Fourth Generation |
| Cefclidine | |
| Cefepime | MAXIPIME |
| Cefluprenam | |
| Cefoselis | |
| Cefozopran | |
| Cefpirome | CEFROM |
| Cefquinome | |
| | Fifth Generation |
| Ceftobiprole | ZEFTERA |
| Ceftaroline | TEFLARO |
| | Not Classified |
| Cefaclomezine | |
| Cefaloram | |
| Cefaparole | |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |

In one embodiment, the beta-lactamase (e.g., P3A, or the other beta-lactamase agents described herein, and variants thereof), optionally formulated in a modified release format as described herein, protects the intestinal microbiome from ceftriaxone (CRO)-induced damage. In some embodiments, the methods of the invention treat or prevent a ceftriaxone-associated adverse effect (e.g. diarrhea, nausea, vomiting, dysgeusia, and pseudomembranous colitis disease and/or symptoms).

Antibiotics treatment such as ceftriaxone treatment may result in an abnormal growth (e.g., an overgrowth and/or overabundance) of methanogens. Methanogens include microorganisms that produce methane as a metabolic byproduct. Examples of methanogens include but are not limited to, Methanobacterium bryantii, Methanobacterium formicum, Methanobrevibacter arboriphilicus, Methanobrevibacter gottschalkii, Methanobrevibacter ruminantium, Methanobrevibacter smithii, Methanocalculus chunghsingensis, Methanococcoides burtonii, Methanococcus aeoiicus, Methanococcus deltae, Methanococcus jannaschii, Methanococcus maripaludis, Methanococcus vannieili, Methanocorpusculum labreanum, Methanocuileus bourgensis (Methanogenium olentangyi, Methanogenium bourgense), Methanoculieus marisnigri, Methanofolis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta conciiii, Methanosaeta thermophile, Methanosarcina acetivorans, Methanosarcina barked, Methanosarcina mazei, Methanosphaera stadtmanae, Methanospirillium hungatei, Methanothermobacter defiuvii (Methanobacterium defiuvii), Methanothermobacter thermautotrophicus (Methanobacterium thermoautotrophicum), Methanothermobacter thermoflexus (Methanobacterium thermoflexum), Methanothermobacter wolfei (Methanobacterium wolfei), and Methanothrix sochngenii. In an embodiment, the methanogen is Methanobrevibacter smithii. In various embodiments, the beta-lactamase (e.g., P3A, or the other beta-lactamase agents described herein, and variants thereof), optionally formulated in a modified release format as described herein, prevents one or more of an abnormal presence or absence of methanogens, abnormal levels of methanogens, overgrowth of methanogens, elevated levels of methanogenesis, elevated enteric methane levels, excessive hydrogen scavenging by hydrogen-consuming methanogens or colonization of methanogens in an abnormal location (e.g., in the small bowel rather than large bowel). In one embodiment, the beta-lactamase (e.g., P3A, or the other beta-lactamase agents described herein, and variants thereof), optionally formulated in a modified release format as described herein, protects the intestinal microbiome from an overgrowth and/or overabundance of methanogens, such as Methanobrevibacter smithii.

In various embodiments, antibiotics treatment such as ceftriaxone treatment may also result in an abnormal growth such as a reduction or underrepresentation of bacterial species. In an embodiment, antibiotics treatment results in a reduction or underrepresentation of Turicibacter spp. Exemplary Turicibacter spp. include, but are not limited to, T. sanguinis, Turicibacter sp. HGF1, Turicibacter sp. LA61, Turicibacter sp. L462, Turicibacter sp. HGA0205, and Turicibacter sp. HGH0181. In an embodiment, the bacterial species is T. sanguinis. A reduction in Turicibacter spp. has been associated with idiopathic inflammatory bowel disease and acute hemorrhagic diarrhea in dogs (Minamoto et al., 2015, Gut Microbes 6(1), 33-47; Rossi et al., 2014, PLoS ONE 9(4), e94699). Accordingly, in various embodiments, the beta-lactamase (e.g., P3A, or the other beta-lactamase agents described herein, and variants thereof), optionally formulated in a modified release format as described herein, protects the intestinal microbiome from a reduction and/or underrepresentation of Turicibacter spp. such as T. sanguinis.

In various embodiments, the beta-lactamase (e.g., P3A, or the other beta-lactamase agents described herein, and variants thereof), optionally formulated in a modified release format as described herein, works to retain a normal diversity of bacteria in the intestinal tract. For example, such treatment retains a balance of Bacteroidetes, Proteobacteria and Firmicutes. In some embodiments, the P3A (optionally formulated in a modified release format as described herein) prevents or reduces dysbiosis. In some embodiments, the P3A (optionally formulated in a modified release format as described herein) prevents or reduces the eradication of, or substantial reduction of, Firmicutes in the GI tract.

In one embodiment, the beta-lactamase (e.g., P3A, or the other beta-lactamase agents described herein, and variants thereof), optionally formulated in a modified release format as described herein, protects the intestinal microbiome by protecting the anaerobic and facultative aerobic bacterial species from antibiotic-mediated changes. Illustrative anaerobic and facultative aerobic bacterial species include, but are not limited to, S. infantarius, B. vulgatus, Lachnospiraceae bacterium, Turicibacter sp., R. gnavus, B. bifidum, P. merdae, A. putredinis, Clostridium sp., C. symbiosum, C. hathewayi, C. citroniae, C. ramosum, C. flexile, C. difficile, C. clostridioforme, E. coli, Alistipes sp., Bitidobacterium sp., E. faecium, L. plantarum, E. faecalis, R. torques, L.

*fermentum, pneumoniae, S. thermophilus, P. distasonis, Mollicutes bacterium, Enterococcus* sp., *Bacteroides* sp., *Ruminococcaceae bacterium, Clostridiales bacterium, Klebsiella* sp., *L. lactis, A. caccae,* and *E. gallinarum.*

In one embodiment, the beta-lactamase (e.g., P3A, or the other beta-lactamase agents described herein, and variants thereof), optionally formulated in a modified release format as described herein, is able to maintain a proper ratio of gram positive/gram negative microorganisms in the intestines. For example, in an embodiment, the beta-lactamase P3A, or the other beta-lactamase agents described herein, and variants thereof), optionally formulated in a modified release format as described herein, is able to maintain an overabundance of gram positive microorganisms in the intestines. In another embodiment, the beta-lactamase (e.g., P3A, or the other beta-lactamase agents described herein, and variants thereof), optionally formulated in a modified release format as described herein, is able to reduce the number of gram negative microorganisms in the intestines.

In various embodiments, the present invention provides for compositions and methods that mitigate or prevent the overgrowth of various coliforms in a patient's gut (including conforms that are virulent and/or antibiotic resistant). In various aspects, the methods and compositions described herein prevent or diminish secondary infections with resistant organisms and may, in some embodiments, diminish beta-lactam resistance development. Further, the methods and compositions described herein may allow for use of beta-lactam antibiotics which are currently avoided due to resistance concerns and/or reduce the need for co-administration or co-formulation with one or more beta-lactamase inhibitors (e.g. AUGMENTIN is a mixture of amoxicillin and clavulanic acid).

In various aspects, the present invention provides methods for treating or preventing acute hemorrhagic diarrhea. In various aspects, the present invention provides methods for treating or preventing inflammatory bowel disease, including, for example, idiopathic inflammatory bowel disease. In various aspects, the present invention provides methods for treating or preventing one or more of constipation, irritable bowel syndrome, and obesity.

In various aspects, the present invention provides methods for treating or preventing *C. difficile* infection (CDI) and/or a *C. difficile*-associated disease, comprising administering an effective amount of a modified-release formulation including beta-lactamase (e.g., P3A, or the other beta-lactamase agents described herein, and variants thereof) and/or additional therapeutic agent described herein to a patient in need thereof. In one aspect, the present invention provides methods for preventing *C. difficile* infection (CDI) and/or a *C. difficile*-associated disease, comprising administering an effective amount of a modified-release formulation including beta-lactamase (e.g., P3A, or the other beta-lactamase agents described herein, and variants thereof) and/or additional therapeutic agent described herein to a patient in need thereof (by way of non-limiting example, a patient that is being administered or will be administered an antibiotic, including those described herein.

In some embodiments, the invention relates to a method of preventing *C. difficile* infection (CDI) and/or a *C. difficile*-associated disease, comprising administering an effective amount of a modified-release formulation including beta-lactamase (e.g., P3A, or the other beta-lactamase agents described herein, and variants thereof) and/or additional therapeutic agent described herein to a patient in need thereof, wherein the patient is undergoing therapy with a primary antibiotic and the primary antibiotic is one or more of a ceftriaxone, cetotaxime, cefazolin, cefoperazone, cefuroxime, and piperacillin and is administered intravenously. In some embodiments, the patient is not undergoing treatment with an initial and/or adjunctive therapy that is one or more of metronidazole, vancomycin, fidaxomicin, rifaximin, fecal bacteriotherapy, probiotic therapy, and antibody therapy.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various embodiments, the CDI and/or *C. difficile* associated disease is treated or prevented in the context of initial onset or relapse/recurrence (e.g. due to continued or restarted antibiotic therapy). For example, in a patient that has previously suffered from CDI, the present modified-release formulation including beta-lactamase (and/or additional agent) may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or *C. difficile* associated disease may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, CDI and/or *C. difficile* associated disease may also be diagnosed via enzyme immunoassays, e.g., to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotoxicity assay. For example, any of the following tests may be used: Meridian ImmunoCard Toxins A/B; Wampole Toxin A/B Quik Chek; Wampole *C. diff* Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerleux Vidas *C. difficile* Toxin A&B; BD Geneohm *C. diff*; Prodesse Progastro CD; and Cepheid Xpert *C. diff*. In various embodiments, the clinical sample is a patient stool sample.

Also a flexible sigmoidoscopy "scope" test and/or an abdominal X-ray and/or a computerized tomography (CT) scan, which provides images of your colon, may be used in assessing a patient (e.g. looking for characteristic creamy white or yellow plaques adherent to the wall of the colon). Further, biopsies (e.g. of any region of the GI tract) may be used to assess a potential CDI and/or *C. difficile* associated disease patient.

Furthermore, the methods of the invention may treat patients including, but are not limited to, patients that are at a particular risk for CDI and/or *C. difficile* associated disease, such as those which have been taking an antibiotic during the past 30 or so days and/or have an immune system that is weak (e.g. from a chronic illness) and/or are women and/or are elderly (e.g. over about 65 years old) and/or are elderly woman and/or undergo treatment with for heartburn or stomach acid disorders (e.g. with agents such as PREVACID, TAGAMET, PRILOSEC, or NEXIUM and related drugs) and/or have recently been in the hospital, including in an intensive care unit, or live in a nursing home. Accordingly, in some embodiments, the methods and uses of the present invention treat or prevent a nosocomial infection and/or a secondary emergent infection and/or a hospital acquired infection (HAI).

In some embodiments, the methods and uses of the present invention relate to a patient is undergoing treatment or has recently undergone treatment with one or more primary antibiotic. A "primary antibiotic" refers to an antibiotic that is administered to a patient and which may result in CDI and/or C. difficile associated disease. These include the antibiotics that most often lead to CDI and/or C. difficile associated disease: fluoroquinolones, cephalosporins, clindamycin and penicillins.

In some embodiments, the methods and uses of the present invention relate to the modified-release formulation including beta-lactamase (e.g., P3A, or the other beta-lactamase agents described herein, and variants thereof) and/or additional therapeutic agent which hydrolyze a primary antibiotic before it enters the GI tract, including the small and/or large intestine. In some embodiments, the methods and uses of the present invention relate to the modified-release formulation including beta-lactamase (e.g., P3A, or the other beta-lactamase agents described herein, and variants thereof) and/or additional therapeutic agent which hydrolyze a primary antibiotic before it enters the large intestine. In some embodiments, the methods and uses of the present invention relate to the modified-release formulation including beta-lactamase (and/or additional agent) which hydrolyze excess antibiotic residue in the GI tract. In some embodiments, methods and uses of the present invention relate to the modified-release formulation including beta-lactamase (and/or additional agent) which maintain a normal intestinal microbiota and/or prevent the overgrowth of one or more pathogenic microorganisms in the GI tract of a patient. In some embodiments, methods and uses of the present invention relate to the modified-release formulation including beta-lactamase (and/or additional agent) which maintain a normal intestinal microbiota and/or prevent the reduction of one or more beneficial microorganisms in the GI tract of a patient. In various embodiments, the beta-lactamases and/or pharmaceutical compositions (and/or additional agents) do not substantially interfere with plasma levels of a primary antibiotic. For example, the beta-lactamases and/or pharmaceutical compositions (and/or additional agents) of the present invention allow for a patient to receive a primary antibiotic that might be required for an infection and do not interfere with the systemic utility of the antibiotic. Rather, the beta-lactamases and/or pharmaceutical compositions (and/or additional agents) inactivate excess antibiotic that may populate parts of the GI tract and in doing so, prevent the disruption of the microbiota that is linked to the various disease states described herein.

In various embodiments, the inventive modified-release formulations including beta-lactamase (e.g., P3A, or the other beta-lactamase agents described herein, and variants thereof) and/or additional therapeutic agent are not systemically absorbed: In various embodiments, the modified-release formulations including beta-lactamase (and/or additional agent) do not substantially interfere with the activity of systemically administered antibiotics. In various embodiments, the modified-release formulations including beta-lactamase (and/or additional agent) function to eliminate antibiotics from interfering with the microbiota of a microbiome (e.g. the gut, including the large intestine). In some embodiments, the modified-release formulations including beta-lactamase (and/or additional agent) do not interfere with the antibiotic absorption from the gut and/or enterohepatically sufficiently to alter the half-lives of antibiotic circulation. In some embodiments, the modified-release formulations including beta-lactamase (and/or additional agent) do not interfere with the antibiotic absorption from the gut and/or enterohepatically enough to be clinically important.

In some embodiments, the methods and uses of the present invention include those in which an initial and/or adjunctive therapy is administered to a subject. Initial and/or adjunctive therapy indicates therapy that is used to treat for example, a microbiome-mediated disorder or disease upon detection of such disorder or disease. In an embodiment, initial and/or adjunctive therapy indicates therapy that is used to treat CDI and/or C. difficile associated disease upon detection of such disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy, as described herein. In various embodiments, the methods and uses of the present invention include use of the modified-release formulation including beta-lactamase (e.g., P3A, or the other beta-lactamase agents described herein, and variants thereof) and/or additional therapeutic agent described herein as an adjuvant to any of these initial and/or adjunctive therapies (including co-administration or sequential administration). In various embodiments, the methods and uses of the present invention include use of the modified-release formulation including beta-lactamase (e.g., P3A, or the other beta-lactamase agents described herein, and variants thereof) and/or additional therapeutic agent described herein in a subject undergoing initial and/or adjunctive therapies.

In various embodiments; the present uses and methods pertain to co-treatment (simultaneously or sequentially) with the modified-release formulation including beta-lactamase and any additional therapeutic agent described herein and/or any initial and/or adjunctive therapy, or treatment with a co-formulation of the modified-release formulation including beta-lactamase and any additional therapeutic agent described herein and/or any initial and/or adjunctive therapy for treatment of the various diseases described herein, or methods of treating the various diseases described herein in a patient undergoing treatment with any additional agent described herein and/or any initial and/or adjunctive therapy described herein by administering the modified-release formulation including beta-lactamase to the patient.

In some embodiments; the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

Kits

The invention provides kits that can simplify the administration of the modified-release formulation described herein. The kit is an assemblage of materials or components, including at least one of the modified-release formulations described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat a disorder associated described herein. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Examples

Example 1: Manufacturing of P3A Delayed-Release Pellets and Capsules

A P3A formulation including P3A enteric-coated pellets was produced. To produce the pellets, P3A was spray-coated onto a sucrose core and spray-dried with an enteric layer, Eudragit L30 D-55, to protect the P3A active pharmaceutical ingredient from the acidic conditions of the stomach. The Eudragit L30 D55 polymer begins to depolymerize when the pH rises to 5.5 and above in the small intestine, thus releasing the active drug from the pellet.

Delayed-release capsules including the P3A enteric-coated pellets were manufactured in a GMP process as depicted in FIG. 1A. Specifically, the GMP manufacture of P3A Delayed-Release Capsule was a three stage sequential process including: 1) P3A drug layering onto sucrose core pellets by spray application, 2) enteric coating with EUDRAGIT® L 30 D-55 using spray application, and 3) encapsulation of pellets into hard gelatin capsules size 0.

P3A layered pellets were produced by spray application of P3A drug substance using hydroxypropylcellulose (HPC) as a binder excipient, water as a solvent, and sucrose spheres as starting material. The spray application was performed using a fluid bed system over six work shifts, in order to achieve a final active pharmaceutical agent (API) percentage of at least 15%. After the sixth work shift of spray application of the P3A/HPC mixture, the P3A layered pellets were dried overnight at room temperature on trays, then sifted through a 1.4 mm sieve prior to bulk packaging in polyethylene (PE) bags and PE containers. The drug-layered pellets were stored at 5±3° C. for further processing. It is notes that attempts to use hydroxymethylcellulose (HMC) as a binder excipient were unsuccessful as this produced flaky pellets that could not be furthered processed (e.g. spray dried).

In a subsequent process, the P3A layered pellets were coated with methacrylic acid ethyl acrylate copolymer (EUDRAGIT® L 30 D-55) as an enteric polymer, triethyl citrate as a plasticizer, glyceryl monostearate as a glidant, polysorbate-80 as an emulsifier, and water as a diluent. The coating was performed using a fluid bed system in a single work shift. The enteric coated P3A layered pellets were dried overnight at room temperature on trays and sifted through a 1.6 mm sieve prior to packaging as bulk pellets in PE bags and PE containers. The enteric coated P3A layered pellets were stored at 5±3° C. for further processing.

The enteric coated P3A layered pellets were encapsulated in hard gelatin capsules using an automated capsule filler with a capsule transport and dosing unit for filling size 0 capsules. The final P3A delayed-release capsules, 75 mg, were packed as bulk Drug Product in PE bags and PE containers, and stored at 5±3° C. ready for shipment.

In a separate manual process to manufacture P3A delayed-release capsules, 25 mg, the enteric P3A layered pellets were encapsulated in hard gelatin capsules using an analytical balance, capsule filling funnel for filling size 0 capsules. The final P3A delayed-release capsule, 25 mg were packed as bulk Drug Product in PE bags and PE containers, and stored at 5±3° C. ready for shipment.

P3A delayed-release capsules, intended for use in clinical trials and stability studies, were packaged in a 100 cc high density polyethylene (HDPE) round bottle with 38 mm polypropylene (PP) child resistant closures, with an induction seal.

During manufacturing, a list of in-process controls, as shown in Table 1, were employed for the P3A delayed-release capsules, 75 mg and 25 mg. These tests were performed on manufactured P3A delayed-release pellets prior to encapsulation.

TABLE 1

P3A Delayed-Release Capsule Manufacturing In-Process Controls

| Test | In-Process Step | Test Method | Specification |
|---|---|---|---|
| Appearance | Post-enteric coating | Visual | White to slightly yellowish, spherical and evenly sized, free flowing |

TABLE 1-continued

P3A Delayed-Release Capsule Manufacturing In-Process Controls

| Test | In-Process Step | Test Method | Specification |
|---|---|---|---|
| Particle Size Distribution | Post-enteric coating | USP | Reported |
| Biological Activity by CENTA Assay | Post-enteric coating | QKY24701 | 12.6-19.0% (80-120% label claim) |

As a control, placebo capsules containing placebo buffer were also produced using an essentially identical process as the P3A delayed-release capsules. Specifically, the placebo capsules were manufactured according to the batch records similar to the P3A delayed-release capsule, 75 mg drug product.

The final placebo capsules were packed as bulk product in PE bags and PE containers, and stored at 5+3° C. ready for shipment. The placebo capsules intended for use in clinical trials were packaged in a 100 cc HOPE round bottle with 38 mm PP child resistant closures, with an induction seal.

During manufacturing of the placebo capsules, a list of in-process controls, as shown in Table 2, were also employed. The tests were performed on the placebo pellets prior to encapsulation.

TABLE 2

P3A Placebo Capsule Manufacturing In-Process Controls

| Test | In-Process Step | Test Method | Specification |
|---|---|---|---|
| Appearance | Post-enteric coating | Visual | White to slightly yellowish, spherical and evenly sized, free flowing |
| Particle Size Distribution | Post-enteric coating | USP | Reported |
| Biological Activity by CENTA Assay | Post-enteric coating | QKY24701 | ≤Limit of Detection (<1% of label claim) |

In addition, a non-GMP batch of P3A Delayed-Release pellets was manufactured for nonclinical use using the same process flow as described in FIG. 1A, with the exception of the final encapsulation of pellets by the manufacturer. Instead, bulk P3A delayed-release pellets were tested and stored in bulk. Subsequent to the release testing for non-clinical use, the non-GMP batch was encapsulated in size 0 hard gelatin capsules and placed on a stability study.

Example 2: Composition and Appearance of P3A Delayed-Release Pellets and Capsules The P3A dosage form is a hard gelatin capsule or a hydroxypropyl methylcellulose (HPMC) capsule filled with delayed-release pellets. The capsule is opaque white or white and is size 0. The delayed-release capsule contains pellets composed of sucrose spheres coated with an inner layer of P3A drug substance in excipients and a pH sensitive enteric outer coat in excipients. The pellets are designed to begin dissolving in the upper small intestine as the pH rises above 5.5, releasing the drug substance.

The list of components and the amounts in P3A delayed-release capsules (75 mg and 25 mg strength) and placebo capsules are provided in Table 3. For the 75 mg and 25 mg strength P3A delayed-release capsules, pellets from the same manufacture batch were encapsulated to the desired capsule strength, so the percent of each component is identical. For the placebo capsules, the placebo pellets were encapsulated to match the level of EUDRAGIT® L 30 D-55 enteric coat excipient (20.8%) of the P3A delayed-release capsule, 75 mg drug product.

TABLE 3

Composition of P3A Delayed-Release Capsules, 75 mg and 25 mg, and Placebo Capsule

| Component | 75 mg Capsule mg | 75 mg Capsule % Total | 25 mg Capsule mg | 25 mg Capsule % Total | Placebo Capsule mg | Placebo Capsule % Total |
|---|---|---|---|---|---|---|
| Sucrose sphere | 110.8 | 23.3 | 36.9 | 23.3 | 139.8 | 29.5 |
| Hydroxypropylcellulose | 166.3 | 35.0 | 55.4 | 35.0 | 209.6 | 44.2 |
| EUDRAGIT ® L 30 D-55 | 98.9 | 20.8 | 33.0 | 20.8 | 98.7 | 20.8 |
| P3A | 75.0 | 15.8 | 25.0 | 15.8 | — | — |
| Buffer salts | 7.5 | 1.6 | 2.5 | 1.6 | 9.4 | 2.0 |
| Glyceryl monostearate | 4.9 | 1.0 | 1.6 | 1.0 | 4.9 | 1.0 |
| Polysorbate-80 | 2.0 | 0.4 | 0.7 | 0.4 | 2.0 | 0.4 |
| Triethyl citrate | 9.9 | 2.1 | 3.3 | 2.1 | 9.9 | 2.1 |
| Subtotal | 475.3 | 100.0 | 158.4 | 100.0 | 474.3 | 100.0 |
| Hard gelatin capsule #0 or Hydroxypropyl methylcellulose (HPMC) capsule | 96.0 | | 96.0 | | 96.0 | |
| Total | 571.3 | | 254.4 | | 570.3 | |

Figure 1B:
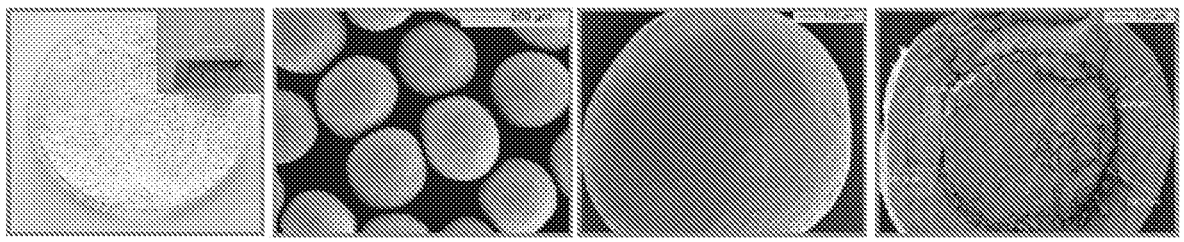
FIG. 1B shows photographs of P3A enteric-coated pellets produced according to an embodiment of the invention.

Representative photographs of P3A delayed-release pellets and capsules are shown in FIG. 1B. The pellets were uniform spheres of 1.0 to 1.3 mm in diameter, with a smooth appearance. Size 0 capsules were filled with the pellets. Each capsule contained approximately 75 mg of P3A (15-16% P3A/pellet) with a weight of approximately 475 mg of active pellet drug product+96 mg empty capsule weight, for a total of approximately 571 mg.

Example 3: pH Dissolution Profile of P3A Delayed-Release Pellets and Stability of P3A Delayed-Release Pellets in Human Chyme Enteric-coated P3A pellets (as formulated in Examples 1 and 2) were held in 0.1M HCL solution for 2 hours followed by incubation in buffers having a pH of 5.5, 5.8, or 6.8, from 15 to 240 minutes. Aliquots were taken at 15, 30, and 45 minutes, and at 45 minutes, 1, 2, 3, and 4 hours for the pH 5.5 and 5.8 samples, and at 1, 2, 3, and 4 hours for the pH 6,8 samples. All sample aliquots were assayed for beta-lactamase activity using the CENTA chromatogenic assay.

Figure 2:
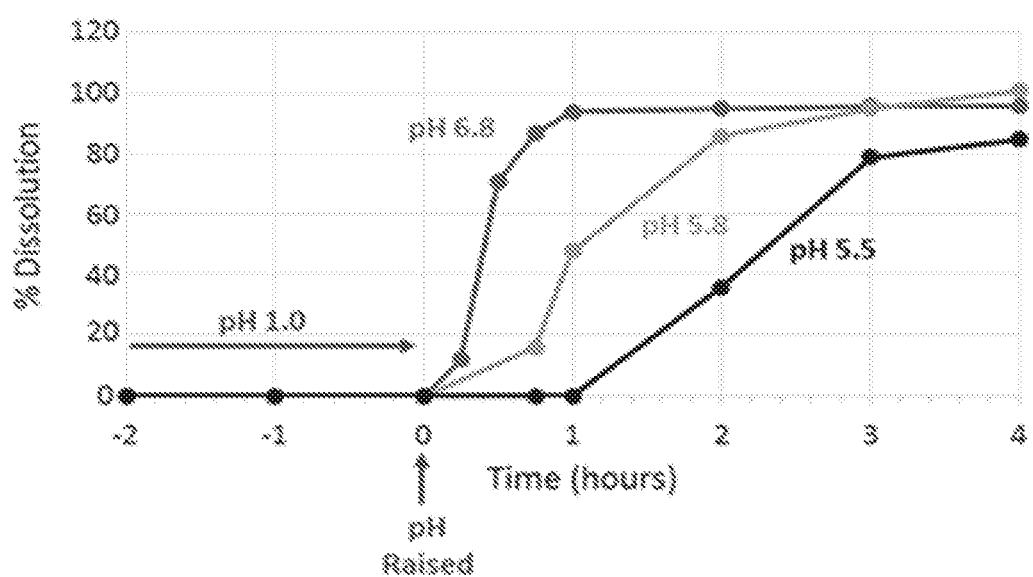
FIG. 2 depicts the pH dissolution profile of P3A pellets produced according to an embodiment of the invention.

As shown in FIG. 2, the P3A enteric-coated pellets were protected at low pH while dissolution occurred at pH of greater than 5.5, with pH 5.8 and 6.8 showing more rapid dissolution than pH 5.5.

Example 4: Stability of P3,4 Delayed-Release Pellets in Human Chyme

The stability of the P3A pellets (as formulated in Examples 1 and 2) in human chyme at 37° C. was evaluated. Specifically, P3A pellets were incubated in five different chyme specimens. Aliquots were taken at 0, 0.5, 1, 2, 3, 4, 5, and 6 hours, and beta-lactamase activity was measured using a CENTA beta-lactamase substrate. Table 4 shows characteristics of the five chime samples used,

TABLE 4

Chyme Specimens

| Specimen | pH | % Liquid | Protease activity (mU/mL) |
|---|---|---|---|
| Chyme 1 | 6.42 | 55 | 5.57 |
| Chyme 2 | 5.98 | 57 | 8.96 |
| Chyme 3 | 5.58 | 57 | 6.63 |
| Chyme 4 | 6.26 | 66 | 6.21 |
| Chyme 5 | 6.56 | 78 | 6.56 |

The percentage activity relative to time of peak activity was calculated for each replicate assay in each chyme and the values were plotted using GraphPad Prism 5.0. The mean relative change in absorbance at 405 nm ($\Delta Ab405$) measured at each time point for all of the chyme specimens showing the release and relative stability of the P3A beta-lactamase activity is presented in FIG. 3.

Figure 3:
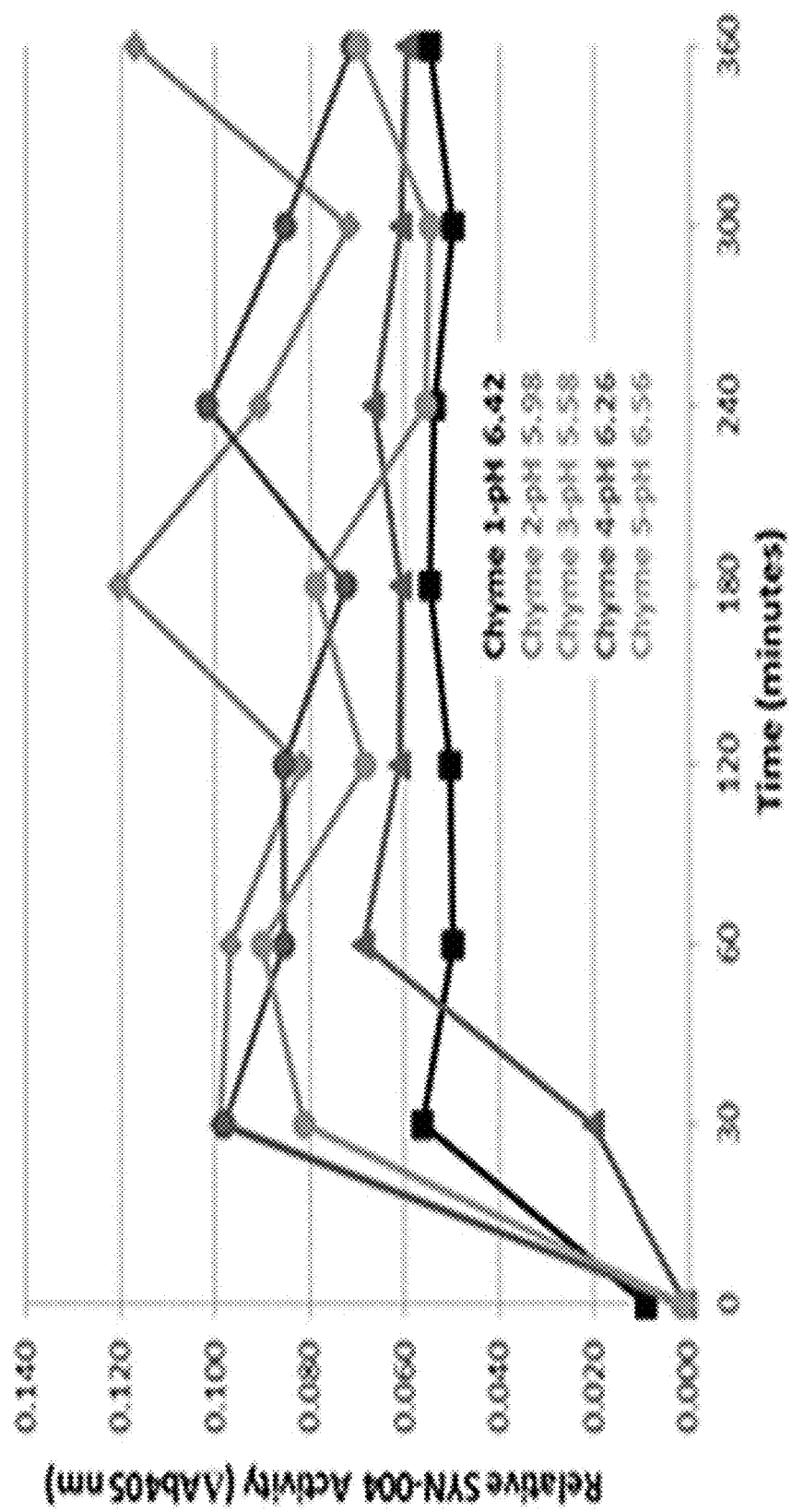
FIG. 3 depicts the stability of P3A pellets in human chyme samples from five different donors.
Figure 4:
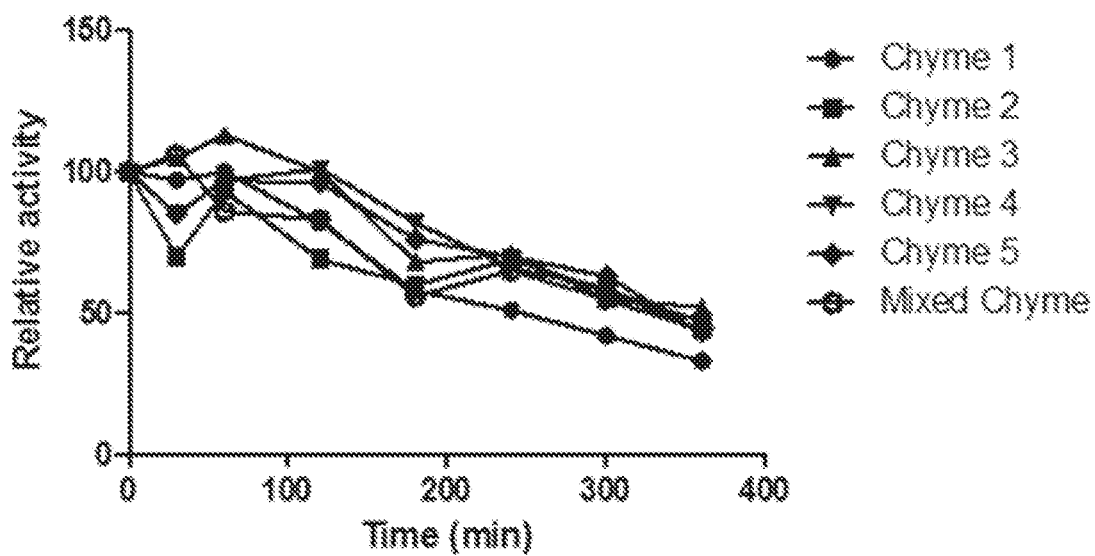
FIG. 4 depicts the stability of P3A in five human chyme samples and a mixed chyme sample.

As shown in FIG. 3, P3A beta-lactamase activity was relatively stable when evaluated in all raw chyme specimens with less than 50% loss in overall activity after 6 hours incubation. Peak activity was detected within 30 minutes in four of the five chyme specimens, indicating that the pellets had completely dissolved within the first 30 minutes of incubation in these chyme samples. In human chyme, P3A pellets displayed a rapid dissolution, within 30-60 minutes, High-level P3A activity was observed for at least 6 hours, demonstrating P3A enzyme stability in human chyme.

Stability of P3A in human chyme was evaluated in both raw and clarified chyme specimens. Incubations of P3A at 37° C. in the chyme specimens were performed in triplicate for each chyme specimen (1 to 5) and the mixed thyme matrix. Samples were removed at 0, 30, 60, 120, 180, 240, 300, and 360 minutes and analysed for beta-lactamase enzymatic activity using a CENTA beta-lactamase substrate. The beta-lactamase activity of the chyme/P3A specimens was determined based on the change of absorbance at 405 nm per min ($\Delta A_{405}/min$) in the first minute (linear portion) of the reaction. The $\Delta A_{405}/min$ values were normalized to a 1 cm path length by dividing the $\Delta A_{405}/min$ value by the determined path length. The mean of the normalized $\Delta A_{405}/min$ values of the individual replicates for each chyme specimen were used to calculate the relative beta-lactamase activity at each time point.

As shown in Table 5, P3A beta-lactamase activity was least stable in clarified chyme 1, displaying a half-life of 243 minutes. The relative stability in the other matrices was greater than 5 hours (300 minutes) for chymes 2, 4, 5, and mixed chyme and greater than 6 hours (360 minutes) for chyme 3.

TABLE 5

Half-Life of P3A Beta-Lactamase Activity in Clarified Chyme

| Matrix | $T_{1/2}$ (min) |
|---|---|
| Chyme 1 | 243 |
| Chyme 2 | 342 |
| Chyme 3 | 394[a] |
| Chyme 4 | 334 |
| Chyme 5 | 328 |
| Mixed Chyme | 325 |

(a) half-life for the chyme 3 specimen was extrapolated from the line equation of y=−0.1621x+113.94 generated by linear regression of the percentage activity from 120 min (the point just prior to which decrease in activity was initially observed) to 360 min.

Example 5: P3A Pellet Mediated Degradation of Ceftriaxone

The beta-lactamase enzymatic activity of formulated pellets containing P1A or P3A (SYN-004) was determined using an in vitro biochemical assay with ceftriaxone as a substrate. The pellets were formulated as previously described in Examples 1 and 2. Specifically, P1A and P3A were dissolved from formulated pellets in 50 mM Potassium Phosphate Buffer 6.8 buffer (pellets manufactured using P1A or P3A drug substance sprayed-dried onto sucrose cores, then sprayed-dried with a protective enteric coating). The concentration of P1A and P3A in the dissolution buffer was determined by HPLC analytical methods and the beta-lactamase enzymatic activity of the dissolved pellets was evaluated for hydrolysis of ceftriaxone using an in vitro biochemical assay.

Figure 5:
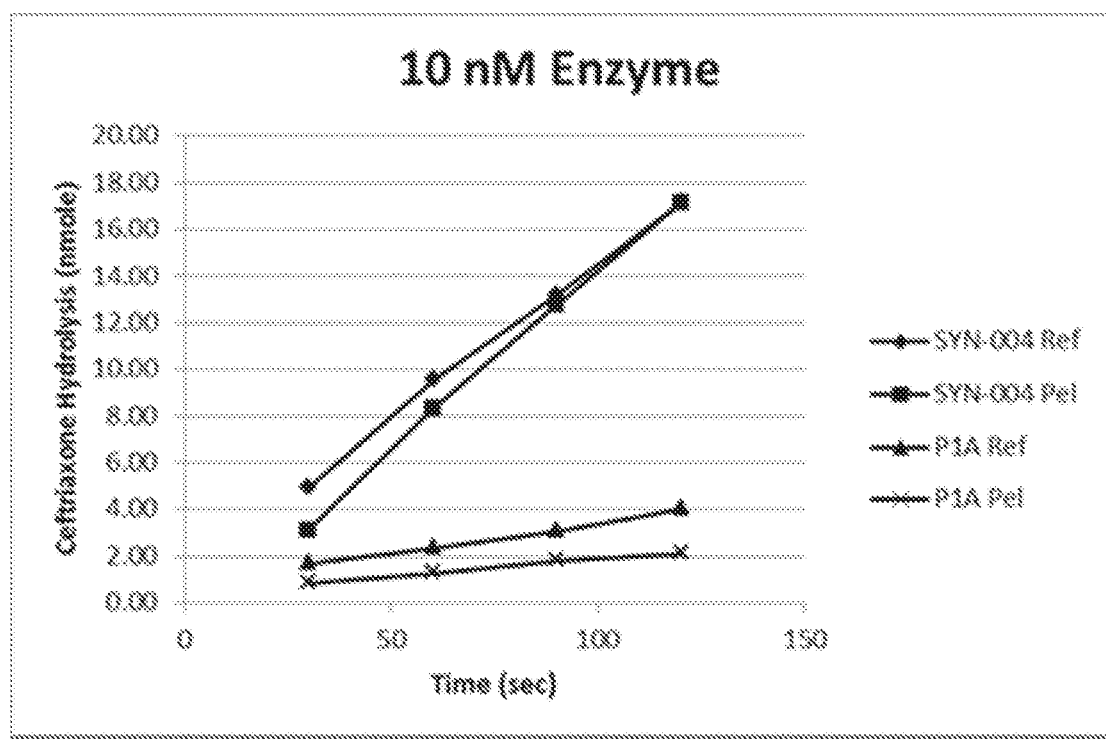
FIG. 5 depicts the amount of hydrolyzed ceftriaxone (nmoles)—at 30, 60, 90, and 120 seconds of digestion with 10 nM P1A or P3A (aka SYN-004) drug substance (Ref) or dissoluted P1A or P3A pellet material (Pel).

As shown in FIG. 5, P3A (aka SYN-004) demonstrated a 3.4-fold greater catalytic rate of ceftriaxone than P1A, with a mean $k_{cat}$ value of 139 $sec^{-1}$ at three concentrations of P3A compared to a mean $k_{cat}$ value of 40.9 $sec^{-1}$ for P1A. The activity of the P1A and P3A dissolved material for hydrolysis of ceftriaxone was comparable to that of the respective drug substance reference standards for each of the beta-lactamases.

Example 6: P3A-Mediated Microbiome Protection

Figure 8:
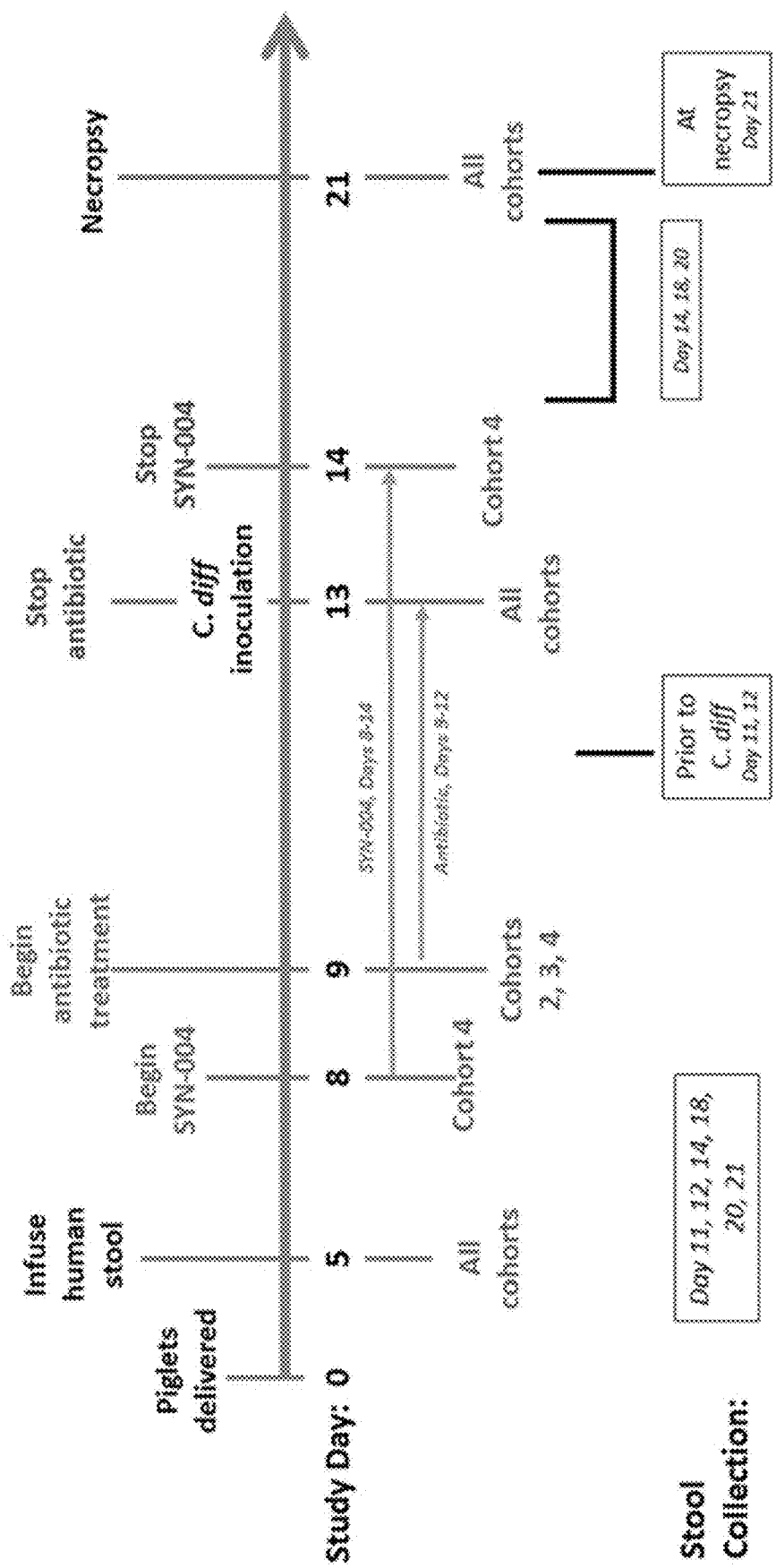
FIG. 8 shows a schematic timeline of a pig study for evaluating P3A (SYN-004)-mediated microbiome protection. Pigs were born via C-section on Day 0 and kept in microisolators. On Day 5, animals were gavaged with a pool of normal human fecal microflora. P3A administration (75 mg/dose, QID) was initiated on Day 8 (Group 4) and continued for 7 days (until Day 14). Antibiotic (clindamycin, 50 mg/kg; Group 2) or ceftriaxone (CRO, 50 mg/kg, Groups 3 and 4) was administered via IP injection once daily beginning on Day 9 and continued for 4 days until Day 12. *C. difficile* ($2.6 \times 10^6$ cfu) was delivered orally to all animals on Day 13. Feces were collected on Days 11, 12, 14, 18, 20 directly from the rectum using sterile cotton swabs and at necropsy on Day 21 directly from the intestinal tract.

The ability of P3A to protect the intestinal microbiome from ceftriaxone (CRO)-induced damage was evaluated in a preliminary study in humanized pigs. The study design and timeline are shown in FIGS. 7 and 8, respectively.

The gastrointestinal (GI) tract of 5 day old gnotobiotic pigs was populated with human adult fecal microflora. Two days later, animals received antibiotics (clindamycin or CRO, IP, 50 mg/kg) for 4 days. P3A was delivered orally 4 times a day (75 mg/dose) for 7 days beginning the day before CRO administration. Specifically, the P3A delayed-release capsules as described in Examples 1 and 2 were administered to the animals. C. difficile (2.6×10⁶ cfu) was delivered orally to all animals on Day 13. Feces were collected on Days 11, 12, 14, 18, 20 directly from the rectum using sterile cotton swabs and at necropsy on Day 21 directly from the intestinal tract. DNA was isolated from the feces and subjected to high-throughput sequencing of the 16S rRNA gene V1V2 region to monitor microbiome changes. The levels of a specific bacterial population expected to be sensitive to CRO, but not to clindamycin, ampicillin-resistant aerobes including those of the phylum Proteobacteria, were assessed by plating equal amounts of Day 21 feces on LB+amp plates. Fecal *C. difficile* Toxin A and interleukin-8 (IL8) were assessed via ELISA as a measure of *C. difficile* infection (CDI). Intestinal tracts collected at necropsy on Day 21 were evaluated histologically for signs of CDI.

None of the animals showed evidence of typical CDI, based on the lack of histopathology typical of CDI and negative ELISA results for *C. difficile* Toxin A and IL8, and negative fecal cultures for *C. difficile*. Two animals were sickly, Pig 9 from Group 1 and Pig 8 from Group 2. Pig 9 did not gain weight and Pig 8 was moribund and euthanized on Day 14, following *C. difficile* infection. However, CDI was not confirmed in Pig 8 or in any study animal.

Figure 9:
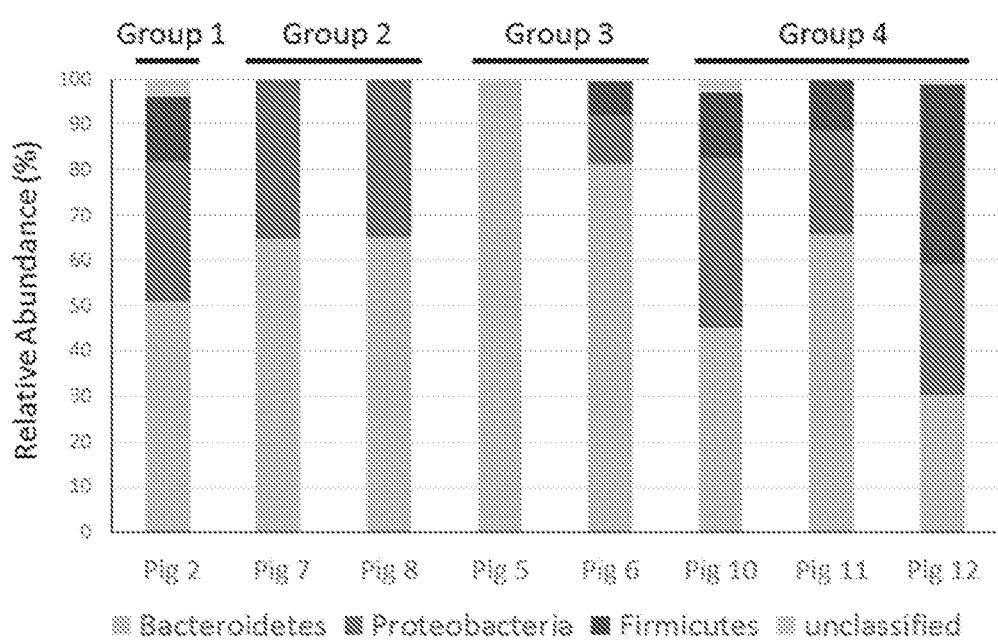
FIG. 9 shows the taxonomic classification of bacteria phyla identified in DNA isolated from pig feces on Study Day 14. In each pig, from bottom up, the bars represent the relative abundance of: bacteroidetes, proteobacteria, firmicutes, and unclassified. For example, in Group 1, bacteria present in the fecal DNA sample of pig 2 showed the presence of all types of bacteria. In Group 2, Pigs 7 and 8 showed the presence of predominantly bacteroidetes and proteobacteria. In Group 3, the fecal DNA sample of Pig 5 showed predominantly bacteroidetes, while pig 6 showed predominantly bacteroidetes, proteobacteria, and firmicutes. In Group 4, Pigs 10 and 12 showed the presence of all types of bacteria, while Pig 11 showed the presence of predominantly bacteroidetes, proteobacteria, and firmicutes.
Figure 10B:
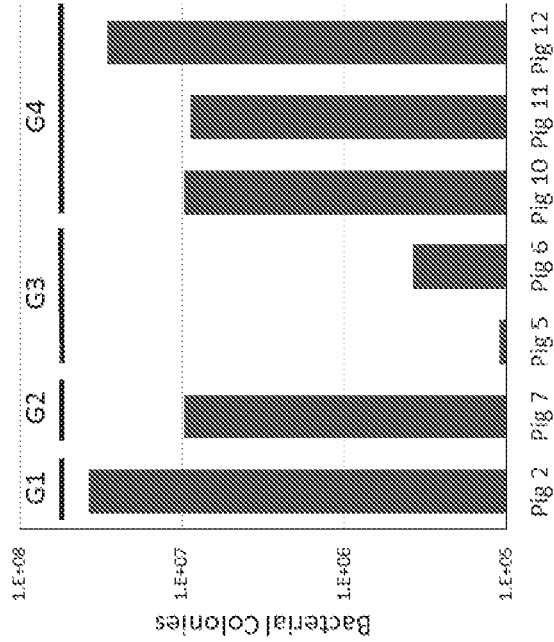
FIGS. 10A and 10B show bacterial growth quantitation from fecal samples collected at necropsy at Study Day 21.
Figure 10A:
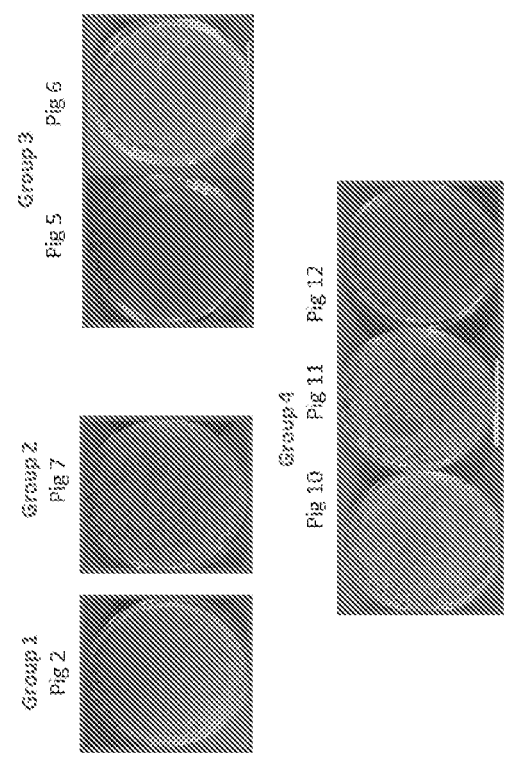

The phylum-level taxonomic classifications of bacteria present in the fecal DNA samples collected on Day 14 are shown in FIG. 9. Group 1 displayed only Pig 2, as Pig 9 did not thrive. Group 1 (no antibiotics) and Group 4 (CRO+ P3A, i.e. SYN-004) looked similar and showed a good representation by Bacteroidetes, Proteobacteria and Firmicutes, while Group 2 (clindamycin) and Group 3 (CRO alone) displayed dysbiosis, with Bacteroidetes as the greatly predominant phylum with no or little representation of Firmicutes. The LB+amp data (FIGS. 10A and 10B) corroborated these findings, as Group 1, Group 2, and Group 4 displayed similar, high bacteria levels, while Group 3 (CRO alone) showed at least two log lower levels, suggesting a reduction in the Proteobacteria population. Notably, clindamycin (Group 2) was not expected to affect ampicillin-resistant aerobes, including those in the phylum Proteobacteria, and mainly killed anaerobic bacteria including those of the phylum Firmicutes. The levels of Proteobacteria present in Groups 1, 2, and 4 were similar (FIG. 9), and Firmicutes were absent from the Group 2 microbiome, consistent with this hypothesis.

These data demonstrate that P3A can protect the human microbiome and may be utilized as a prophylactic therapy designed to prevent antibiotic-mediated microbiome damage, including CDI, in patients receiving beta-lactam antibiotics.

Example 7: Genomic Analysis of P3A-Mediated Microbiome Protection

In order to study the ability of P3A to protect the intestinal microbiome from antibiotics-induced (e.g., ceftriaxone (CRO)-induced) damage, pig fecal samples obtained from the study described above were subjected to additional genomic analysis. Specifically, the 16S rRNA gene V1V2 region was sequenced. In addition, fecal DNA was subjected to whole genome shotgun sequencing. Shotgun sequencing was performed using Illumina HiSeq RAPID RUN, targeting 100 bp single read with the aim to achieve approximately 10-20 million reads per sample (Table 6),

TABLE 6

Shotgun Sequence Data Statistics

| File | Number of reads | Total residue counts | Min read len | Max read len | Average read len |
|---|---|---|---|---|---|
| 3799_112_S7.fasta (G1-P2) | 18605077 | 1854356507 | 35 | 101 | 99.66 |
| 3799_217_S8.fasta (G2-P2) | 20883580 | 2084703775 | 35 | 101 | 99.83 |
| 3799_315_S9.fasta (G3-P5) | 20071353 | 2011723470 | 35 | 101 | 100.23 |
| 3799_316_S10.fasta (G3-P6) | 22624519 | 2271889933 | 35 | 101 | 100.42 |
| 3799_4110_S11.fasta (G4-P10) | 13712842 | 1377348829 | 35 | 101 | 100.44 |
| 3799_4111_S12.fasta (G4-P11) | 20530800 | 2061344856 | 35 | 101 | 100.4 |
| 3799_4112_S13.fasta (G4-P12) | 20580238 | 2068107187 | 35 | 101 | 100.49 |
| 3799_G1_P2_10232014_S3.fasta | 10252196 | 1001456689 | 35 | 101 | 97.68 |
| 3799_G1_P2_10302014_S1.fasta | 59592542 | 5977858476 | 35 | 101 | 100.31 |
| 3799_G2_P7_10232014_S7.fasta | 24846417 | 2491552712 | 35 | 101 | 99.88 |
| 3799_G2_P7_10302014_S1.fasta | 22924500 | 2295666225 | 35 | 101 | 100.14 |
| 3799_G2_P8_10232014_S6.fasta | 16156948 | 1608989121 | 35 | 101 | 99.58 |
| 3799_G3_P5_10232014_S8.fasta | 6940* | 698554 | 35 | 101 | 99.94 |
| 3799_G3_P5_10302014_S2.fasta | 33082874 | 3320035662 | 35 | 101 | 100.36 |
| 3799_G3_P6_10232014_S4.fasta | 22054444 | 2168570854 | 35 | 101 | 98.28 |
| 3799_G3_P6_10302014_S3.fasta | 13521358 | 1357435510 | 35 | 101 | 100.39 |
| 3799_G4_P10_10232014_S9.fasta | 5389698 | 541060855 | 35 | 101 | 100.39 |
| 3799_G4_P10_10302014_S2.fasta | 17012060 | 1695792860 | 35 | 101 | 99.68 |
| 3799_G4_P11_10232014_S6.fasta | 19738* | 1973281 | 35 | 101 | 99.97 |
| 3799_G4_P11_10302014_S4.fasta | 25764488 | 2579825095 | 35 | 101 | 100.13 |
| 3799_G4_P12_10232014_S5.fasta | 76649703 | 7681797089 | 35 | 101 | 100.22 |
| 3799_G4_P12_10302014_S5.fasta | 3312789 | 332575801 | 35 | 101 | 100.39 |

*These two datasets contained too few sequencing reads compared to the other datasets and were eliminated from the comparative analyses These sequence data were classified taxonomically to identify microbial communities associated with the pig fecal samples. Taxonomic classification was performed using bioInformatics algorithms and curated genome databases. Briefly, raw, unassembled shotgun sequence reads were probed against curated GeneBook bacterial and viral databases using GENIUS software package for rapid identification of bacteria communities as well as their relative abundance (Hasan of al., 2014, PLoS ONE 9:e97699; Lax et al., 2014, Science 345:1048). The analyses identified 139 bacterial strains, 79 species, and 35 genera among the treatment groups (Table 7).

TABLE 7

Number of Taxa Detected

| Sample ID | Number of Taxa Detected |
|---|---|
| 3799_112_S7.fasta (G1-P2) | 46 |
| 3799_217_S8.fasta (G2-P2) | 9 |
| 3799_315_S9.fasta (G3-P5) | 27 |

TABLE 7-continued

Number of Taxa Detected

| Sample ID | Number of Taxa Detected |
|---|---|
| 3799_316_S10.fasta (G3-P6) | 58 |
| 3799_4110_S11.fasta (G4-P10) | 51 |
| 3799_4111_S12.fasta (G4-P11) | 23 |
| 3799_4112_S13.fasta (G4-P12) | 57 |
| 3799_G1_P2_10232014_S3.fasta | 56 |
| 3799_G1_P2_10302014_S1.fasta | 55 |
| 3799_G2_P7_10232014_S7.fasta | 11 |
| 3799_G2_P7_10302014_S1.fasta | 8 |
| 3799_G2_P8_10232014_S6.fasta | 6 |
| 3799_G3_P5_10232014_S8.fasta | 1 |
| 3799_G3_P5_10302014_S2.fasta | 27 |
| 3799_G3_P6_10232014_S4.fasta | 62 |
| 3799_G3_P6_10302014_S3.fasta | 49 |
| 3799_G4_P10_10232014_S9.fasta | 52 |
| 3799_G4_P10_10302014_S2.fasta | 48 |
| 3799_G4_P11_10232014_S6.fasta | 2 |
| 3799_G4_P11_10302014_S4.fasta | 20 |
| 3799_G4_P12_10232014_S5.fasta | 66 |
| 3799_G4_P12_10302014_S5.fasta | 19 |

The relative distribution of bacterial taxa among the different treatment groups is shown in Table 8.

TABLE 8

Relative Distribution of Bacterial Taxa Among the Treatment Groups

| Groups | G1 | G2 | G3 | G4 |
|---|---|---|---|---|
| Strain/sub-species | 71 | 17 | 102 | 112 |
| Species | 59 | 12 | 70 | 71 |
| Genus | 27 | 7 | 32 | 30 |

Figure 11A:
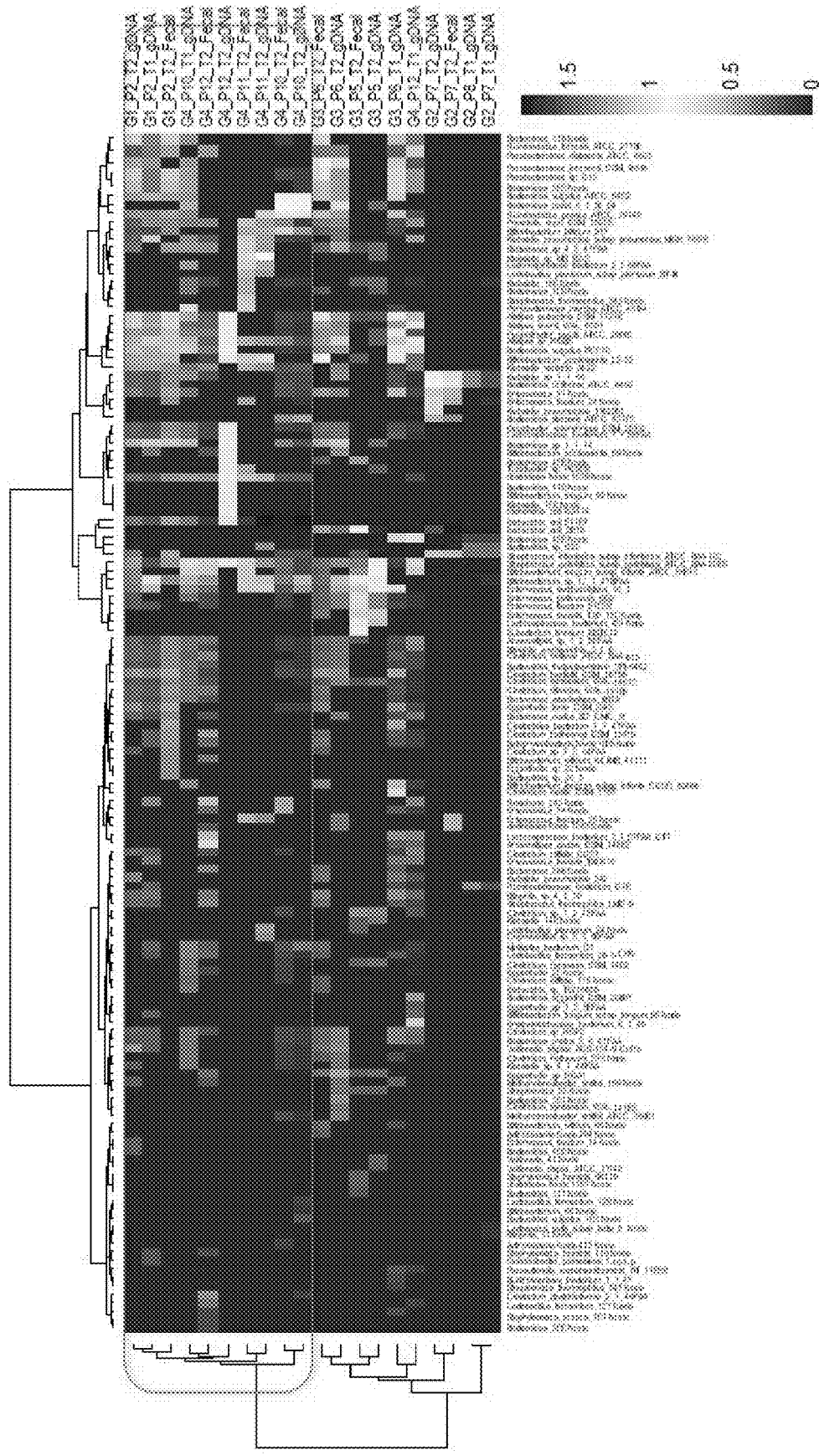
FIGS. 11A and 11B provide a heatmap of bacterial strains in each fecal sample based on relative abundance. The samples were clustered based on compositional similarity of bacterial taxa using the maximum distance function and the Ward Hierarchical Clustering algorithm to create the dendrogram displayed on the top and the left side of the figure. The sample identification is displayed on the right. The box on the top portion of the figure highlights that Group 1 (Control) and Group 4 (Ceftriaxone plus P3A) are more similar to each other than Groups 2 (Clindamycin) and 3 (Ceftrixone alone).
Figure 11B:
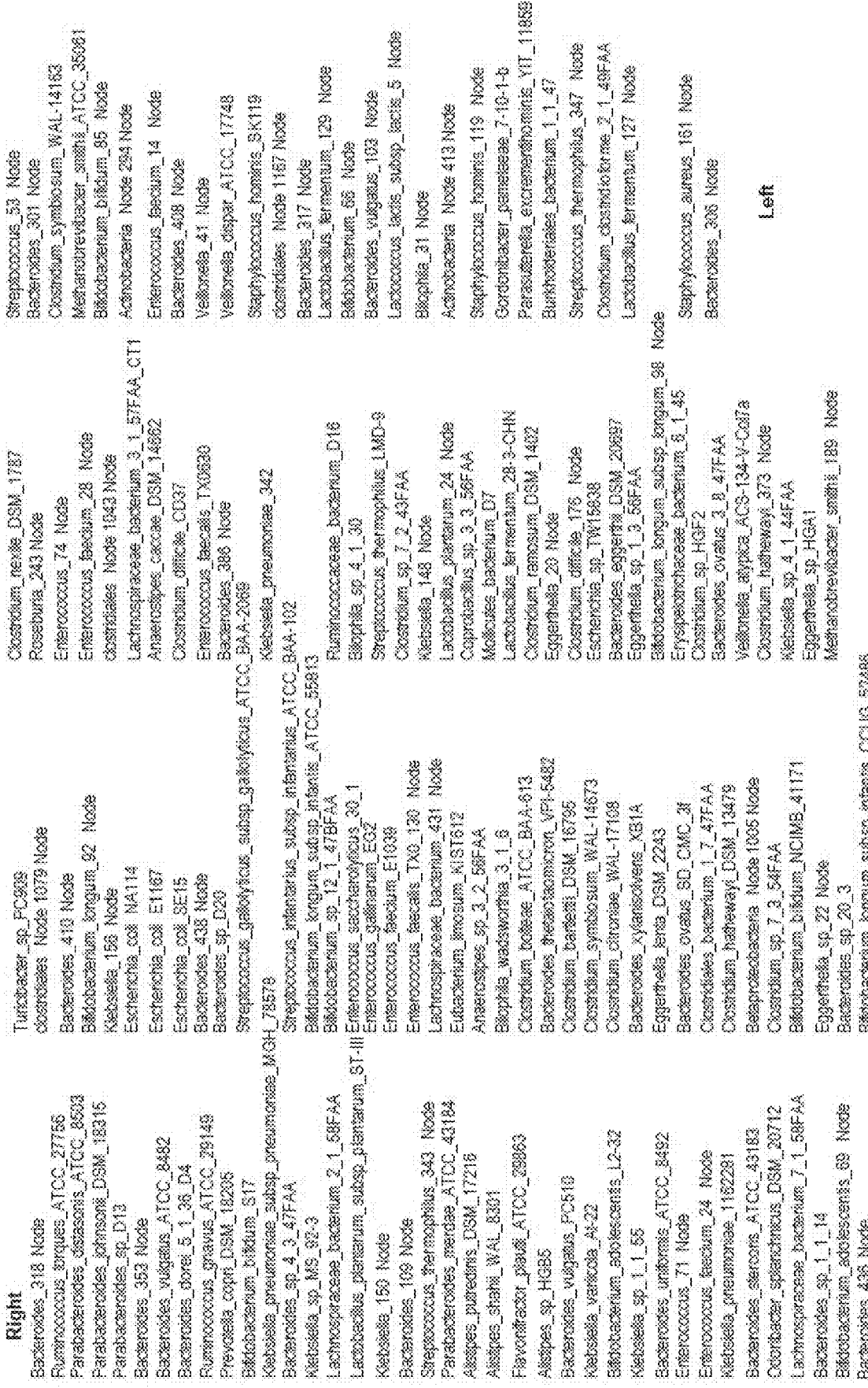
Figure 12:
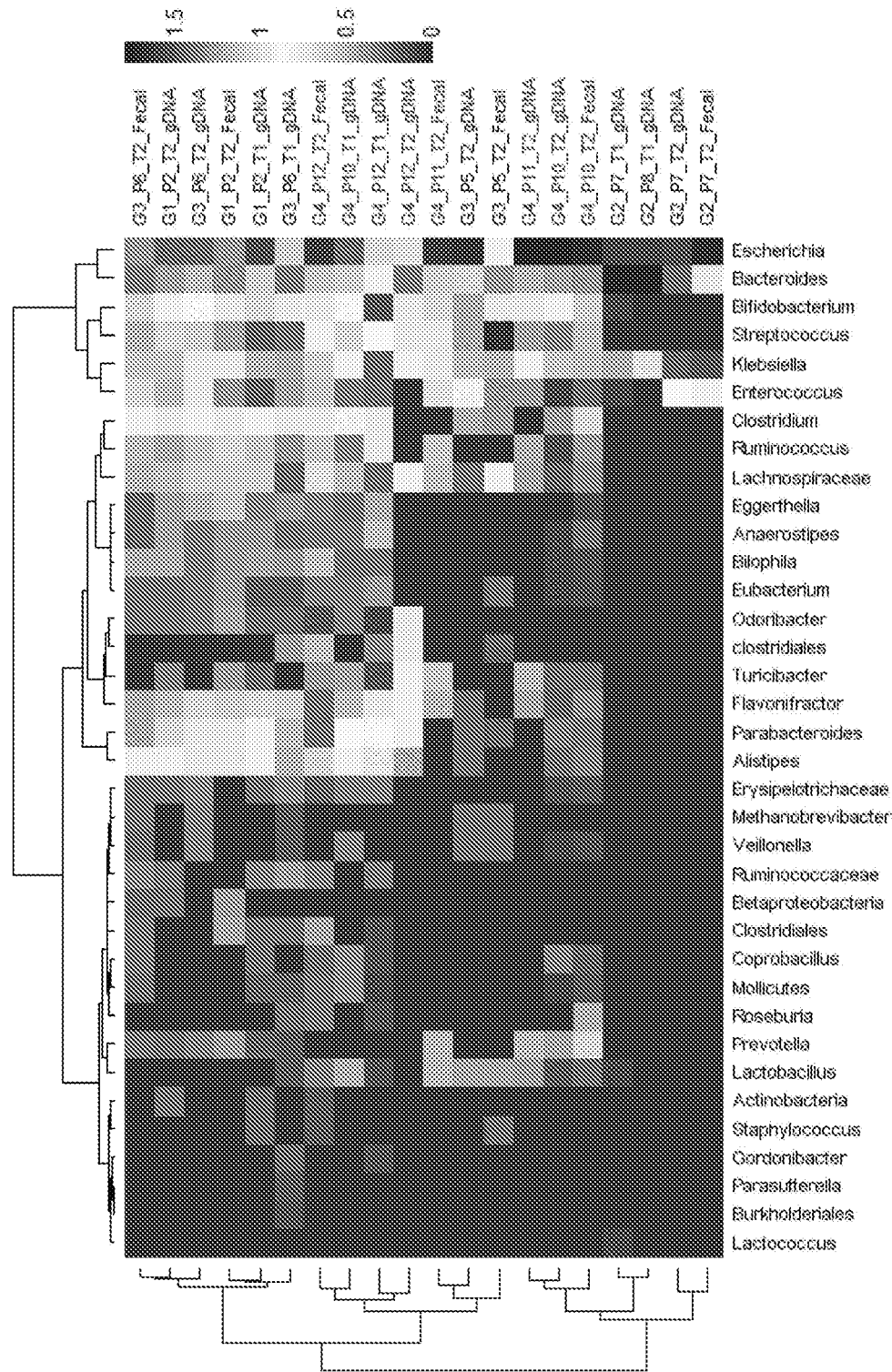
FIG. 12 provides a heatmap of bacterial genera in each fecal sample based on relative abundance. The samples were clustered based on compositional similarity of bacterial taxa using the maximum distance function and the Ward Hierarchical Clustering algorithm to create the dendrogram displayed on the top and the left side of the figure.

Comparative metagenomics analyses were performed by creating heatmaps based on the relative abundance of each bacterial strain in each sample (see FIGS. 11A and 11B) and at the bacterial genus level (see FIG. 12) using the NMF R software package (Gaujoux and Seoighe, 2010, BMC Bioinformatics, 11:367). The samples were clustered using the maximum distance function and the Ward Hierarchical Clustering algorithm. The distance function was used to measure the difference in composition between each of the samples. The clustering algorithm used the distances between each of the samples to create a dendrogram that clustered samples with similar compositions, including both the presence and absence of organisms, in the same clades. Based on the bacterial strain comparisons (FIGS. 11A and 11B), the Group 1 (Control) and Group 4 (Ceftriaxone plus P3A) samples were clustered, highlighted by the blue box (FIGS. 11A and 11B) indicating that Groups 1 and 4 were more similar to each other than Groups 2 (Clindamycin) and 3 (Ceftriaxone alone). These data suggest that P3A functioned to protect the microbiome from the effects of ceftriaxone (Group 3) keeping the microbiome more like the control group (Group 1) that was not exposed to antibiotics.

Figure 13A:
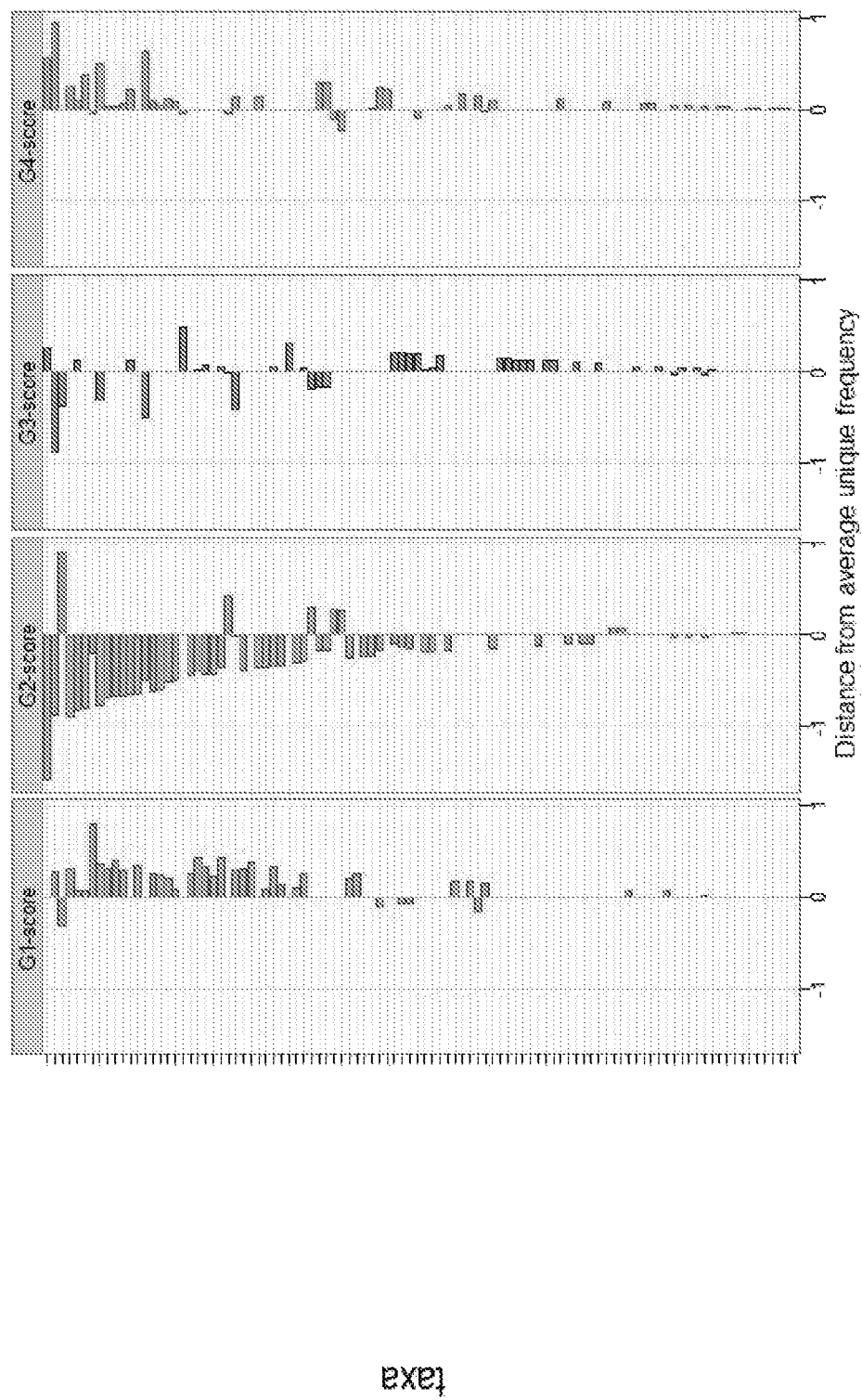
Figure 13B:
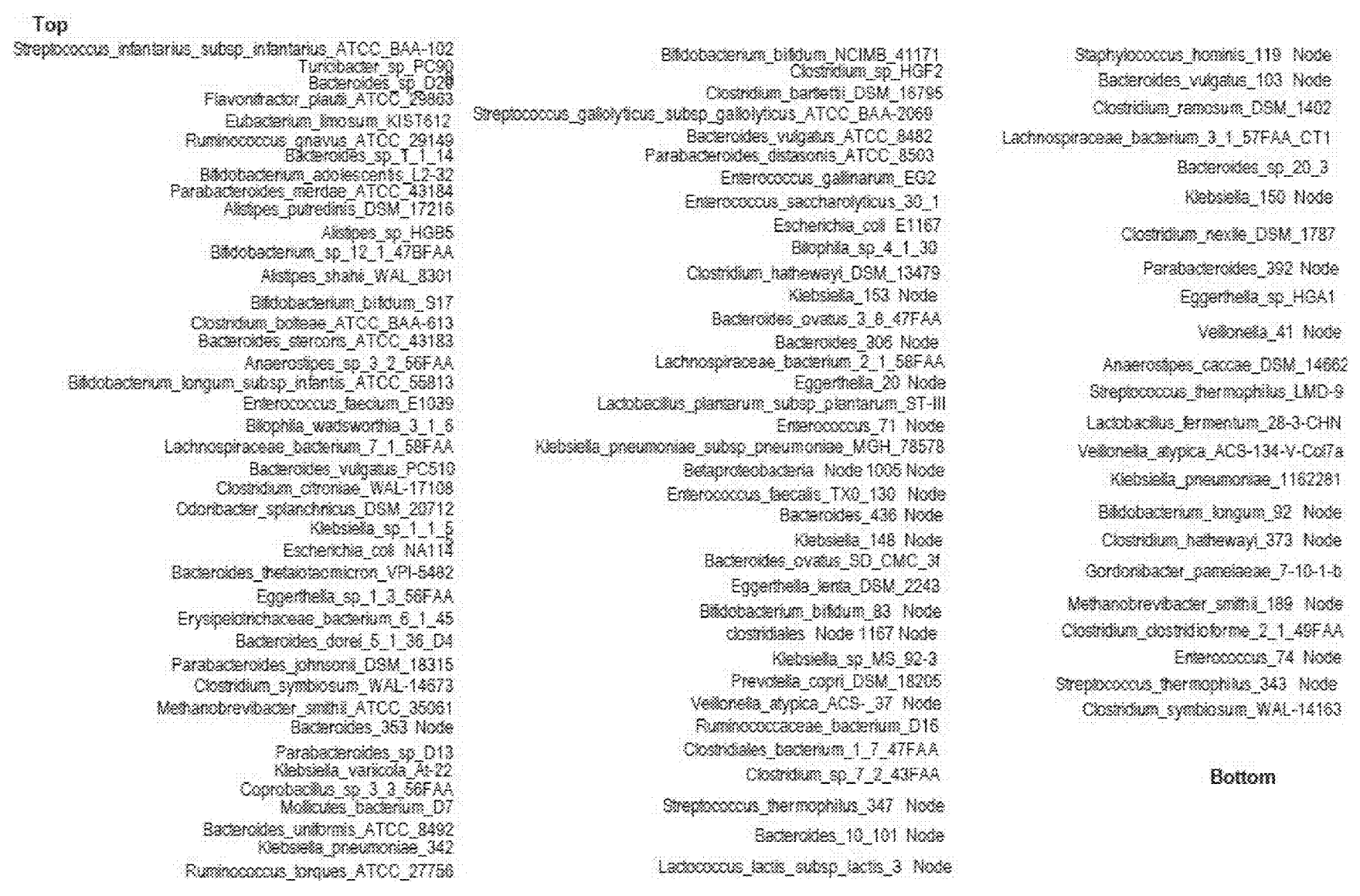

Comparative metagenomics analyses were also performed to investigate changes in the microbiome across different treatment groups. For these analyses, the centroid classification method from the PamR package (Tibshirani of al., 2002, PNAS 99:6567), was used to compare the average frequency (absolute abundance) of each bacterial strain in the samples. The deviation of the centroid of each bacterial strain from each study group was graphed by the overall centroid of all the study groups (FIGS. 13A and 13B).

Figure 14A:
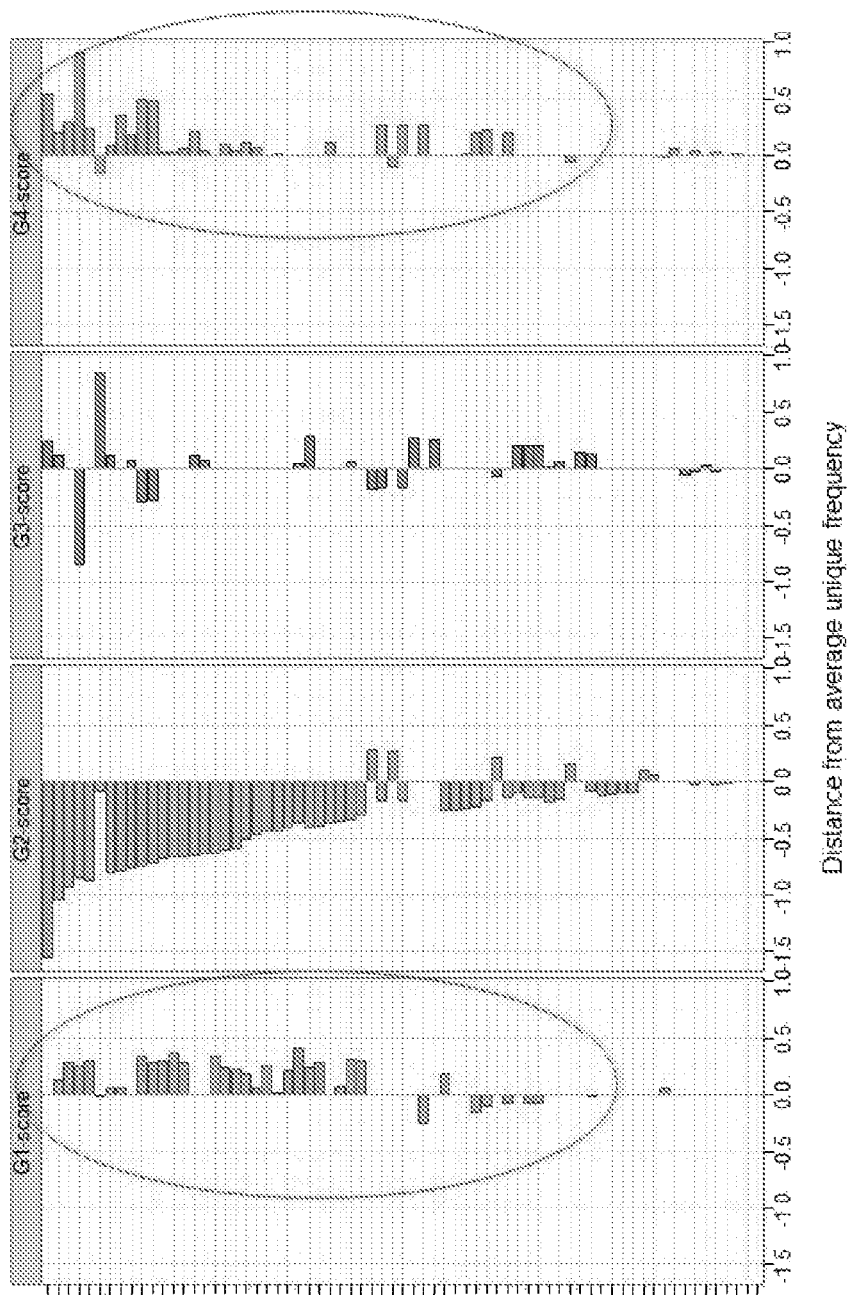
FIGS. 14A and 14B show comparative metagenomic analyses using centroid classification to compare the average deviation of the frequency of each bacterial strain within each study group from the overall average frequency of all the study groups.
Figure 14B:

As the number of sequence reads generated from each individual sample was variable, subsamples from each sample were chosen to represent a subset of 10 million reads. This was done to avoid any bias due to different sample sizes and to enable the measurement of the absolute abundance of the bacterial organisms in the samples. Using these subsets to reduce bias, the comparative metagenomics analyses were performed as described previously for FIGS. 13A and 13B by graphing the deviation of the centroid of each bacterial strain from each study group by the overall centroid of all the study groups (FIGS. 14A and 14B). The data demonstrate that Group 4 (Ceftriaxone plus P3A) displays less severe distortion of species abundance than Group 2 (Clindamycin) or Group 3 (Ceftriaxone alone) when compared to Group 1 (Control) indicating that P3A protected the microbiome from antibiotic-mediated damage.

Figure 15A:
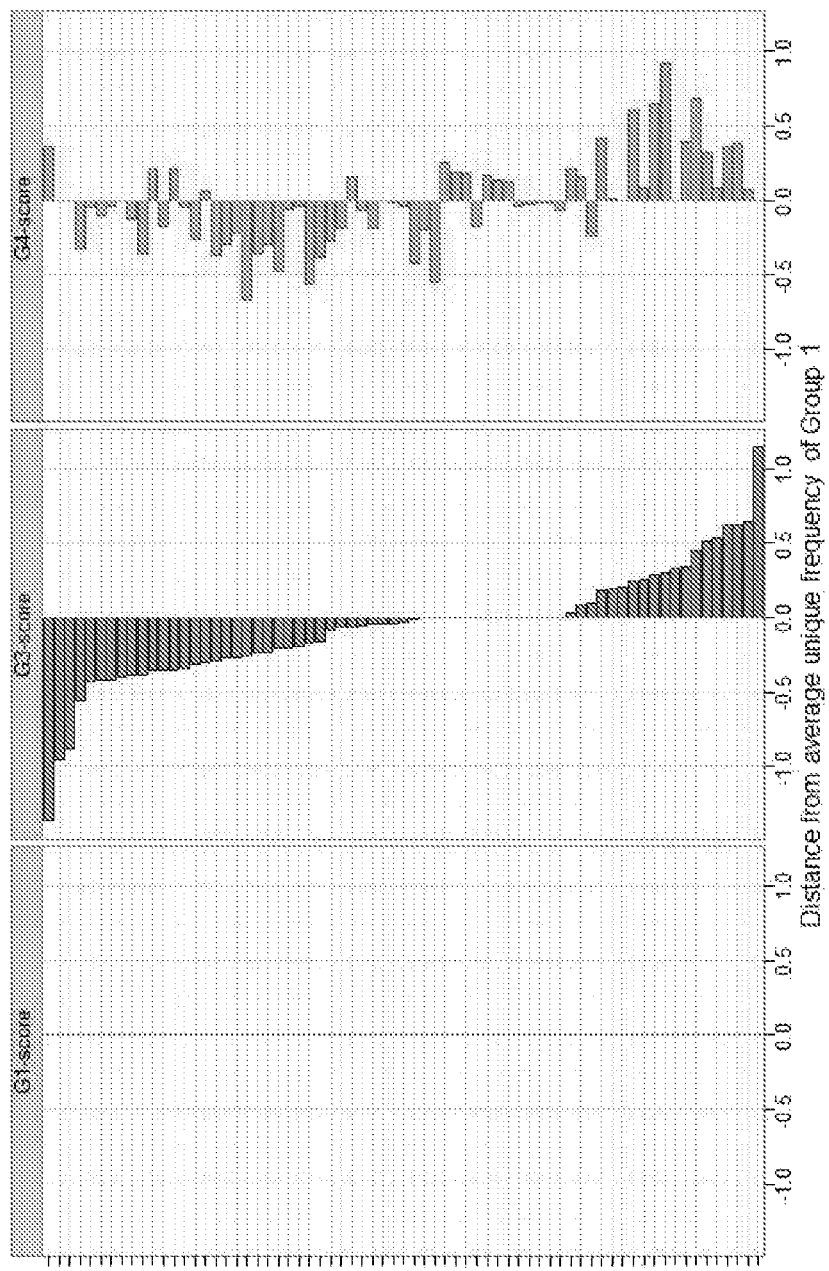

Centroid classification of the sample subsets was also performed at the bacterial species level comparing the average deviation of the frequency of each bacterial species in Group 3 (Ceftriaxone) and Group 4 (Ceftriaxone plus P3A) to Group 1 (Control) (FIGS. 15A and 15B). Notably, Group 3 (Ceftriaxone alone) displayed an underrepresentation of *Turicibacter* spp and an overabundance of the methanogenic archaea, *Methanobrevibacter smithii*, while Group 4 (Ceftriaxone plus P3A) showed similar abundance levels of *Turicibacter* spp and *M. smithii* as Group 1 (Control). Reduction of *Turicibacter* spp. is associated with idiopathic inflammatory bowel disease and acute hemorrhagic diarrhea in dogs (Minamoto et al., 2015, Gut Microbes 6(1), 33-47; Rossi et al., 2014, PLoS ONE 9(4), e94699) while *M. smithii* is a methanogenic archaea species that was reported to be linked to constipation, irritable bowel syndrome, and obesity (Pimentel et at, 2002, Am. J. Gastroenter, Supple. 1:28). Taken together, these data demonstrate that P3A protected the gut microflora from the adverse effects of antibiotic use. Specifically, these data demonstrate that P3A protects the microbiome from a loss of *Turicibacter* spp and an overabundance of methanogens, which were induced by treatment with ceftriaxone. Therefore, a loss of *Turicibacter* spp and the proliferation of methanogens appear to be antibiotic-induced changes to the gut microflora that can be prevented by the use of P3A.

Figure 16A:
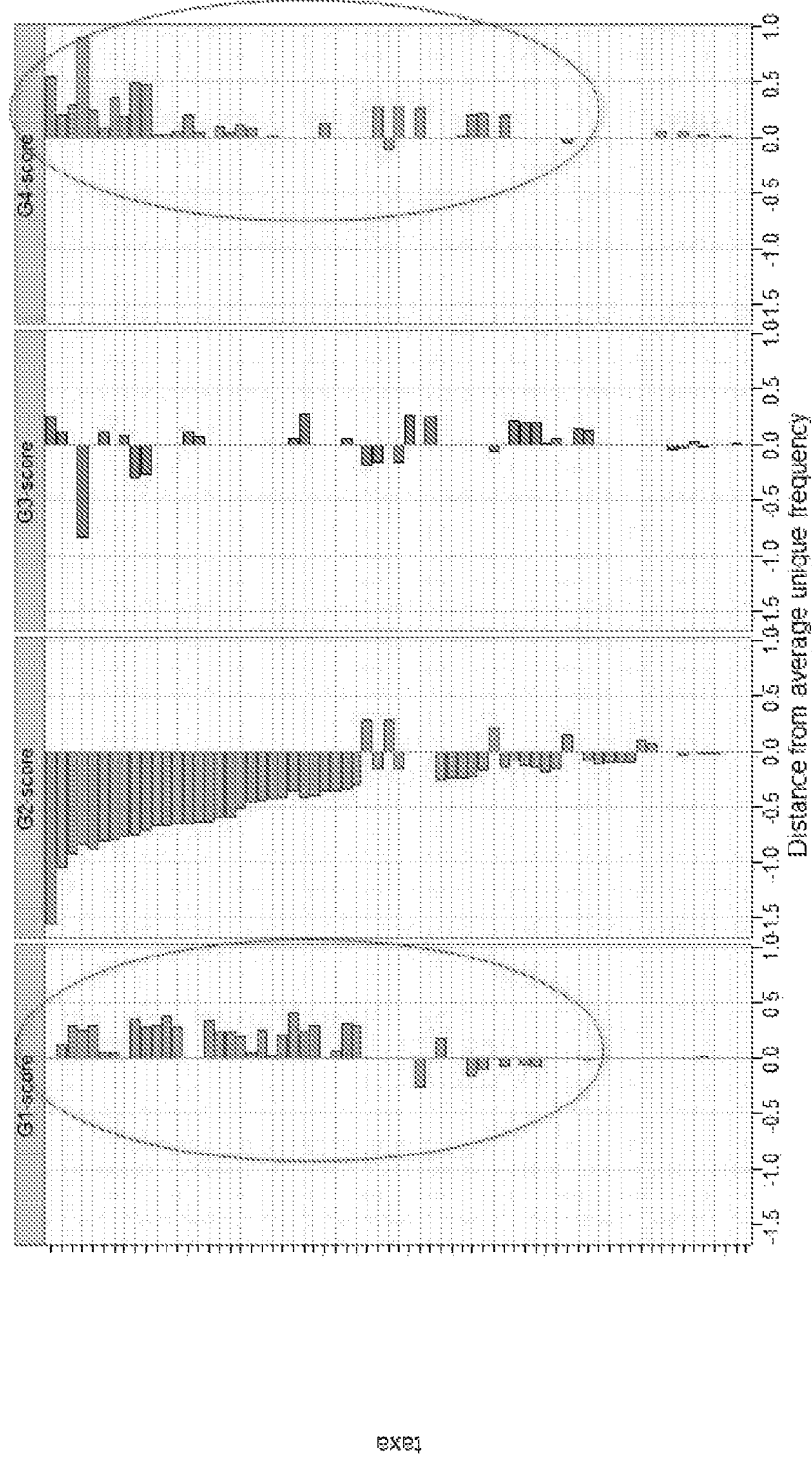
FIGS. 16A and 16B shows species-level centroid classification of sample subsets to compare the average deviation of the frequency of anaerobic and facultative aerobic bacterial species from the average unique frequency of species of all groups. The ovals highlight that Group 4 (Ceftriaxone plus P3A) displayed a more similar pattern of anaerobic and facultative aerobic bacterial species to that of Group 1 (Control) than Group 2 (Clindamycin) or Group 3 (Ceftriaxone alone).
Figure 16B:
Figure 17:
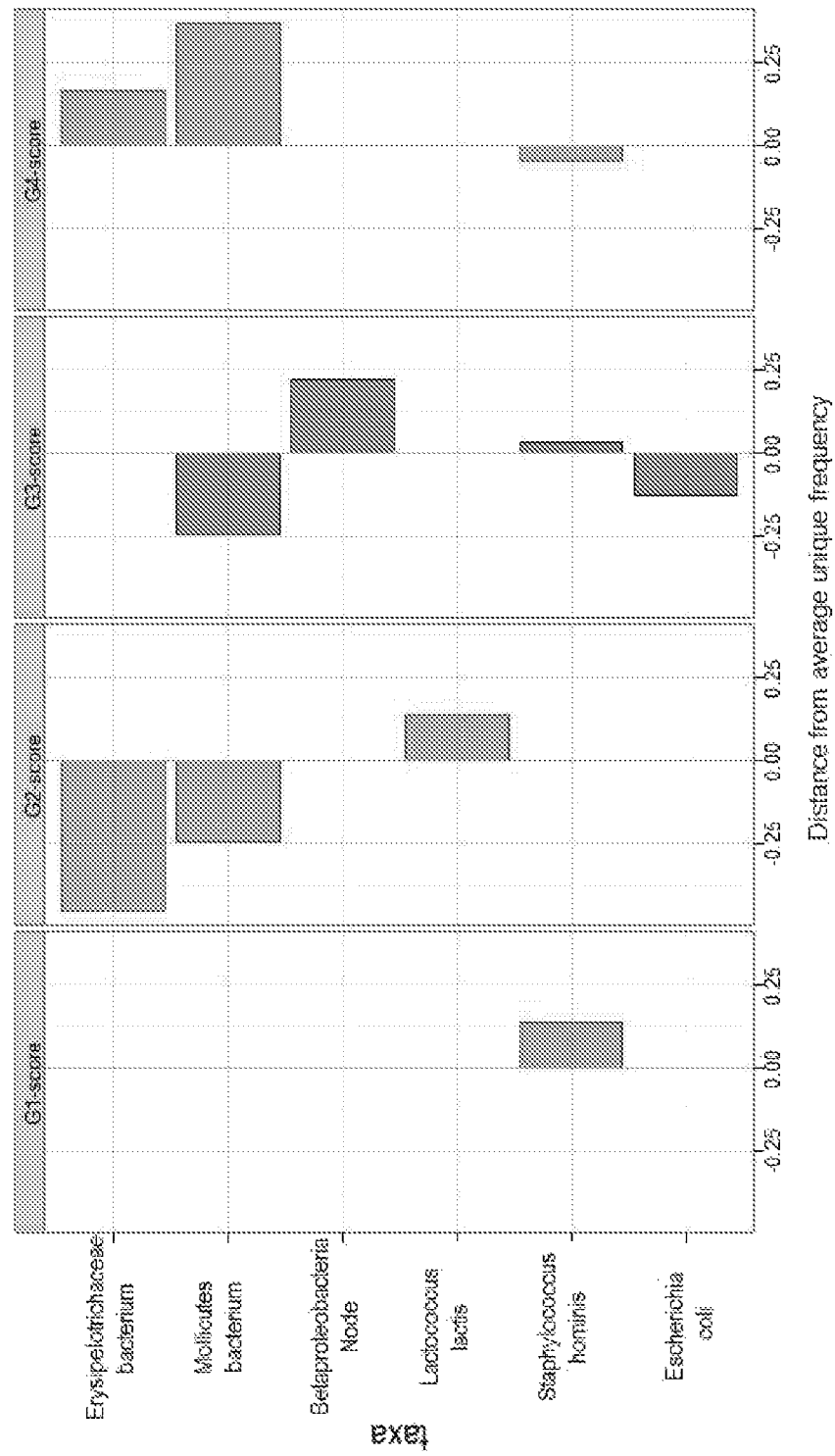
FIG. 17 shows species-level centroid classification of sample subsets to compare the average deviation of the frequency of obligate aerobic bacterial species from the average unique frequency of species of all groups.

In addition, centroid classification of the sample subsets was performed at the bacterial species level comparing the average deviation of the frequency of anaerobic and facultative aerobic bacterial species from the average unique frequency of species in all groups (FIGS. 16A and 16B). The data demonstrate that Group 4 (Ceftriaxone plus P3A) displayed a more similar pattern of anaerobic and facultative aerobic bacterial species to that of Group 1 (Control) than Group 2 (Clindamycin) or Group 3 (Ceftriaxone alone) when compared to Group 1 (Control). Centroid classification of the sample subsets was also performed at the bacterial species level comparing the average deviation of the frequency of obligate aerobic bacterial species from the average unique frequency of species in all groups (FIG. 17). Changes were observed in all groups however Group 4 (Ceftriaxone plus P3A) displayed a different pattern of bacterial species than did Group 3 (Ceftriaxone alone) indicating that P3A changed the pattern of antibiotic-induced changes to the pig gut microflora. These data indicate that P3A was able modify the effect of antibiotics on the gut microbiome by protecting the anaerobic and facultative aerobic bacterial species from antibiotic-mediated changes.

Figure 18:
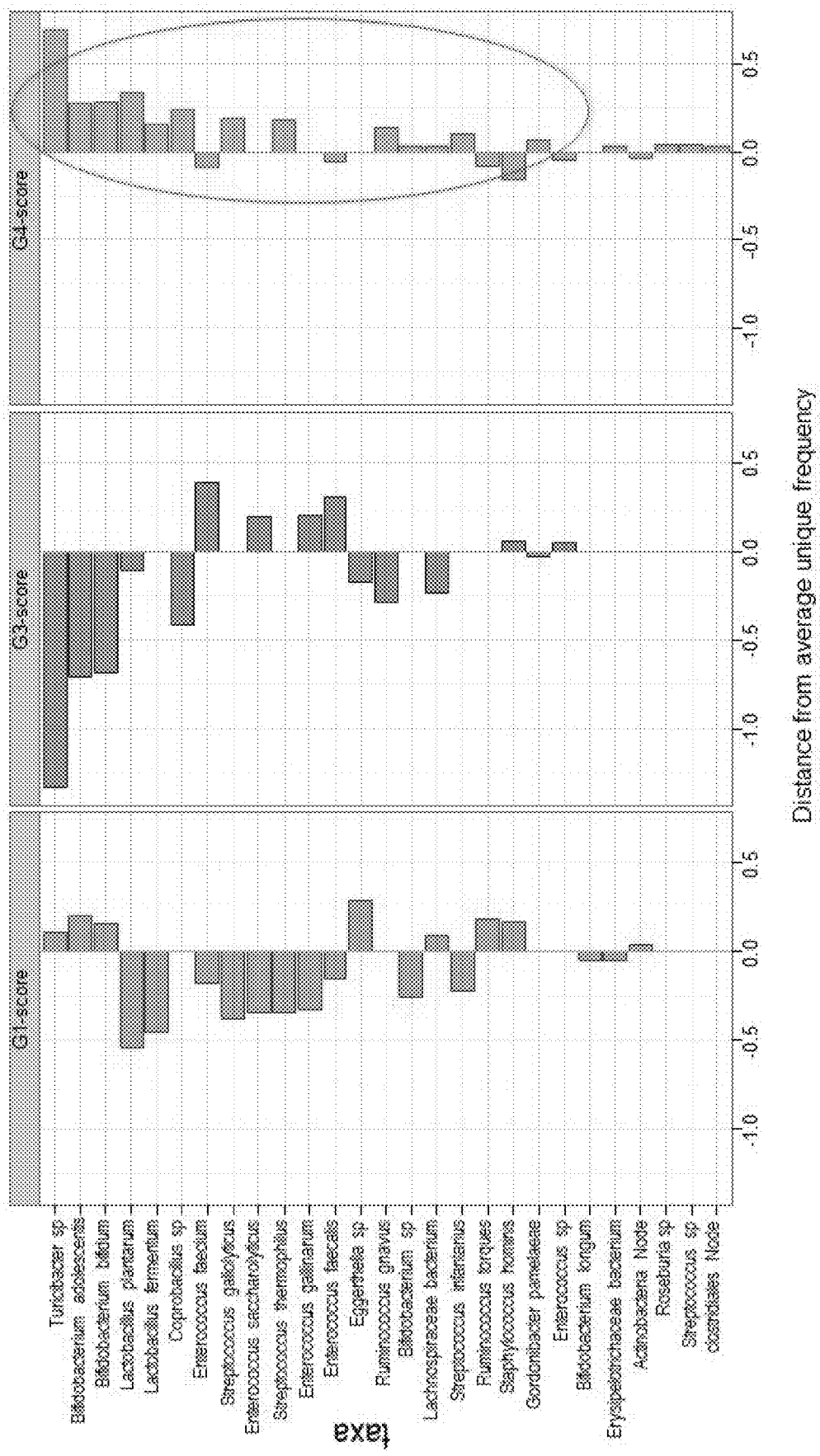
FIG. 18 shows species-level centroid classification of sample subsets to compare the average deviation of the frequency of gram positive bacterial species from the average unique frequency of species from Group 1, Group 2, and Group 3. The oval highlights that Group 4 (Ceftriaxone plus P3A) displayed an overabundance of gram positive species compared to Groups 1 (Control) and Group 3 (Ceftriaxone alone).
Figure 19:
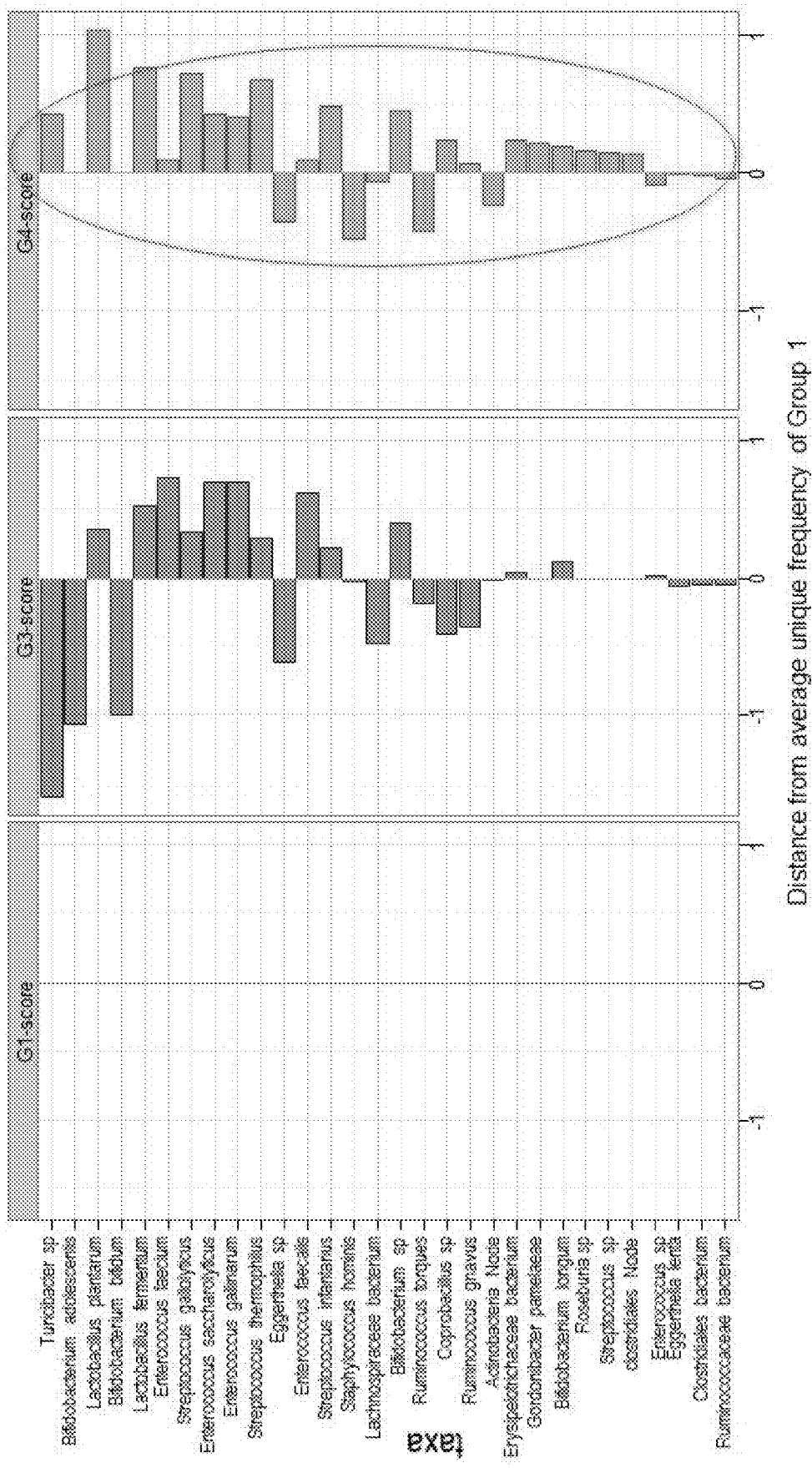
FIG. 19 shows species-level centroid classification of sample subsets to compare the average deviation of the frequency of gram positive bacterial species from the average unique frequency of species from Group 1. The oval highlights that Group 4 (Ceftriaxone plus P3A) displayed an overabundance of gram positive species compared to Group 1 (Control).
Figure 20:
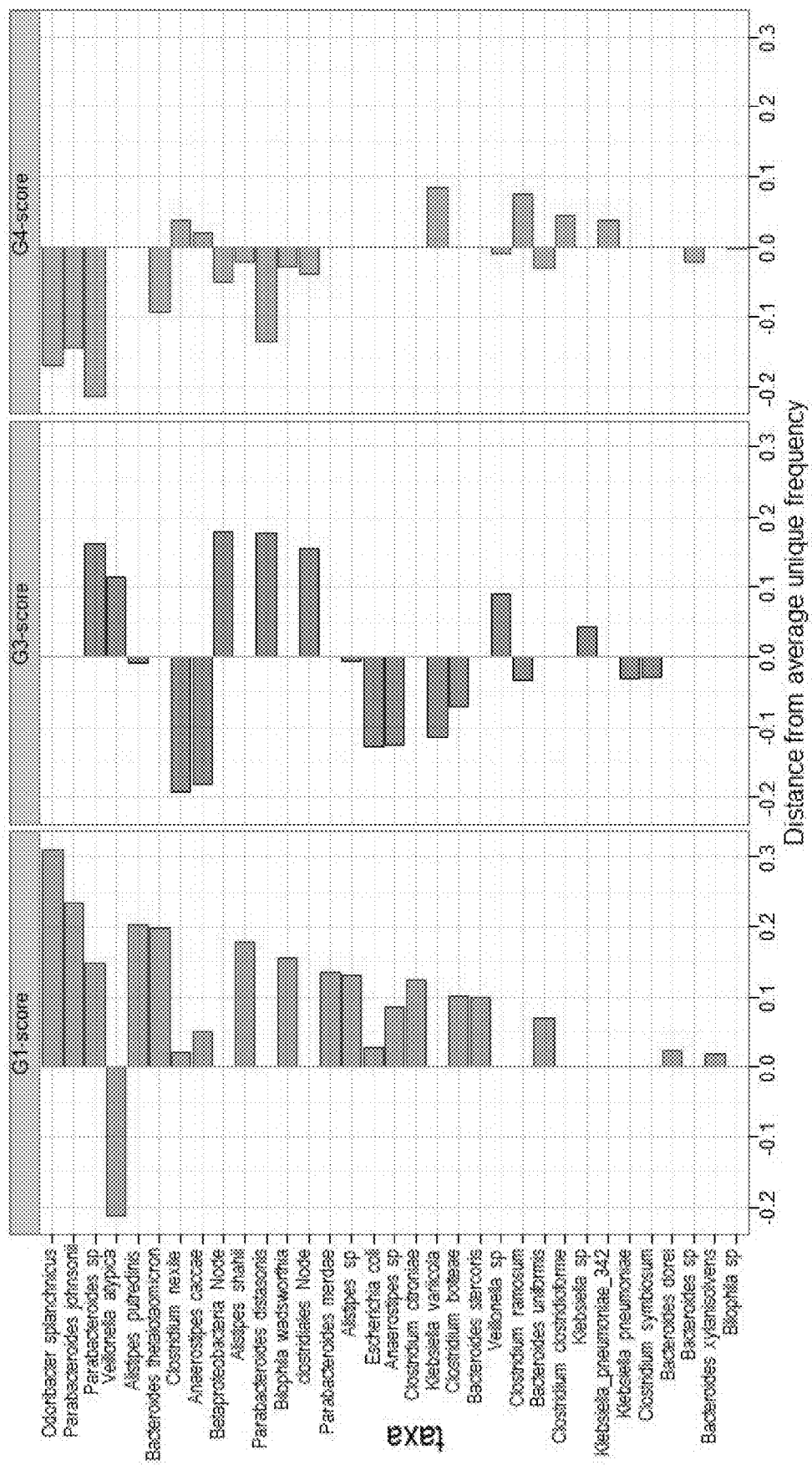
FIG. 20 shows species-level centroid classification of sample subsets to compare the average deviation of the frequency of gram negative bacterial species from the average unique frequency of species from Groups 1, 2, and 3.
Figure 21:
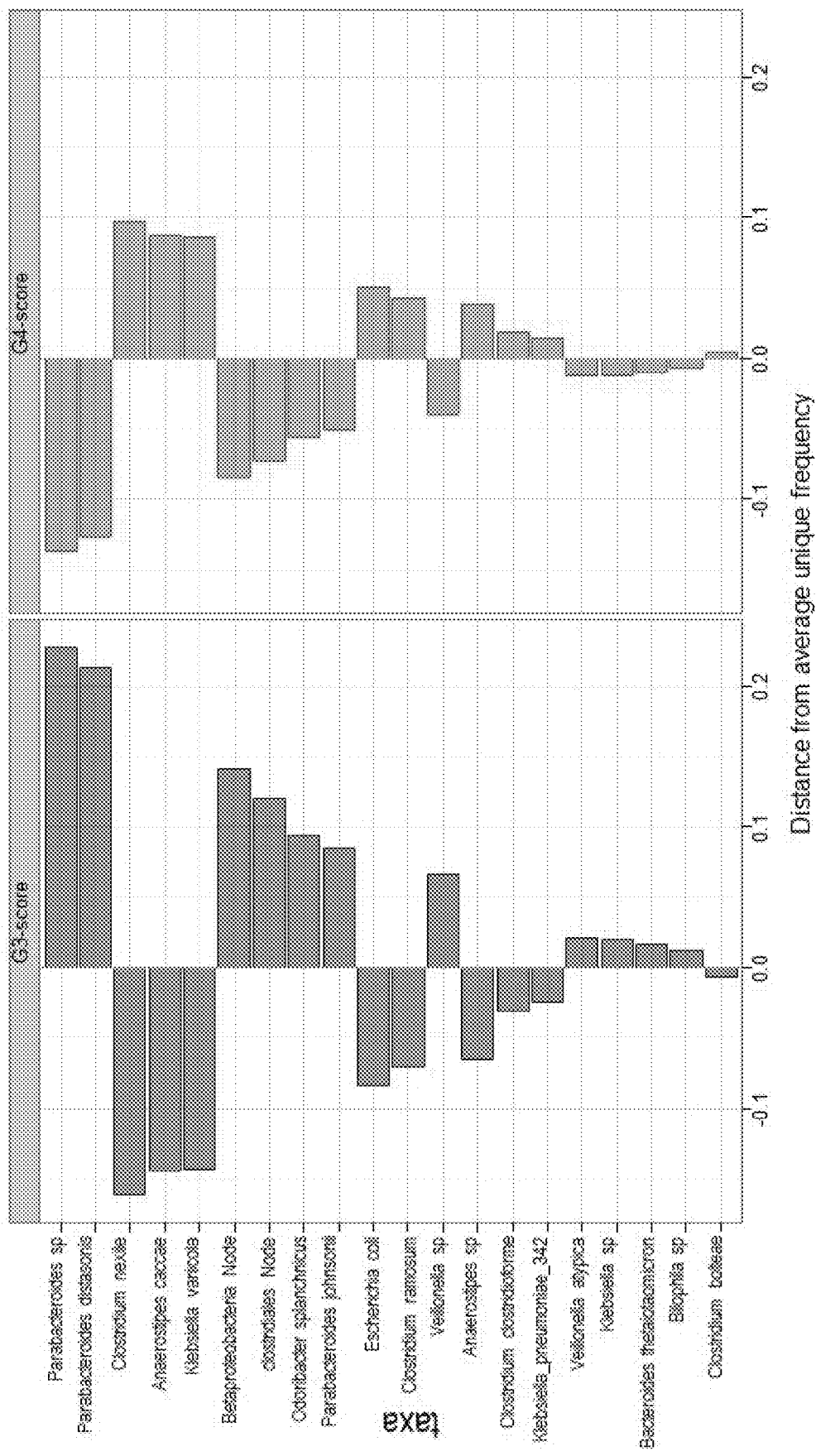
FIG. 21 shows species-level centroid classification of sample subsets to compare the average deviation of the frequency of gram positive bacterial species from the average unique frequency of species from Groups 3 and 4.

Centroid classification of the sample subsets was also performed at the bacterial species level comparing the average deviation of the frequency of gram positive bacterial species from the average unique frequency of species in Groups 1, 3, and 4 (FIG. 18) and compared to the average unique frequency of Group 1 species (FIG. 10). Similarly, centroid classification of the sample subsets was also performed at the bacterial species level comparing the average deviation of the frequency of gram negative bacterial species from the average unique frequency of species in Groups 1, 3, and 4 (FIG. 20) and compared to the average unique frequency of Group 3 and Group 4 species (FIG. 21). The data demonstrate that gram positive organisms are overabundant in the cohort treated with P3A while gram negative organisms are less abundant in the P3A-treated group compared to the antibiotic-alone treated group (Group 3) or the untreated control group (Group 1).

Altogether, these studies indicate, among others, that P3A (i.e. SYN-004) protected the microbiome from antibiotic-induced changes. P3A combated the effects of antibiotics on the composition and load of the gut microbiome compared to treatment with antibiotics alones. Notably, P3A combated the overabundance of methanogens, specifically *M. smithii*, which is an antibiotic-induced change in the gut microflora. *M. smithii* is associated with constipation, irritable bowel syndrome, and obesity (Pimentel et al., 2012, Am. J. Gastroent. Supp. 1:28). P3A also prevented the reduction in the abundance of *Turicibacter* spp., another antibiotic-induced change to the microflora that is associated with idiopathic inflammatory bowel disease and acute hemorrhagic diarrhea in dogs (Minamoto of al., 2015, Gut Microbes 6(1), 33-47; Rossi et al., 2014, PLoS ONE 9(4), e94699).

Example 8. P3A does not Affect Systemic Ceftriaxone Levels

Figure 22:
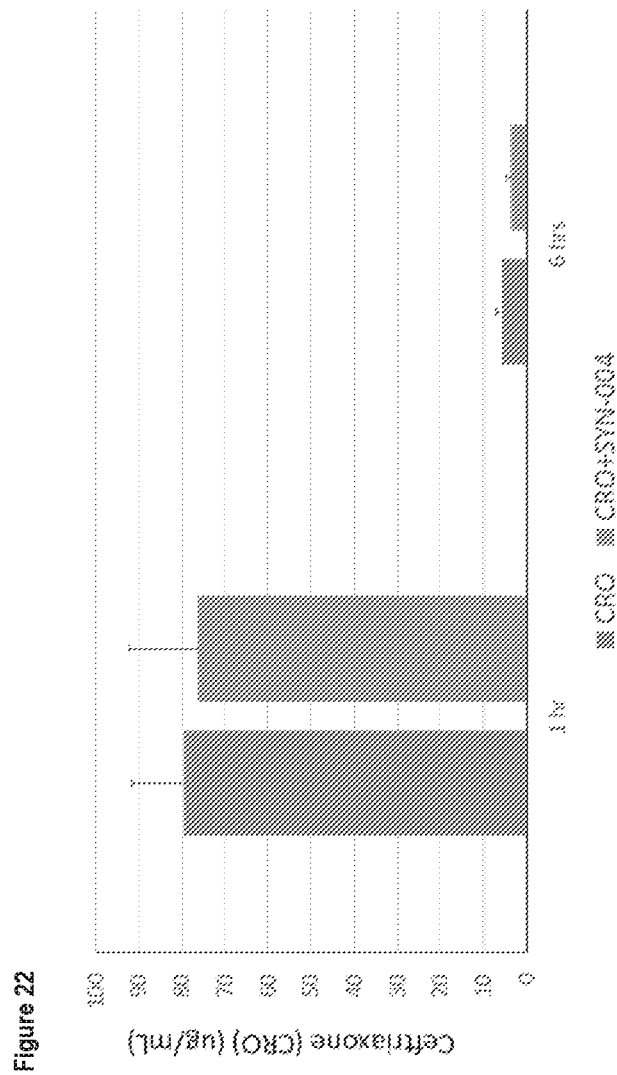
FIG. 22 shows ceftriaxone levels in the serum of treated pigs. A total of 10 pigs were treated once a day with IV ceftriaxone (CRO; 50 mg/kg) for a total of 7 days. A cohort of 5 pigs also received oral P3A (75 mg, four times a day), starting the day before CRO treatment and extending one day after CRO was stopped, for a total of 9 days. On Day 2 of CRO treatment, serum was collected 1, 6, and 19 hours after CRO administration. Serum was assayed for CRO levels using a validated high-performance liquid chromatography assay. Data are displayed as mean and standard deviation. The CRO levels in the serum collected at 19 hours was below the limit of detection of the assay (0.5 ug/mL). For both sets of histograms (1 hour and 6 hours), the left bar is ceftriaxone alone and the right bar is ceftriaxone and P3A.

Another pig study was performed to determine if oral administration of P3A (i.e. SYN-004) had any effect on the systemic levels of antibiotics. For this study, ten Yorkshire piglets, approximately 2 months old and weighing approximately 20 kg were treated with intravenous ceftriaxone (CRO) at 50 mg/kg once a day for seven days. Five animals also received P3A capsules (1 capsule containing 75 mg of P3A, four times a day) beginning the day before CRO treatment and extending to one day after CRO treatment, for a total of nine days. Specifically, the P3A delayed-release capsules as described in Examples 1 and 2 were administered to the animals. On day 2, animals were anesthetized and approximately 9 mls of blood drawn from the vena cava at three timepoints, 1 hour, 6 hours, and 19 hours after CRO administration. Blood was immediately dispensed into a serum separator vacutainer tube. After coagulation, samples were centrifuged and the serum was transferred to a cryovial and stored at −80° C. until analysis. CRO in the serum samples was quantified using a validated high-performance liquid chromatography assay (Owens et al., 2001, Int. J. Antimicrobial Agents, 17:483). A standard curve for CRO was prepared in negative control (untreated) pig serum and contained 6 points ranging from 0.5 to 50 ug/mL. The assay was linear over a range of 0.5 to 50 ug/mL. As shown in FIG. 22, at the one hour time point, the CRO serum levels were 79.43+12.08 ug/mL for the CRO alone treated group and 76.28+15.83 ug/mL for the CRO+P3A treated group. At 6 hours, the CRO serum levels were 5.83+1.15 ug/mL for the CRO alone treated group and 3.76±1.01 ug/mL for the CRO+P3A treated group (FIG. 22). These data demonstrate that P3A had no effect on the peak CRO levels in the treated animals and little if any effect on the 6 hour time point levels. The serum samples taken at 19 hours after CRO treatment were below the limit of detection of the assay (0.5 ug/mL). These data demonstrate that oral delivery of P3A had little or no effect on the serum levels of CRO in pigs, suggesting that P3A was not absorbed systemically and will not interfere with antibiotic efficacy.

Example 9: Additional P3A Formulations

A size 0 or size 1 P3A capsule with 200 mg of the drug product is manufactured to increase P3A drug loading and/or reduce the size of the capsule filled with P3A pellets. Specifically, the P3A is combined with a latex, or other polymer, and then formed into a particulate, micro-encapsulated enzyme preparation, without using a sucrose core. Optionally, the microspheres are covered with a pH-dependent enteric coating.

Figure 6:
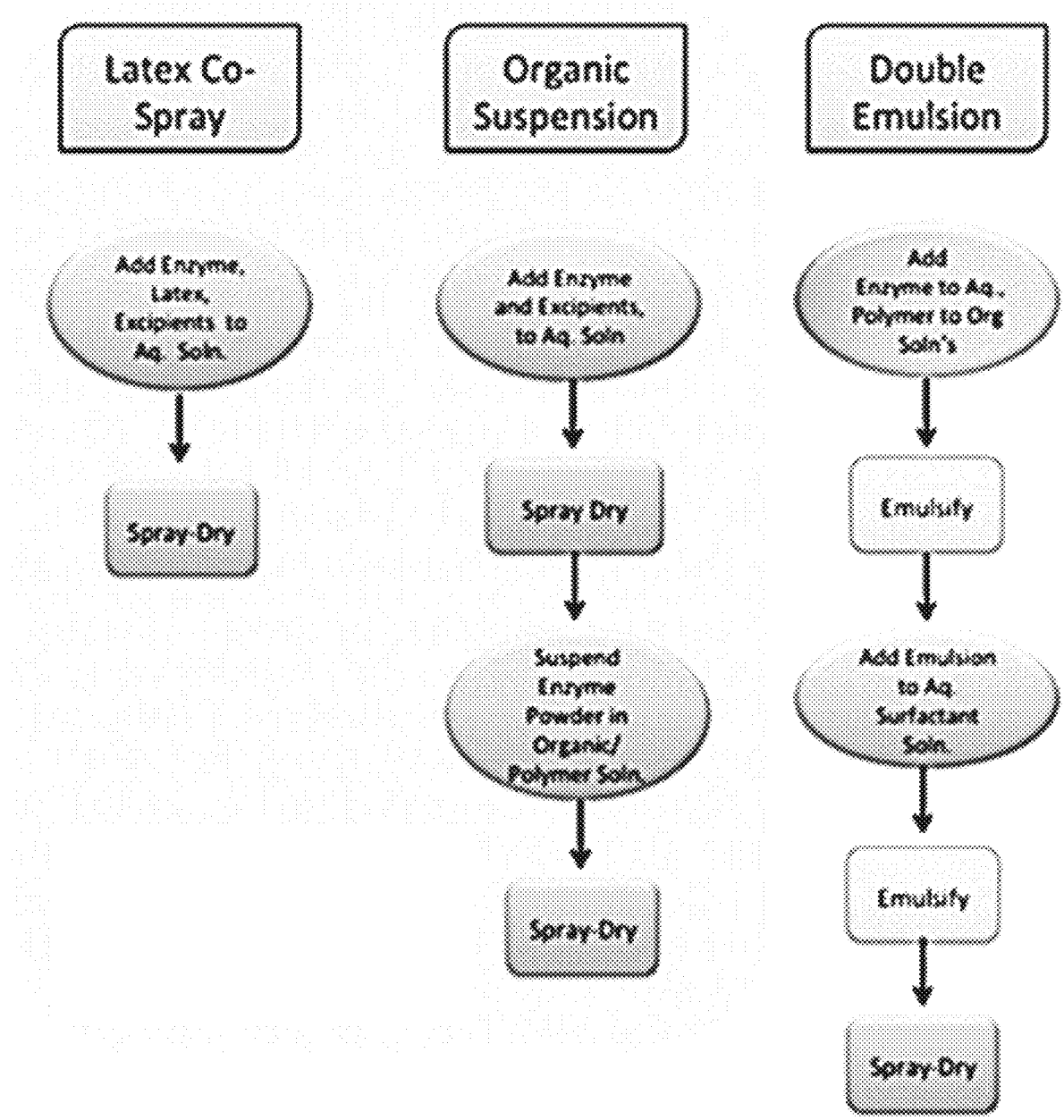
FIG. 6 depicts additional embodiments of a manufacturing process for producing P3A delayed-release capsules.

Three approaches are used for manufacturing this formulation (FIG. 6). First, a particle is developed that has enteric functionality (for example, not released in the stomach, complete release in the small intestine) built into the matrix itself, to reduce excipient load. Optionally enteric coating is added to the particles to provide protection from acidic conditions.

A variety of approaches for generating particulates (such as microspheres, aggregates, other) are known which are amenable to the inclusion of proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres.

Alternatively, the P3A protein and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. The P3A protein retains its activity following this process.

An additional approach uses aqueous phases but no organic solvent. Here, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., beta-lactamases and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the O50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

Hasan N A, Young B A, Minard-Smith A T, Saeed K, Li H, Heizer E M, McMillan M J, Isom R, Abdullah, A S, Bornman D M, Faith S A, Choi S A, Dickens M L, Cebula T A, Colwell R R. (2014). Microbial community profiling of human saliva using shotgun metagenomics sequencing. PLoS ONE 9(5):e97699. Doi:10, 1371/journal.pone.0097699.

Lax S, Smith D P, Marcell J H, Owens S, Handley K, Scott K, Gibbons S, Larsen P, Shogan B D, Weiss S, Metcalf J K, Ursell L K, Vazquez-Baeza Y, Treuren V W, Hasan N A, Gibson M K, Colwell R R, Dantas G, Knight R, Gilbert J A, (2014). Longitudinal analysis of microbial interaction between humans and the indoor environment, Science 345, 1048 (2014); DOI:1126/science.1254529, Gaujox R and Seoighe C. (2010). A flexible R package for nonnegative matrix factorization, BMC Bioinformatics, 11(1), 367.

Tibhirani R, Hastie, T, Narashimhan B, and Chu G. (2002), Diagnosis of multiple cancer types by shrunken centroids of gene expression. PNAS 99(10), 6567-6572.

Pimentel, M, Guynsalus, R P, Rao S S, and Zhang, H. (2012). Methanogens in human health and disease Am. J. Gastroenter. Supp. 1(1), 28-33.

Owens, R C, Tessier, P, Nightingale, C H, Ambrose, P G, Quintiliani, R, Nicolau, D P. (2001). Pharmacodynamics of ceftriaxone and cefixime against community-acquired respiratory tract pathogens, Int. J. Antimicrobial Agents 17(6), 483-489.

Pimentel, M, Guynsalus, R P, Rao S S, and Zhang, H. (2012). Methanogens in human health and disease. Am. J. Gastroenter. Supp. 1(1), 28-33.

Minamoto, Y, Otoni, C. C., Steelman, S. M., Buyukleblebibi, O., Steiner, J. M., Jergens, A. E., Suchodolski, J. S. (2015). Alteration of the fecal microbiota and serum metabolite profiles in dogs with idiopathic inflammatory bowel disease. Gut Microbes 6(1), 33-47.

Rossi, G., Pengo, G., Caldin, M., Piccionello, A. P., Steiner, J. M., Cohen, N. D., Jergens, A. E., Suchodolski, J. S. (2014), Comparison of microbiologics, histological, and immunomodulatory parameters in response to treatment with either combination therapy with prednisone and metronidazole or probiotic VSL #3 strains in dogs with idiopathic inflammatory bowel disease. PLoS ONE 9(4), e94699,

What is claimed is:

1. A method of treating or preventing a *Clostridium difficile* infection (CDI) and/or a *Clostridium difficile*-associated disease in the gastrointestinal tract, comprising administering a modified-release formulation to a patient in need thereof, wherein the formulation comprises at least one modified-release pellet, and wherein each modified-release pellet comprises:
   - about 10-20% by weight of a beta-lactamase which comprises an amino acid sequence having at least 95% sequence identity to SEQ ID NO:1, 3 or 6;
   - about 20-30% by weight sucrose sphere;
   - about 30-40% by weight hydroxypropylcellulose;
   - about 15-25% by weight an enteric polymer;
   - about 1.5-2.5% by weight triethyl citrate;
   - about 0.5-15% by weight glyceryl monostearate;
   - about 0.1-10% by weight polysorbate-80; and
   - about 1-2% by weight of buffer salt.

2. The method of claim 1, wherein each modified-release pellet comprises:
   - about 16% by weight of the beta-lactamase;
   - about 23% by weight sucrose sphere;
   - about 35% by weight hydroxypropylcellulose;
   - about 21% by weight an enteric polymer;
   - about 2% by weight triethyl citrate;
   - about 1% by weight glyceryl monostearate;
   - about 0.5% by weight polysorbate-80; and
   - about 2% by weight of buffer salt.

3. The method of claim 1, wherein each modified-release pellet comprises:
   - about 15.8% by weight of the beta-lactamase;
   - about 23.3% by weight sucrose sphere;
   - about 35% by weight hydroxypropylcellulose;
   - about 20.8% by weight an enteric polymer;
   - about 2.1% by weight triethyl citrate;
   - about 1% by weight glyceryl monostearate;
   - about 0.4% by weight polysorbate-80; and
   - about 1.6% by weight of buffer salt.

4. The method of claim 1, wherein the beta-lactamase comprises an amino acid sequence having at least 95% sequence identity with SEQ ID NO: 1.

5. The method of claim 4, wherein the beta-lactamase comprises an amino acid sequence having at least 95% sequence identity with SEQ ID NO: 1 and an asparagine at Ambler position 276.

6. The method of claim 1, wherein the beta-lactamase is released in the GI tract.

7. The method of claim 6, wherein the beta-lactamase is released in the intestines.

8. The method of claim 1, wherein the formulation is in the form of a capsule.

9. The method of claim 1, wherein each modified-release pellet comprises a core particle and a base coat over the core particle,
   wherein the base coat comprises the beta-lactamase.

10. The method of claim 1, wherein the formulation comprises a plurality of modified-release pellets.

11. The method of claim 1, wherein the formulation further comprises a modified-release coating that is stable in gastric fluid.

12. The method of claim 1, wherein the formulation further comprises a modified-release coating having a solubility that is pH-dependent.

13. The method of claim 12, wherein the modified-release coating comprises a poly(methacrylic acid, methylmethacrylate) compound.

14. The method of claim 1, wherein the CDI or *C. difficile*-associated disease is one or more of: antibiotic-associated diarrhea, *C. difficile* diarrhea (CDD), a *Clostridium difficile* intestinal inflammatory disease, colitis, pseudomembranous colitis, fever, abdominal pain, dehydration and disturbances in electrolytes.

15. A method of treating or preventing a *Clostridium difficile* infection (CDI) and/or a *Clostridium difficile*-associated disease in the gastrointestinal tract, comprising administering a modified-release formulation to a patient in need thereof, wherein the formulation comprises at least one modified-release pellet, and wherein each modified-release pellet comprises:

about 16% by weight of a beta-lactamase;
about 23% by weight sucrose sphere;
about 35% by weight hydroxypropylcellulose;
about 21% by weight an enteric polymer;
about 2% by weight triethyl citrate;
about 1% by weight glyceryl monostearate;
about 0.5% by weight polysorbate-80; and
about 2% by weight of buffer salt;
wherein the beta-lactamase comprises an amino acid sequence having the sequence of SEQ ID NO: 1 with an asparagine at Ambler position 276.

16. The method of claim 15, wherein the CDI or *C. difficile*-associated disease is one or more of: antibiotic-associated diarrhea, *C. difficile* diarrhea (CDD), a *Clostridium difficile* intestinal inflammatory disease, colitis, pseudomembranous colitis, fever, abdominal pain, dehydration and disturbances in electrolytes.

\* \* \* \* \*